(12) United States Patent
Lam et al.

(10) Patent No.: US 6,171,586 B1
(45) Date of Patent: Jan. 9, 2001

(54) ANTIBODY FORMULATION

(75) Inventors: Xanthe M. Lam, San Francisco; James Q. Oeswein, Moss Beach, both of CA (US); Boonsri Ongpipattanakul, Bangkok (TH); Zahra Shahrokh, San Francisco; Sharon X. Wang, San Mateo, both of CA (US); Robert P. Weissburg, Greenville, DE (US); Rita L. Wong, San Mateo, CA (US)

(73) Assignee: Genentech, Inc., South San Francisco, CA (US)

( * ) Notice: Under 35 U.S.C. 154(b), the term of this patent shall be extended for 0 days.

(21) Appl. No.: 09/097,171

(22) Filed: Jun. 12, 1998

Related U.S. Application Data

(60) Provisional application No. 60/053,087, filed on Jun. 13, 1997.

(51) Int. Cl.[7] ......................... A61K 39/395; C12P 21/08

(52) U.S. Cl. ................................. 424/130.1; 424/152.1; 424/141.1; 424/154.1; 424/173.1; 530/388.75

(58) Field of Search ............................ 424/130.1, 152.1, 424/136.1, 141.1, 154.1, 173.1, 133.1; 530/388.75

(56) References Cited

U.S. PATENT DOCUMENTS

| | | |
|---|---|---|
| 4,093,606 | 6/1978 | Coval . |
| 4,457,916 | 7/1984 | Hayashi et al. . |
| 4,499,073 | 2/1985 | Tenold et al. . |
| 4,877,608 | 10/1989 | Lee et al. . |
| 4,940,782 | 7/1990 | Rup et al. . |
| 5,032,405 | 7/1991 | Huang et al. . |
| 5,036,049 | 7/1991 | Audhya et al. . |
| 5,096,885 | 3/1992 | Pearlman et al. . |
| 5,147,637 | 9/1992 | Wright et al. . |
| 5,149,653 | 9/1992 | Roser . |
| 5,215,653 | 6/1993 | Singh et al. . |
| 5,262,296 | 11/1993 | Ogawa et al. . |
| 5,307,640 | 5/1994 | Fawzy et al. . |
| 5,399,670 | 3/1995 | Bhattacharya et al. . |
| 5,506,342 * | 4/1996 | Reno et al. . |
| 5,580,856 * | 12/1996 | Prestrelski et al. . |
| 5,589,167 | 12/1996 | Cleland et al. . |
| 5,608,038 | 3/1997 | Eibl et al. . |
| 5,654,403 * | 8/1997 | Smith et al. . |
| 5,730,980 | 3/1998 | Ulevitch et al. . |
| 5,736,137 * | 4/1998 | Anderson et al. . |
| 5,770,700 * | 6/1998 | Webb et al. . |

FOREIGN PATENT DOCUMENTS

| | | |
|---|---|---|
| 30771/89 | 9/1989 | (AU) . |
| 2138853 | 6/1995 | (CA) . |
| 303746 | 2/1989 | (EP) . |
| 391444 | 10/1990 | (EP) . |
| 661060 | 7/1995 | (EP) . |
| WO 89/09402 | 10/1989 | (WO) . |
| WO 89/11297 | 11/1989 | (WO) . |
| WO 90/11091 | 10/1990 | (WO) . |
| WO 92/22653 | 12/1992 | (WO) . |
| WO 94/11026 | 5/1994 | (WO) . |
| WO94/26302 * | 11/1994 | (WO) . |
| WO 94/26302 | 11/1994 | (WO) . |
| WO 96/41164 | 12/1996 | (WO) . |
| WO 97/04807 | 2/1997 | (WO) . |
| WO97/04801 * | 2/1997 | (WO) . |
| WO97/04807 * | 2/1997 | (WO) . |
| WO 97/04801 | 2/1997 | (WO) . |
| WO97/17087 * | 5/1997 | (WO) . |
| WO 97/17087 | 5/1997 | (WO) . |

OTHER PUBLICATIONS

Cleland et al., "Mechanisms of Nonionic Surfactant Stabilization of Proteins" *Pharmaceutical Research* (Abstract #BIOTEC 2012; Ninth Annual Meeting of the American Association of Pharmaceutical Scientists held in San Diego, CA on Nov. 6–10, 1994) 11(10 Suppl.):S73 (1994).

Steele et al., "Functional Capacity of Immunoglobulin G Preparations and the F(ab')$_2$ split product" *Journal of Clinical Microbiology* 27(4):640–643 (Apr. 1989).

Akers, M., "Considerations in selecting antimicrobial preservative agents for parenteral product development" *Pharmaceutical Technology* pp. 36–40;43–44;46 (May 1984).

Albelda et al., "Integrins and other cell adhesion molecules" *FASEB–J* 4(11):2868–2880 (1990).

Arakawa et al., "Protein–Solvent Interactions in Pharmaceutical Formulations" *Pharmaceutical Research* 8(3):285–291 (1991).

Bam et al., "Stability of Protein Formulations: Investigation of Surfactant Effects by a Novel EPR Spectroscopic Technique" *Pharm. Res.* 12:2–11 (1995).

Beauvais et al., "Both Glassy State and Native Structure are Required for Storage Stability of Lyophilized Interleukin–1 Receptor Antagonist" *Pharm. Res.* (Abstract #2007) 12(9):S–80 (1995).

Bogard et al., "Practical considerations in the production, purification, and formulation of monoclonal antibodies for immunoscintigraphy and immunotherapy" *Seminars in Nuclear Medicine* 19(3):202–220 (1989).

Chang and Fischer, "Development of an Efficient Single–Step Freeze–Drying Cycle for Protein Formulations" *Pharm. Res.* 12(6):831–837 (1995).

Chang et al., "Development of a Stable Freeze–dried Formulation of Recombinant Human Interleukin–1 Receptor Antagonist" *Pharmaceutical Research* 13(2):243–248 (1996).

Chang et al., "Nucleotide sequence of the alkaline phosphatase gene of *Escherichia coli*" *Gene* 44:121–125 (1986).

Clarke et al., "Lability of Asparagine and Aspartic Acid Residues in Proteins and Peptides" *Stability of Protein Pharmaceuticals, Part A: Chemical and Physical Pathways of Protein Degradation*, T.J. Ahern and M.C. Manning, New York:Plenum Press, Chapter 1, pp. 1–29 (1992).

(List continued on next page.)

*Primary Examiner*—Patrick Nolan
*Assistant Examiner*—Marianne DiBrino
(74) *Attorney, Agent, or Firm*—Lee K. Tan; Wendy M. Lee

(57) ABSTRACT

A stable aqueous pharmaceutical formulation comprising a therapeutically effective amount of an antibody not subjected to prior lyophilization, a buffer maintaining the pH in the range from about 4.5 to about 6.0, a surfactant and a polyol is described, along with uses for such a formulation.

29 Claims, 25 Drawing Sheets

OTHER PUBLICATIONS

Cleland and Jones, "Development of Stable Protein Formulations for Microencapsulation in Biodegradable Polymers" *Proceed. Intern. Symp. Control. Rel. Bioact. Mater.* 22:514–515 (1995).

Cleland et al., "The Development of Stable Protein Formulations: A Close Look at Protein Aggregation, Deamidation, and Oxidation" *Critical Reviews in Therapeutic Drug Carrier Systems* 10(4):307–377 (1993).

Draber et al., "Stability of Monoclonal IgM Antibodies Freeze–Dried in the Presence of Trehalose" *Journal of Immunological Methods* 181(1):37–43 (1995).

Hernandez et al., "Role of neutrophils in ischemia–reperfusion–induced microvascular injury"*Am. J. Physiol.* 253(3 Pt 2):H699–H703 (1987).

Hildreth et al., "The human lymphocyte function–associated (HLFA) antigen and a related macrophage differentiation antigen (HMac–1): functional effects of subunit–specific monoclonal antibodies"*J. Immunol.* 134:3272–3280 (1985).

Hildreth et al., "A Human Lymphocyte–associated Antigen Involved in Cell–mediated Lympholysis" *European Journal of Immunology* 13:202–208 (1983).

Hynes, "Integrins: versatility, modulation, and signaling in cell adhesion" *Cell* 69(1):11–25 (1992).

Izutsu et al., "The effects of additives on the stability of freeze–dried β–galactosidase stored at elevated temperature" *Intl. J. Pharmaceutics* 71:137–146 (1991).

Jutila et al., "Inflammation–induced endothelial cell adhesion to lymphocytes, neutrophils, and monocytes" *Transplantation* 48(5):727–731 (1989).

Kossiakoff, A.A., "Tertiary Structure Is a Principal Determinant to Protein Deamidation" *Science* 240:191–194 (1988).

Lam et al., "Microencapsulation of Recombinant Humanized Monoclonal Antibody for Local Delivery" *Proceedings of the 24th International Symposium on Controlled Release of Bioactive Materials* 24:759–760 (Jun. 15–19, 1997).

Lam et al., "Microencapsulation of Recombinant Humanized Monoclonal Antibody for Local Delivery" *American Association of Pharmaceutical Scientists, Western Regional Meeting, South San Francisco, CA* (Abstract #F–22 and poster presented at the meeting) (Apr. 24–25, 1997).

Lam et al., "Pitfalls in Development of Multi–Dose Liquid Formulations for Three Protein Pharmaceuticals" *ACS National Meeting, New Orleans* (Abstract #137 and slides presented) (Mar. 24–28, 1996).

Li et al., "Aggregation and Precipitation of Human Relaxin Induced by Metal–Catalyzed Oxidation" *Biochemistry* 34(17):5762–5772 (1995).

Manning et al., "Stability of Protein Pharmaceuticals" *Pharm. Res.* 6(11):903–918 (1989).

Mileski et al., "Inhibition of CD18–dependent neutrophil adherence reduces organ injury after hemorrhagic shock in primates" *Surgery* 108:206–212 (1990).

Nielsen, et al., "Stability of Freeze Dried Horseradish Peroxidase Conjugated Monoclonal Antibodies Used in Diagnostic Serology" *Journal of Immunoassay* 16(2):183–197 (1995).

Novak et al., "The tolerance and safety of intravenously administered benzyl alcohol in methlprednisolone sodium succinate formulations in normal human subjects" *Toxicology and Applied Pharmacology* 23(1):54–61 (Sep. 1972).

Pearlman et al., "Analysis of Protein Drugs" *Peptide and Protein Drug Delivery*, Vincent H. L. Lee, Marcel Dekker, Inc., Chapter 6, pp. 247–301 (1991).

Picken et al., "Nucleotide sequence of the gene for heat–stable enterotoxin II of *Escherichia coli*" *Infection and Immunity* 42(1):269–275 (1983).

Pikal et al., "The Effects of Formulation Variables on the Stability of Freeze–Dried Human Growth Hormone" *Pharm. Res.* 8:427–436 (1991).

Pikal, M., "Freeze–Drying of Proteins, Part 2: Formulation Selection" *Biopharm.* 3(9):26–30 (1990).

Rao and Kroon, "Orthoclone OKT3: Chemical Mechanisms and Functional Effects of Degradation of a Therapeutic Monoclonal Antibody" *Stability and Characterization of Protein and Peptide Drugs: Case Histories*, John Wang and Rodney Pearlman, New York:Plenum Press pp. 135–158, chapter 4, (1993).

Reilly et al., "Oral delivery of antibodies: future pharmacokinetic trends" *Clin. Pharmocokinet.* 32(4):313–323 (1997).

Sapan, "Immunoglobulin stability" *Biotechnol. Appl. Biochem.* 25:9–12 (1997).

Scholtissek et al., "A cloning cartridge of $\lambda$ to terminator" *Nucl. Acids Res.* 15(7):3185 (1987).

Springer, T., "Adhesion receptors of the immune system" *Nature* 346:425–434 (1990).

Stoolman, L., "Adhesion molecules controlling lymphocyte migration" *Cell* 56:907–910 (1989).

Vedder et al., "A Monoclonal Antibody to the Adherence–promoting Leukocyte Glycoprotein, CD18, Reduces Organ Injury and Improves Survival from Hemorrhagic Shock and Resuscitation in Rabbits" *J. Clin. Invest.* 81:939–944 (1988).

Wang et al., "Parenteral Formulations of Proteins and Peptides: Stability and Stabilizers" *J. Parenteral Sci. Tech.* (Technical Report No. 10) 42(2S):S4–S26 (1988).

Yates, "Protein Structure Analysis by Mass Specrometry" *Methods in Enzymology* 271:351–377 (1996).

* cited by examiner

EVQLVESGGGLVQPGGSLRLSCATSGYTFTEYTMHWMRQAPGKGLEWVAGINPKNG
GTSHNQRFMDRFTISVDKSTSTAYMQMNSLRAEDTAVYYCARWRGLNYGFDVRYFD
VWGQGTLVTVSSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKKVEPKSCDK
THTCPPCPAPELLGGRMKQLEDKVEELLSKNYHLENEVARLKKLVGER

FIG. 1A

DIQMTQSPSSLSASVGDRVTITCRASQDINNYLNWYQQKPGKAPKLLIYYTSTLHSGVP
SRFSGSGSGTDYLTISSLQPEDFATYYCQQGNTLPPTFGQGTKVEIKRTVAAPSVFIFPP
SDEQLKSGTASVVCLLNNFYPREAKVQWKVDNALQSGNSQESVTEQDSKDSTYSLSST
LTLSKADYEKHKVYACEVTHQGLSSPVTKSFNRGEC

FIG. 1B

```
   1 GAATTCAACT TCTCCATACT TTGGATAAGG AAATACAGAC ATGAAAAATC TCATTGCTGA

61 GTTGTTATTT AAGCTTTGGA GATTATCGTC ACTGCAATGC TTCGCAATAT GGCGCAAAAT

121 GACCAACAGC GGTTGATTGA TCAGGTAGAG GGGGCGCTGT ACGAGGTAAA GCCCGATGCC

181 AGCATTCCTG ACGACGATAC GGAGCTGCTG CGCGATTACG TAAAGAAGTT ATTGAAGCAT

241 CCTCGTCAGT AAAAAGTTAA TCTTTTCAAC AGCTGTCATA AAGTTGTCAC GGCCGAGACT

301 TATAGTCGCT TTGTTTTTAT TTTTTAATGT ATTTGTAACT AGAATTCGAG CTCGCCGGGG

361 ATCCTCTAGA GGTTGAGGTG ATTTT ATG AAA AAG AAT ATC GCA TTT CTT CTT
 -23                                 M   K   K   N   I   A   F   L   L
```

| 413 | GCA | TCT | ATG | TTC | GTT | TTT | TCT | ATT | GCT | ACA | AAC | GCG | TAC | GCT | GAT | ATC |
|---|---|---|---|---|---|---|---|---|---|---|---|---|---|---|---|---|
| -14 | A | S | M | F | V | F | S | I | A | T | N | A | Y | A | D | I |

| 461 | CAG | ATG | ACC | CAG | TCC | CCG | AGC | TCC | CTG | TCC | GCC | TCT | GTG | GGC | GAT | AGG |
|---|---|---|---|---|---|---|---|---|---|---|---|---|---|---|---|---|
| 3 | Q | M | T | Q | S | P | S | S | L | S | A | S | V | G | D | R |

| 509 | GTC | ACC | ATC | ACC | TGT | CGT | GCC | AGT | CAG | GAC | ATC | AAC | AAT | TAT | CTG | AAC |
|---|---|---|---|---|---|---|---|---|---|---|---|---|---|---|---|---|
| 19 | V | T | I | T | C | R | A | S | Q | D | I | N | N | Y | L | N |

| 557 | TGG | TAT | CAA | CAG | AAA | CCA | GGA | AAA | GCT | CCG | AAA | CTA | CTG | ATT | TAC | TAT |
|---|---|---|---|---|---|---|---|---|---|---|---|---|---|---|---|---|
| 35 | W | Y | Q | Q | K | P | G | K | A | P | K | L | L | I | Y | Y |

| 605 | ACC | TCC | ACC | CTC | CAC | TCT | GGA | GTC | CCT | TCT | CGC | TTC | TCT | GGT | TCT | GGT |
|---|---|---|---|---|---|---|---|---|---|---|---|---|---|---|---|---|
| 51 | T | S | T | L | H | S | G | V | P | S | R | F | S | G | S | G |

| 653 | TCT | GGG | ACG | GAT | TAC | ACT | CTG | ACC | ATC | AGC | AGT | CTG | CAA | CCG | GAG | GAC |
|---|---|---|---|---|---|---|---|---|---|---|---|---|---|---|---|---|
| 67 | S | G | T | D | Y | T | L | T | I | S | S | L | Q | P | E | D |

| 701 | TTC | GCA | ACT | TAT | TAC | TGT | CAG | CAA | GGT | AAT | ACT | CTG | CCG | CCG | ACG | TTC |
|---|---|---|---|---|---|---|---|---|---|---|---|---|---|---|---|---|
| 83 | F | A | T | Y | Y | C | Q | Q | G | N | T | L | P | P | T | F |

| 749 | GGA | CAG | GGC | ACG | AAG | GTG | GAG | ATC | AAA | CGA | ACT | GTG | GCT | GCA | CCA | TCT |
|---|---|---|---|---|---|---|---|---|---|---|---|---|---|---|---|---|
| 99 | G | Q | G | T | K | V | E | I | K | R | T | V | A | A | P | S |

| 797 | GTC | TTC | ATC | TTC | CCG | CCA | TCT | GAT | GAG | CAG | TTG | AAA | TCT | GGA | ACT | GCC |
|---|---|---|---|---|---|---|---|---|---|---|---|---|---|---|---|---|
| 115 | V | F | I | F | P | P | S | D | E | Q | L | K | S | G | T | A |

| 845 | TCT | GTT | GTG | TGC | CTG | CTG | AAT | AAC | TTC | TAT | CCC | AGA | GAG | GCC | AAA | GTA |
|---|---|---|---|---|---|---|---|---|---|---|---|---|---|---|---|---|
| 131 | S | V | V | C | L | L | N | N | F | Y | P | R | E | A | K | V |

| 893 | CAG | TGG | AAG | GTG | GAT | AAC | GCC | CTC | CAA | TCG | GGT | AAC | TCC | CAG | GAG | AGT |
|---|---|---|---|---|---|---|---|---|---|---|---|---|---|---|---|---|
| 147 | Q | W | K | V | D | N | A | L | Q | S | G | N | S | Q | E | S |

| 941 | GTC | ACA | GAG | CAG | GAC | AGC | AAG | GAC | AGC | ACC | TAC | AGC | CTC | AGC | AGC | ACC |
|---|---|---|---|---|---|---|---|---|---|---|---|---|---|---|---|---|
| 163 | V | T | E | Q | D | S | K | D | S | T | Y | S | L | S | S | T |

| 989 | CTG | ACG | CTG | AGC | AAA | GCA | GAC | TAC | GAG | AAA | CAC | AAA | GTC | TAC | GCC | TGC |
|---|---|---|---|---|---|---|---|---|---|---|---|---|---|---|---|---|
| 179 | L | T | L | S | K | A | D | Y | E | K | H | K | V | Y | A | C |

| 1037 | GAA | GTC | ACC | CAT | CAG | GGC | CTG | AGC | TCG | CCC | GTC | ACA | AAG | AGC | TTC | AAC |
|---|---|---|---|---|---|---|---|---|---|---|---|---|---|---|---|---|
| 195 | E | V | T | H | Q | G | L | S | S | P | V | T | K | S | F | N |

| 1085 | AGG | GGA | GAG | TGT | TAA | G CTGATCCTCT ACGCCGGACG CATCGTGGCG |
|---|---|---|---|---|---|---|
| 211 | R | G | E | C | | |

FIG. 21A

```
1131 CTAGTACGCA AGTTCACGTA AAAACGGTAT CTAGAGGTTG AGGTGATTTT ATG AAA
 -23                                                         M   K

1187 AAG AAT ATC GCA TTT CTT CTT GCA TCT ATG TTC GTT TTT TCT ATT GCT
 -21 K   N   I   A   F   L   L   A   S   M   F   V   F   S   I   A

1235 ACA AAC GCG TAC GCT GAG GTT CAG CTG GTG GAG TCT GGC GGT GGC CTG
  -5 T   N   A   Y   A   E   V   Q   L   V   E   S   G   G   G   L

1283 GTG CAG CCA GGG GGC TCA CTC CGT TTG TCC TGT GCA ACT TCT GGC TAC
  12 V   Q   P   G   G   S   L   R   L   S   C   A   T   S   G   Y

1331 ACC TTT ACC GAA TAC ACT ATG CAC TGG ATG CGT CAG GCC CCG GGT AAG
  28 T   F   T   E   Y   T   M   H   W   M   R   Q   A   P   G   K

1379 GGC CTG GAA TGG GTT GCA GGG ATT AAT CCT AAA AAC GGT GGT ACC AGC
  44 G   L   E   W   V   A   G   I   N   P   K   N   G   G   T   S

1427 CAC AAC CAG AGG TTC ATG GAC CGT TTC ACT ATA AGC GTA GAT AAA TCC
  60 H   N   Q   R   F   M   D   R   F   T   I   S   V   D   K   S

1475 ACC AGT ACA GCC TAC ATG CAA ATG AAC AGC CTG CGT GCT GAG GAC ACT
  76 T   S   T   A   Y   M   Q   M   N   S   L   R   A   E   D   T

1523 GCC GTC TAT TAT TGT GCT AGA TGG CGA GGC CTG AAC TAC GGC TTT GAC
  92 A   V   Y   Y   C   A   R   W   R   G   L   N   Y   G   F   D

1571 GTC CGT TAT TTT GAC GTC TGG GGT CAA GGA ACC CTG GTC ACC GTC TCC
 108 V   R   Y   F   D   V   W   G   Q   G   T   L   V   T   V   S

1619 TCG GCC TCC ACC AAG GGC CCA TCG GTC TTC CCC CTG GCA CCC TCC TCC
 124 S   A   S   T   K   G   P   S   V   F   P   L   A   P   S   S

1667 AAG AGC ACC TCT GGG GGC ACA GCG GCC CTG GGC TGC CTG GTC AAG GAC
 140 K   S   T   S   G   G   T   A   A   L   G   C   L   V   K   D

1715 TAC TTC CCC GAA CCG GTG ACG GTG TCG TGG AAC TCA GGC GCC CTG ACC
 156 Y   F   P   E   P   V   T   V   S   W   N   S   G   A   L   T

1763 AGC GGC GTG CAC ACC TTC CCG GCT GTC CTA CAG TCC TCA GGA CTC TAC
 172 S   G   V   H   T   F   P   A   V   L   Q   S   S   G   L   Y

1811 TCC CTC AGC AGC GTG GTG ACC GTG CCC TCC AGC AGC TTG GGC ACC CAG
 188 S   L   S   S   V   V   T   V   P   S   S   S   L   G   T   Q

1859 ACC TAC ATC TGC AAC GTG AAT CAC AAG CCC AGC AAC ACC AAG GTC GAC
 204 T   Y   I   C   N   V   N   H   K   P   S   N   T   K   V   D

1907 AAG AAA GTT GAG CCC AAA TCT TGT GAC AAA ACT CAC ACA TGC CCG CCG
 220 K   K   V   E   P   K   S   C   D   K   T   H   T   C   P   P

1955 TGC CCA GCA CCA GAA CTG CTG GGC GGC CGC ATG AAA CAG CTA GAG GAC
 236 C   P   A   P   E   L   L   G   G   R   M   K   Q   L   E   D

2003 AAG GTC GAA GAG CTA CTC TCC AAG AAC TAC CAC CTA GAG AAT GAA GTG
 252 K   V   E   E   L   L   S   K   N   Y   H   L   E   N   E   V

2051 GCA AGA CTC AAA AAG CTT GTC GGG GAG CGC TAA  GCATGCG ACGGCCCTAG
 268 A   R   L   K   K   L   V   G   E   R

2101 AGTCCCTAAC GCTCGGTTGC CGCCGGGCGT TTTTTATTGT TAA
```

FIG. 21B

| Strain | Genotype |
|---|---|
| W3110 | K-12 F⁻ lambda⁻ IN*rrnD-rrnE1* |
| 1A2 | W3110 Δ*fhuA* |
| 7C1 | W3110 Δ*fhuA* Δ*phoA* Δ(*argF-lac*) |
| 16C9 | W3110 Δ*fhuA* Δ*phoA* Δ(*argF-lac*) *deoC* |
| 23E3 | W3110 Δ*fhuA* Δ*phoA* Δ(*argF-lac*) *deoC* Δ*degP* |
| 33B6 | W3110 Δ*fhuA* Δ*phoA* Δ(*argF-lac*) *deoC* Δ*degP ilvG* |
| 49B2 | W3110 Δ*fhuA* Δ*phoA* Δ(*argF-lac*) *deoC* Δ*degP ilvG* Δ*fucP* |
| 49A5 | W3110 Δ*fhuA* Δ*phoA* Δ(*argF-lac*) *deoC* Δ*degP ilvG* Δ*fucP* Δ*malE* |

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 241 amino acids
      (B) TYPE: Amino Acid
      (D) TOPOLOGY: Linear (xi) SEQUENCE DESCRIPTION: SEQ ID NO:1:

```
Glu Val Gln Leu Val Glu Ser Gly Gly Gly Leu Val Gln Pro Gly
 1               5                  10                  15

Gly Ser Leu Arg Leu Ser Cys Ala Thr Ser Gly Tyr Thr Phe Thr
                20                  25                  30

Glu Tyr Thr Met His Trp Met Arg Gln Ala Pro Gly Lys Gly Leu
                35                  40                  45

Glu Trp Val Ala Gly Ile Asn Pro Lys Asn Gly Gly Thr Ser His
                50                  55                  60

Asn Gln Arg Phe Met Asp Arg Phe Thr Ile Ser Val Asp Lys Ser
                65                  70                  75

Thr Ser Thr Ala Tyr Met Gln Met Asn Ser Leu Arg Ala Glu Asp
                80                  85                  90

Thr Ala Val Tyr Tyr Cys Ala Arg Trp Arg Gly Leu Asn Tyr Gly
                95                  100                 105
```

-continued

```
Phe Asp Val Arg Tyr Phe Asp Val Trp Gly Gln Gly Thr Leu Val
                110                 115                 120

Thr Val Ser Ser Ala Ser Thr Lys Gly Pro Ser Val Phe Pro Leu
                125                 130                 135

Ala Pro Ser Ser Lys Ser Thr Ser Gly Gly Thr Ala Ala Leu Gly
                140                 145                 150

Cys Leu Val Lys Asp Tyr Phe Pro Glu Pro Val Thr Val Ser Trp
                155                 160                 165

Asn Ser Gly Ala Leu Thr Ser Gly Val His Thr Phe Pro Ala Val
                170                 175                 180

Leu Gln Ser Ser Gly Leu Tyr Ser Leu Ser Ser Val Val Thr Val
                185                 190                 195

Pro Ser Ser Ser Leu Gly Thr Gln Thr Tyr Ile Cys Asn Val Asn
                200                 205                 210

His Lys Pro Ser Asn Thr Lys Val Asp Lys Lys Val Glu Pro Lys
                215                 220                 225

Ser Cys Asp Lys Thr His Thr Cys Pro Pro Cys Pro Ala Pro Glu
                230                 235                 240

Leu
241
```

(2) INFORMATION FOR SEQ ID NO:2:

(i) SEQUENCE CHARACTERISTICS:
        (A) LENGTH: 214 amino acids
        (B) TYPE: Amino Acid
        (D) TOPOLOGY: Linear (xi) SEQUENCE DESCRIPTION: SEQ ID NO:2:

```
Asp Ile Gln Met Thr Gln Ser Pro Ser Ser Leu Ser Ala Ser Val
 1                5                  10                  15

Gly Asp Arg Val Thr Ile Thr Cys Arg Ala Ser Gln Asp Ile Asn
                 20                  25                  30

Asn Tyr Leu Asn Trp Tyr Gln Gln Lys Pro Gly Lys Ala Pro Lys
                 35                  40                  45

Leu Leu Ile Tyr Tyr Thr Ser Thr Leu His Ser Gly Val Pro Ser
                 50                  55                  60

Arg Phe Ser Gly Ser Gly Ser Gly Thr Asp Tyr Thr Leu Thr Ile
                 65                  70                  75

Ser Ser Leu Gln Pro Glu Asp Phe Ala Thr Tyr Tyr Cys Gln Gln
                 80                  85                  90

Gly Asn Thr Leu Pro Pro Thr Phe Gly Gln Gly Thr Lys Val Glu
                 95                 100                 105

Ile Lys Arg Thr Val Ala Ala Pro Ser Val Phe Ile Phe Pro Pro
                110                 115                 120

Ser Asp Glu Gln Leu Lys Ser Gly Thr Ala Ser Val Val Cys Leu
                125                 130                 135

Leu Asn Asn Phe Tyr Pro Arg Glu Ala Lys Val Gln Trp Lys Val
                140                 145                 150

Asp Asn Ala Leu Gln Ser Gly Asn Ser Gln Glu Ser Val Thr Glu
                155                 160                 165

Gln Asp Ser Lys Asp Ser Thr Tyr Ser Leu Ser Ser Thr Leu Thr
                170                 175                 180

Leu Ser Lys Ala Asp Tyr Glu Lys His Lys Val Tyr Ala Cys Glu
                185                 190                 195
```

```
Val Thr His Gln Gly Leu Ser Ser Pro Val Thr Lys Ser Phe Asn
                200                 205                 210
Arg Gly Glu Cys
            214
```

(2) INFORMATION FOR SEQ ID NO:3:

(i) SEQUENCE CHARACTERISTICS:
        (A) LENGTH: 36 amino acids
        (B) TYPE: Amino Acid
        (D) TOPOLOGY: Linear (xi) SEQUENCE DESCRIPTION: SEQ ID NO:3:

```
Leu Gly Gly Arg Met Lys Gln Leu Glu Asp Lys Val Glu Glu Leu
 1               5                  10                  15
Leu Ser Lys Asn Tyr His Leu Glu Asn Glu Val Ala Arg Leu Lys
                20                  25                  30
Lys Leu Val Gly Glu Arg
                35  36
```

(2) INFORMATION FOR SEQ ID NO:4:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO:4:

```
Pro Lys Asn Ser Ser Met Ile Ser Asn Thr Pro
 1               5                  10  11
```

(2) INFORMATION FOR SEQ ID NO:5:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:5:

```
His Gln Ser Leu Gly Thr Gln
 1               5       7
```

(2) INFORMATION FOR SEQ ID NO:6:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:6:

```
His Gln Asn Leu Ser Asp Gly Lys
 1               5           8
```

(2) INFORMATION FOR SEQ ID NO:7:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:7:

```
His Gln Asn Ile Ser Asp Gly Lys
 1               5           8
```

(2) INFORMATION FOR SEQ ID NO:8:

(i) SEQUENCE CHARACTERISTICS:
            (A) LENGTH: 8 amino acids
            (B) TYPE: Amino Acid
            (D) TOPOLOGY: Linear (xi) SEQUENCE DESCRIPTION: SEQ ID NO:8:

Val Ile Ser Ser His Leu Gly Gln
 1               5               8

(2) INFORMATION FOR SEQ ID NO:9:

(i) SEQUENCE CHARACTERISTICS:
            (A) LENGTH: 2143 base pairs
            (B) TYPE: Nucleic Acid
            (C) STRANDEDNESS: Single
            (D) TOPOLOGY: Linear (xi) SEQUENCE DESCRIPTION: SEQ ID NO:9:

| | |
|---|---:|
| GAATTCAACT TCTCCATACT TTGGATAAGG AAATACAGAC ATGAAAAATC | 50 |
| TCATTGCTGA GTTGTTATTT AAGCTTTGGA GATTATCGTC ACTGCAATGC | 100 |
| TTCGCAATAT GGCGCAAAAT GACCAACAGC GGTTGATTGA TCAGGTAGAG | 150 |
| GGGGCGCTGT ACGAGGTAAA GCCCGATGCC AGCATTCCTG ACGACGATAC | 200 |
| GGAGCTGCTG CGCGATTACG TAAAGAAGTT ATTGAAGCAT CCTCGTCAGT | 250 |
| AAAAAGTTAA TCTTTTCAAC AGCTGTCATA AAGTTGTCAC GGCCGAGACT | 300 |
| TATAGTCGCT TTGTTTTTAT TTTTTAATGT ATTTGTAACT AGAATTCGAG | 350 |
| CTCGCCGGGG ATCCTCTAGA GGTTGAGGTG ATTTTATGAA AAAGAATATC | 400 |
| GCATTTCTTC TTGCATCTAT GTTCGTTTTT TCTATTGCTA CAAACGCGTA | 450 |
| CGCTGATATC CAGATGACCC AGTCCCCGAG CTCCCTGTCC GCCTCTGTGG | 500 |
| GCGATAGGGT CACCATCACC TGTCGTGCCA GTCAGGACAT CAACAATTAT | 550 |
| CTGAACTGGT ATCAACAGAA ACCAGGAAAA GCTCCGAAAC TACTGATTTA | 600 |
| CTATACCTCC ACCCTCCACT CTGGAGTCCC TTCTCGCTTC TCTGGTTCTG | 650 |
| GTTCTGGGAC GGATTACACT CTGACCATCA GCAGTCTGCA ACCGGAGGAC | 700 |
| TTCGCAACTT ATTACTGTCA GCAAGGTAAT ACTCTGCCGC CGACGTTCGG | 750 |
| ACAGGGCACG AAGGTGGAGA TCAAACGAAC TGTGGCTGCA CCATCTGTCT | 800 |
| TCATCTTCCC GCCATCTGAT GAGCAGTTGA AATCTGGAAC TGCCTCTGTT | 850 |
| GTGTGCCTGC TGAATAACTT CTATCCCAGA GAGGCCAAAG TACAGTGGAA | 900 |
| GGTGGATAAC GCCCTCCAAT CGGGTAACTC CCAGGAGAGT GTCACAGAGC | 950 |
| AGGACAGCAA GGACAGCACC TACAGCCTCA GCAGCACCCT GACGCTGAGC | 1000 |
| AAAGCAGACT ACGAGAAACA CAAAGTCTAC GCCTGCGAAG TCACCCATCA | 1050 |
| GGGCCTGAGC TCGCCCGTCA CAAAGAGCTT CAACAGGGGA GAGTGTTAAG | 1100 |
| CTGATCCTCT ACGCCGGACG CATCGTGGCG CTAGTACGCA AGTTCACGTA | 1150 |
| AAAACGGTAT CTAGAGGTTG AGGTGATTTT ATGAAAAAGA ATATCGCATT | 1200 |
| TCTTCTTGCA TCTATGTTCG TTTTTTCTAT TGCTACAAAC GCGTACGCTG | 1250 |
| AGGTTCAGCT GGTGGAGTCT GGCGGTGGCC TGGTGCAGCC AGGGGGCTCA | 1300 |
| CTCCGTTTGT CCTGTGCAAC TTCTGGCTAC ACCTTTACCG AATACACTAT | 1350 |
| GCACTGGATG CGTCAGGCCC CGGGTAAGGG CCTGGAATGG GTTGCAGGGA | 1400 |
| TTAATCCTAA AAACGGTGGT ACCAGCCACA ACCAGAGGTT CATGGACCGT | 1450 |

```
TTCACTATAA GCGTAGATAA ATCCACCAGT ACAGCCTACA TGCAAATGAA      1500

CAGCCTGCGT GCTGAGGACA CTGCCGTCTA TTATTGTGCT AGATGGCGAG      1550

GCCTGAACTA CGGCTTTGAC GTCCGTTATT TTGACGTCTG GGGTCAAGGA      1600

ACCCTGGTCA CCGTCTCCTC GGCCTCCACC AAGGGCCCAT CGGTCTTCCC      1650

CCTGGCACCC TCCTCCAAGA GCACCTCTGG GGGCACAGCG GCCCTGGGCT      1700

GCCTGGTCAA GGACTACTTC CCCGAACCGG TGACGGTGTC GTGGAACTCA      1750

GGCGCCCTGA CCAGCGGCGT GCACACCTTC CCGGCTGTCC TACAGTCCTC      1800

AGGACTCTAC TCCCTCAGCA GCGTGGTGAC CGTGCCCTCC AGCAGCTTGG      1850

GCACCCAGAC CTACATCTGC AACGTGAATC ACAAGCCCAG CAACACCAAG      1900

GTCGACAAGA AAGTTGAGCC CAAATCTTGT GACAAAACTC ACACATGCCC      1950

GCCGTGCCCA GCACCAGAAC TGCTGGGCGG CCGCATGAAA CAGCTAGAGG      2000

ACAAGGTCGA AGAGCTACTC TCCAAGAACT ACCACCTAGA GAATGAAGTG      2050

GCAAGACTCA AAAAGCTTGT CGGGGAGCGC TAAGCATGCG ACGGCCCTAG      2100

AGTCCCTAAC GCTCGGTTGC CGCCGGGCGT TTTTTATTGT TAA             2143

(2) INFORMATION FOR SEQ ID NO:10:

(i) SEQUENCE CHARACTERISTICS:
        (A) LENGTH: 237 amino acids
        (B) TYPE: Amino Acid
        (D) TOPOLOGY: Linear (xi) SEQUENCE DESCRIPTION: SEQ ID NO:10:

Met Lys Lys Asn Ile Ala Phe Leu Leu Ala Ser Met Phe Val Phe
-23         -20                 -15                 -10

Ser Ile Ala Thr Asn Ala Tyr Ala Asp Ile Gln Met Thr Gln Ser
            -5                  1                5

Pro Ser Ser Leu Ser Ala Ser Val Gly Asp Arg Val Thr Ile Thr
        10                  15                  20

Cys Arg Ala Ser Gln Asp Ile Asn Asn Tyr Leu Asn Trp Tyr Gln
        25                  30                  35

Gln Lys Pro Gly Lys Ala Pro Lys Leu Leu Ile Tyr Tyr Thr Ser
        40                  45                  50

Thr Leu His Ser Gly Val Pro Ser Arg Phe Ser Gly Ser Gly Ser
        55                  60                  65

Gly Thr Asp Tyr Thr Leu Thr Ile Ser Ser Leu Gln Pro Glu Asp
        70                  75                  80

Phe Ala Thr Tyr Tyr Cys Gln Gln Gly Asn Thr Leu Pro Pro Thr
        85                  90                  95

Phe Gly Gln Gly Thr Lys Val Glu Ile Lys Arg Thr Val Ala Ala
        100                 105                 110

Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly
        145                 150                 155

Asn Ser Gln Glu Ser Val Thr Glu Gln Asp Ser Lys Asp Ser Thr
        160                 165                 170

Tyr Ser Leu Ser Ser Thr Leu Thr Leu Ser Lys Ala Asp Tyr Glu
```

```
                175                 180                 185
Lys His Lys Val Tyr Ala Cys Glu Val Thr His Gln Gly Leu Ser
            190                 195                 200

Ser Pro Val Thr Lys Ser Phe Asn Arg Gly Glu Cys
            205                 210         214

(2) INFORMATION FOR SEQ ID NO:11:

(i) SEQUENCE CHARACTERISTICS:
        (A) LENGTH: 300 amino acids
        (B) TYPE: Amino Acid
        (D) TOPOLOGY: Linear (xi) SEQUENCE DESCRIPTION: SEQ ID NO:11:

Met Lys Lys Asn Ile Ala Phe Leu Leu Ala Ser Met Phe Val Phe
-23         -20             -15                 -10

Ser Ile Ala Thr Asn Ala Tyr Ala Glu Val Gln Leu Val Glu Ser
             -5              1               5

Gly Gly Gly Leu Val Gln Pro Gly Gly Ser Leu Arg Leu Ser Cys
             10              15              20

Ala Thr Ser Gly Tyr Thr Phe Thr Glu Tyr Thr Met His Trp Met
             25              30              35

Arg Gln Ala Pro Gly Lys Gly Leu Glu Trp Val Ala Gly Ile Asn
             40              45              50

Pro Lys Asn Gly Gly Thr Ser His Asn Gln Arg Phe Met Asp Arg
             55              60              65

Phe Thr Ile Ser Val Asp Lys Ser Thr Ser Thr Ala Tyr Met Gln
             70              75              80

Met Asn Ser Leu Arg Ala Glu Asp Thr Ala Val Tyr Tyr Cys Ala
             85              90              95

Arg Trp Arg Gly Leu Asn Tyr Gly Phe Asp Val Arg Tyr Phe Asp
             100             105             110

Val Trp Gly Gln Gly Thr Leu Val Thr Val Ser Ser Ala Ser Thr
             115             120             125

Lys Gly Pro Ser Val Phe Pro Leu Ala Pro Ser Ser Lys Ser Thr
             130             135             140

Ser Gly Gly Thr Ala Ala Leu Gly Cys Leu Val Lys Asp Tyr Phe
             145             150             155

Pro Glu Pro Val Thr Val Ser Trp Asn Ser Gly Ala Leu Thr Ser
             160             165             170

Gly Val His Thr Phe Pro Ala Val Leu Gln Ser Ser Gly Leu Tyr
             175             180             185

Ser Leu Ser Ser Val Val Thr Val Pro Ser Ser Ser Leu Gly Thr
             190             195             200

Gln Thr Tyr Ile Cys Asn Val Asn His Lys Pro Ser Asn Thr Lys
             205             210             215

Val Asp Lys Lys Val Glu Pro Lys Ser Cys Asp Lys Thr His Thr
             220             225             230

Cys Pro Pro Cys Pro Ala Pro Glu Leu Leu Gly Gly Arg Met Lys
             235             240             245

Gln Leu Glu Asp Lys Val Glu Leu Leu Ser Lys Asn Tyr His
             250             255             260

Leu Glu Asn Glu Val Ala Arg Leu Lys Lys Leu Val Gly Glu Arg
             265             270             275     277
```

ANTIBODY FORMULATION

RELATED APPLICATION

This is a non-provisional application claiming priority under Section 119(e) to provisional application 60/053,087, filed on Jun. 13, 1997, the contents of which are incorporated herein by reference.

FIELD OF THE INVENTION

This invention is directed to a stable aqueous pharmaceutical formulation comprising an antibody.

BACKGROUND OF THE INVENTION

In the past ten years, advances in biotechnology have made it possible to produce a variety of proteins for pharmaceutical applications using recombinant DNA techniques. Because proteins are larger and more complex than traditional organic and inorganic drugs (i.e. possessing multiple functional groups in addition to complex three-dimensional structures), the formulation of such proteins poses special problems. For a protein to remain biologically active, a formulation must preserve intact the conformational integrity of at least a core sequence of the protein's amino acids while at the same time protecting the protein's multple functional groups from degradation. Degradation pathways for proteins can involve chemical instability (i.e. any process which involves modification of the protein by bond formation or cleavage resulting in a new chemical entity) or physical instability (i.e. changes in the higher order structure of the protein). Chemical instability can result from deamidation, racemization, hydrolysis, oxidation, beta elimination or disulfide exchange. Physical instability can result from denaturation, aggregation, precipitation or adsorption, for example. The three most common protein degradation pathways are protein aggregation, deamidation and oxidation. Cleland et al *Critical Reviews in Therapeutic Drug Carrier Systems* 10(4): 307–377 (1993).

Included in the proteins used for pharmaceutical applications are antibodies. An example of an antibody useful for therapy is an antibody which binds to the CD18 antigen. CD18 is the common β subunit of three heterodimeric membrane integrins restricted to leukocytes that mediate trafficking and adhesion to the vascular endothelium, particularly at sites of inflammation (for reviews see Hynes, R. O. *Cell*, 69:11–25 (1992); Stoolman, *Cell*, 56:907–910 (1989); Jutila et al. *Transplantation* 48(5): 727–731 (1989); Springer, T. A., *Nature* 346:425–434 (1990); and Albelda and Buck, *FASEB J.* 4:2868–2880 (1990)). The heterodimer containing CD18 and CD11b (also called MAC-1) is found primarily on neutrophils, monocytes, and some lymphocytes whose normal interaction with ICAM-1 on vascular endothelium mediates adhesion and "rolling" of cells along the vasculature. In severe hemorrhagic trauma with concurrent decrease in cardiac output and ischemia, early (within 30 min) neutrophil activation (in response to released cytokines) and up-regulation of MAC-1 increases neutrophil "stickiness". This precedes extravasation and release of proteases and superoxides that ultimately lead to further tissue damage and increased vascular permeability (Hernandez et al, *Am. J. Physiol.*, 253(3 Pt 2): H699-H703 (1987)). Reperfusion following resuscitation exacerbates the edema and necrosis, and leads to multi-organ failure and death. Early treatment with monoclonal antibodies to CD18 in a partally-severed, ischemic rabbit ear trauma model alleviated tissue necrosis following reattachment (Vedder et al., *J. Clin. Invest.* 81:939–944 (1988)). A humanized antibody showed efficacy in reducing multi-organ damage and death in a rhesus monkey model of decreased cardiac output (created by depletion of ⅔ of blood volume for ~2 hours (Mileski et al., *Surgery*, 108(2):206–212 (1990)). These studies point to the therapeutic potential of anti-CD18 antibodies for acute treatment of hemorrhagic shock.

Another antigen of interest for targeting with antibodies is the CD20 antigen, also known as "Bp35". CD20 is a human B cell marker which is expressed during early pre-B cell development and remains until plasma cell differentiation. The CD20 molecule may regulate a step in the activation process which is required for cell cycle initiation and differentiation and is usually expressed at very high levels on neoplastic B cells. Thus, the CD20 surface antigen can be targeted for treating B cell lymphomas. U.S. Pat. No. 5,736,137 issued Apr. 7, 1998 describes the chimeric antibody "C2B8" which binds the CD20 antigen and its use to treat B cell lymphoma.

There is a need in the art for a stable aqueous pharmaceutical formulation comprising an antibody, such as an anti-CD18 or anti-CD20 antibody, which is suitable for therapeutic use.

SUMMARY OF THE INVENTION

Accordingly, the invention provides a stable aqueous pharmaceutical formulation comprising a therapeutically effective amount of an antibody not subjected to prior lyophilizabon, a buffer maintaining the pH in the range from about 4.5 to about 6.0, a surfactant and a polyol. Preferably the formulation is stable at a temperature of about 2–8° C. for at least one year, and/or is stable at a temperature of about 30° C. for at least one month and/or is stable following freezing and thawing of the formulation.

The invention also relates to an article of manufacture comprising a container holding a stable aqueous pharmaceutical formulation comprising a therapeutically effective amount of an antibody not subjected to prior lyophilizabon, a buffer maintaining the pH in the range from about 4.5 to about 6.0, a surfactant and a polyol.

In yet a further aspect, the invention relates to a method for stabilizing an antibody in an aqueous pharmaceutical formulation by combining a therapeutically effective amount of an antibody not subjected to prior lyophilization, a buffer maintaining the pH in the range from about 4.5 to about 6.0, a surfactant and a polyol.

In a still further aspect, the invention concerns a method of treating a mammal comprising administering a therapeutically effective amount of the aqueous pharmaceutical formulation disclosed herein to a mammal, wherein the mammal has a disorder requiring treatment with the antibody in the formulation. Where the antibody binds CD18, examples of disorders to be treated include hemorrhagic shock, thermal injury (such as that resulting from burns), stroke (including ischemic and hemorrhagic stroke) and myocardial infarction. For an anti-IL8 antibody, disorders to be treated include inflammatory disorders such as adult respiratory distress syndrome (ARDS), hypovolemic shock, ulcerative colitis, and rheumatoid arthritis. Where the antibody binds CD20, disorders to be treated include B cell lymphomas.

These and further aspects of the invention will be apparent to those skilled in the art.

BRIEF DESCRIPTION OF THE DRAWINGS

FIGS. 1A and 1B depict the amino acid sequence of rhuMAb CD18 heavy chain (FIG. 1A; SEQ ID NO:1) and light chain (FIG. 1B; SEQ ID NO:2). The sequence in italics in FIG. 1A (SEQ ID NO:3) is that of the leucine zipper.

FIG. 10 depicts the effect of storage temperature on the stability of rhuMAb CD18 (5 week data) assayed by HIC showing total peak area recovered. A trend towards loss in area was noted in all formulations with increasing storage temperatures, except for F5 which started lower to begin with.

In FIG. 19C, specific activity was the ratio of MAC-1 binding to total F(ab')$_2$ ELISA. Samples are stable at 5° C. and 15° C. up to 43 weeks and at 30° C. up to 1 month. Analyses were made at the time points indicated.

FIGS. 21A and 21B depict the full nucleotide sequence (SEQ ID NO:9) and encoded amino acid sequences (SEQ ID No's:10 and 11, respectively) of the pS 1130 expression cassette.

FIG. 22 shows derivation of the 49A5 production cell line.

1 mole rhuMAb CD20 (67 mM trehalose); 3=500 moles trehalose: 1 mole rhuMAb CD20 (134 mM trehalose); and 4=1000 moles trehalose: 1 mole rhuMAb CD20 (267 mM trehalose).

Figure 26:
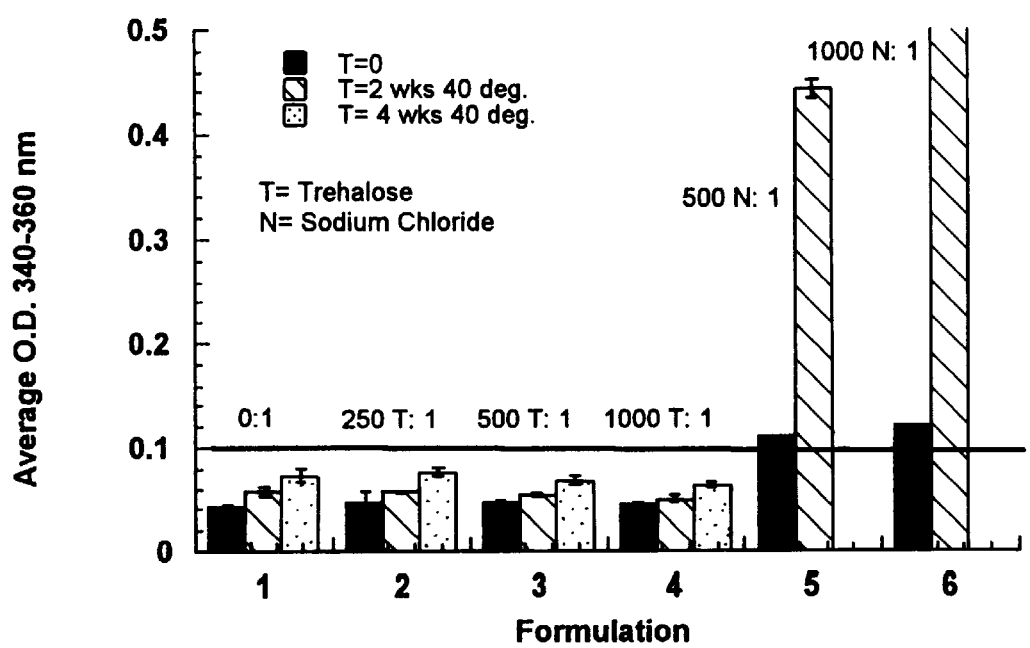

FIG. 26 shows the effect of excess molar ratios of trehalose or sodium chloride on the clarity of rhuMAb CD20 multdose formulations stored at 40° C. for up to four weeks. The composition of the formulations is 40 mg/mL rhuMAb CD20,20 mM acetate, 0 to 1000:1 molar ratio of trehalose or sodium chloride, 0.9% benzyl alcohol and 0.02% polysorbate 20 at pH 5.0. The clarity of the 500:1 and 1000:1 molar ratio of sodium chloride to rhuMAb CD20 formulations was not measured after four weeks at 40° C. due to the physical appearance of these formulations. The 500:1 ratio formulation was very opalescent while the 1000:1 ratio formulabon had separated into two phases composed of a thin opaque gel layer covered with an opalescent fluid. The O.D. of the 1000:1 molar ratio of sodium chloride to rhuMAb CD20 formulation was 2.72 after two weeks storage at 40° C.

Figure 27:
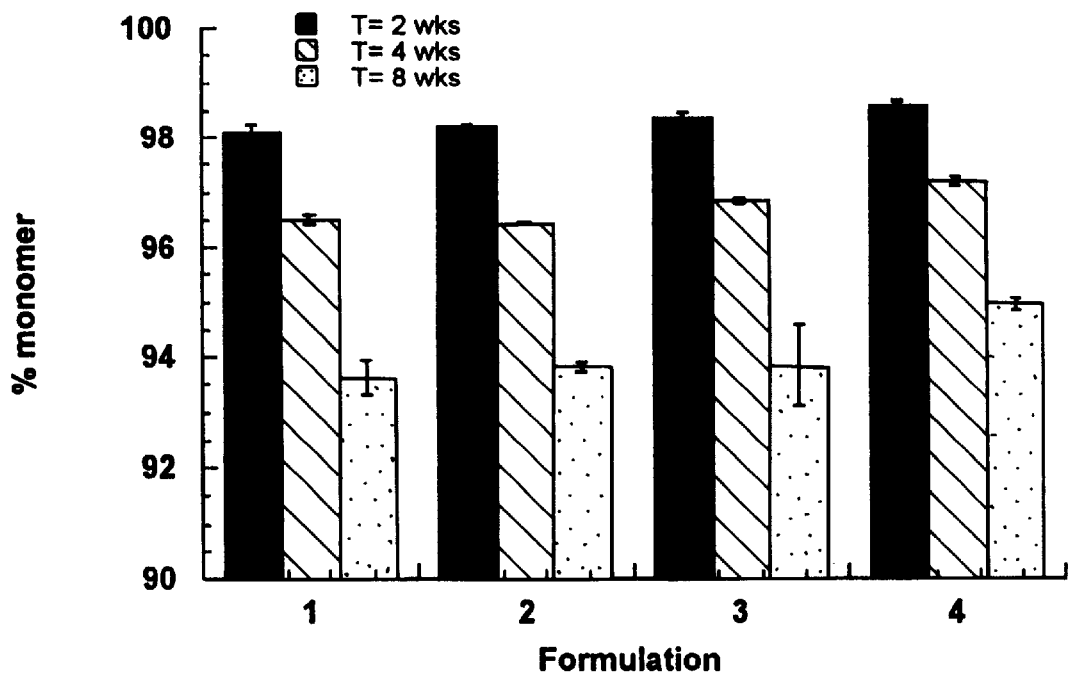

FIG. 27 depicts the effect of excess molar ratios of trehalose on the stability of rhuMAb CD20 muffidose formulations stored at 40° C. as analyzed by SEC HPLC. The composition of the formulations is 40 mg/mL rhuMAb CD20, 20 mM acetate, 0–267 mM trehalose, 0.9% benzyl alcohol and 0.02% polysorbate 20 at pH 5.0. The amount of trehalose in formulations 1–4 was as follows: 1=0 moles trehalose: 1 mole of rhuMAb CD20 (0 mM trehalose); 2=250 moles trehalose: 1 mole rhuMAb CD20 (67 mM trehalose); 3=500 moles trehalose: 1 mole rhuMAb CD20 (134 mM trehalose); and 4=1000 moles trehalose: 1 mole rhuMAb CD20 (267 mM trehalose). The percent monomer at each bmepoint was normalized to the percent monomer at T=0.

Figure 28:
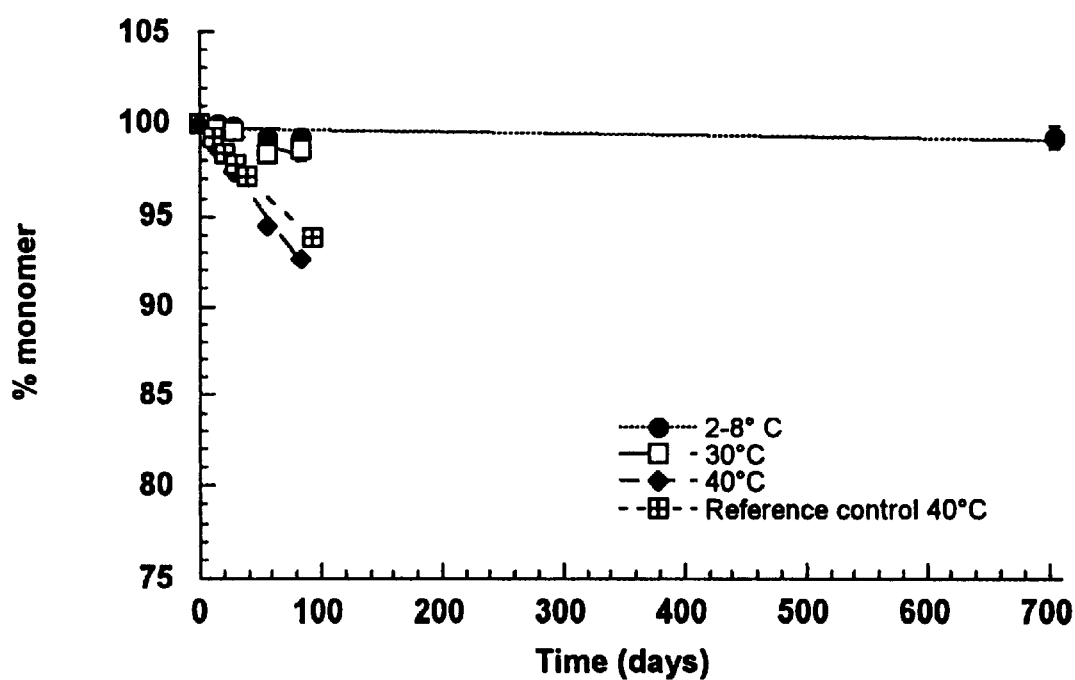

FIG. 28 shows the stability profile of the prototype liquid rhuMAb CD20 multidose formulation stored at 2–8° C. for up to two years as measured by SEC HPLC. The formulation was composed of 40 mg/mL rhuMAb CD20, 150 mM trehalose, 0.9% benzyl alcohol and 0.02% polysorbate 20 at pH 5.0. The percent monomer at each timepoint was normalized to the percent monomer at T=0. The bioactivity of the formulation stored at 2–8° C. for two years was 99.2% relative to the reference control as measured by the CDC assay.

DETAILED DESCRIPTION OF THE PREFERRED EMBODIMENTS

I. Definitions

The term "pharmaceutical formulation" refers to preparations which are in such form as to permit the biological actvity of the active ingredients to be unequivocally effective, and which contain no additional components which are toxic to the subjects to which the formulation would be administered. "Pharmaceutically acceptable" excipients (vehicles, additives) are those which can reasonably be administered to a subject mammal to provide an effective dose of the active ingredient employed.

A "stable" formulation is one in which the protein therein essentially retains its physical stability and/or chemical stability and/or biological activity upon storage. Various analytical techniques for measuring protein stability are available in the art and are reviewed in *Peptide and Protein Drug Delivery*, 247–301, Vincent Lee Ed., Marcel Dekker, Inc., New York, N.Y., Pubs. (1991) and Jones, A. *Adv. Drug Delivery Rev*. 10: 29–90 (1993), for example. Stability can be measured at a selected temperature for a selected time period. Preferably, the formulation is stable at room temperature (~30° C.) or at 40° C. for at least 1 month and/or stable at about 2–8° C. for at least 1 year for at least 2 years. Furthermore, the formulation is preferably stable following freezing (to, e.g., −70° C.) and thawing of the formulation.

A protein "retains its physical stability" in a pharmaceutical formulation if it shows no signs of aggregation, precipitation and/or denaturation upon visual examination of color and/or clarity, or as measured by UV light scattering or by size exclusion chromatography.

A protein "retains its chemical stability" in a pharmaceutical formulation, if the chemical stability at a given time is such that the protein is considered to still retain its biological activity as defined below. Chemical stability can be assessed by detecting and quantifying chemically altered forms of the protein. Chemical alteration may involve size modification (e.g. clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography, for example.

An antibody "retains its biological activity" in a pharmaceutical formulation, if the biological activity of the antibody at a given time is within about 10% (within the errors of the assay) of the biological activity exhibited at the time the pharmaceutical formulation was prepared as determined in an antigen binding assay, for example. Other "biological activity" assays for antibodies are elaborated hereinbelow.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

A "polyol" is a substance with multiple hydroxyl groups, and includes sugars (reducing and nonreducing sugars), sugar alcohols and sugar acids. Preferred polyols herein have a molecular weight which is less than about 600 kD (e.g. in the range from about 120 to about 400 kD). A "reducing sugar" is one which contains a hemiacetal group that can reduce metal ions or react covalently with lysine and other amino groups in proteins and a "nonreducing sugar" is one which does not have these properties of a reducing sugar. Examples of reducing sugars are fructose, mannose, maltose, lactose, arabinose, xylose, ribose, rhamnose, galactose and glucose. Nonreducing sugars include sucrose, trehalose, sorbose, melezitose and raffinose. Mannitol, xylitol, erythritol, threitol, sorbitol and glycerol are examples of sugar alcohols. As to sugar acids, these include L-gluconate and metallic salts thereof. Where it desired that the formulation is freeze-thaw stable, the polyol is preferably one which does not crystallize at freezing temperatures (e.g. −20° C.) such that it destabilizes the antibody in the formulation. Nonreducing sugars such as sucrose and trehalose are the preferred polyols herein, with trehalose being preferred over sucrose, because of the superior solution stability of trehalose.

As used herein, "buffer" refers to a buffered solution that resists changes in pH by the action of its acid-base conjugate components. The buffer of this invention has a pH in the range from about 4.5 to about 6.0; preferably from about 4.8 to about 5.5; and most preferably has a pH of about 5.0. Examples of buffers that will control the pH in this range include acetate (e.g. sodium acetate), succinate (such as sodium succinate), gluconate, histidine, citrate and other organic acid buffers. Where a freeze-thaw stable formulation is desired, the buffer is preferably not phosphate.

In a pharmacological sense, in the context of the present invention, a "therapeutically effective amount" of an antibody refers to an amount effective in the prevention or treatment of a disorder for the treatment of which the antibody is effective. A "disorder" is any condition that would benefit from treatment with the antibody. This includes chronic and acute disorders or diseases including those pathological conditions which predispose the mammal to the disorder in question.

A "preservative" is a compound which can be included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

As used herein, the term "inflammatory disorders" refers to pathological states resulting in inflammation, e.g. caused by influx of leukocytes and/or neutrophil chemotaxis. Inflammation may result from infection with pathogenic organisms and viruses and noninfectious means such as trauma or reperfusion following myocardial infarction or stroke, immune response to foreign antigen and autoimmune responses. Examples of inflammatory disorders include inflammatory skin diseases such as psoriasis and dermatitis; responses associated with inflammatory bowel disease (such as Crohn's disease and ulcerative colitis); ischemic reperfusion; adult respiratory distress syndrome; meningitis; encephalitis; uvei.s; autoimmune diseases such as rheumatoid arthritis, Sjorgen's syndrome, vasculitis; diseases involving leukocyte diapedesis; central nervous system (CNS) inflammatory disorder; multiple organ injury syndrome secondary to septcaemia or trauma; alcoholic hepatitis; bacterial pneumonia; antigen-antibody complex mediated diseases; hypovolemic shock; glomerulonephritis; multiple sclerosis; Type I diabetes melitis; acute and delayed hypersensitivity; graft vs. host disease; transplant rejection; reperfusion injury; endotoxic shock; disease states due to leukocyte dyscrasia and metastasis; asthma; pulmonary oxygen toxicity; inflammation of the lung, including pleurisy, alveolitis, vasculitis, pneumonia, chronic bronchitis, bronchiectasis, and cystic fibrosis; etc.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antgenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is notto be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al, *Nature* 352:624–628 (1991) and Marks et al., *J. Mol. Biol.* 222:581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. NatL. Acad Sci. USA* 81:6851–6855 (1984)).

The term "hypervariable region" when used herein refers to the amino acid residues of an antibody which are responsible for antigen-binding. The hypervariable region comprises amino acid residues from a "complementarity determining region" or "CDR" (i.e. residues 24–34 (L1), 50–56 (L2) and 89–97 (L3) in the light chain variable domain and 31–35 (H1), 50–65 (H2) and 95–102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop"(i.e. residues 26–32 (L1), 50–52 (L2) and 91–96 (L3) in the light chaiin variable domain and 26–32 (H1), 53–55 (H2) and 96–101 (H3) in the heavy chain variable domain; Chothia Lesk *J. Mol. Biol.* 196:901–917 (1987)). "Framework" or "FR" residues are those variable domain residues other than the hypervariable region residues as herein defined. The CDR and FR residues of the H52 antibody of the example below are identified in Eigenbrot et al. *Proteins: Structure, Function and Genetics* 18:49–62 (1994).

"Humanized" forms of non-human (e.g., murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, FR residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., *Nature* 321:522–525 (1986); Riechmann et al, *Nature* 332:323–329 (1988); and Presta, *Curr. Op. Struct. Biol.* 2:593–596 (1992).

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol.113, Rosenburg and Moore eds. Springer-Verlag, New York, pp. 269–315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$–$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al, *Proc. Natl. Acad. Sci. USA* 90:6444–6448 (1993).

The expression "linear antibodies" when used throughout this application refers to the antibodies described in Zapata et al. *Protein Eng.* 8(10):1057–1062 (1995). Briefly, these antibodies comprise a pair of tandem Fd segments ($V_H$–$C_H$1–$V_H$–$C_H$1) which form a pair of antigen binding regions. Linear antibodies can be bispecific or monospecific.

The antibody which is formulated is preferably essentially pure and desirably essentially homogeneous (i.e. free from contaminating proteins etc). "Essentially pure" antibody means a composition comprising at least about 90% by weight of the antibody, based on total weight of the composition, preferably at least about 95% by weight. "Essentially homogeneous" antibody means a composition comprising at least about 99% by weight of antibody, based on total weight of the composition.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

II. Modes for Carrying Out the Invention

The invention herein relates to a stable aqueous formulation comprising an antibody. The antibody in the formulation is prepared using techniques available in the art for generating antibodies, exemplary methods of which are described in more detail in the following sections.

The antibody is directed against an antigen of interest. Preferably, the antigen is a biologically important polypeptde and administration of the antibody to a mammal suffering from a disorder can result in a therapeutic benefit in that mammal. However, antibodies directed against non-polypeptide antigens (such as tumor-associated glycolipid antigens; see U.S. Pat. No. 5,091,178) are also contemplated.

Where the antigen is a polypeptide, it may be a transmembrane molecule (e.g. receptor) or ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tssue factor, and von Willebrands factor; anti-clotting factors such as Protein C; atrial natriuretic factor; lung surfactant; a plasminogen activator, such as urokinase or human urine or tssue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1–3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrns such as CD11a, CD11b, CD11c, CD18, an ICAM, VLA-4 and VCAM; a tumor associated antigen such as HER2, HER3 or HER4 receptor; and fragments of any of the above-listed polypeptides.

Preferred molecular targets for antibodies encompassed by the present invention include CD proteins such as CD3, CD4, CD8, CD19, CD20 and CD34; members of the ErbB receptor family such as the EGF receptor, HER2, HER3 or HER4 receptor; cell adhesion molecules such as LFA-1, Mac1, p150,95, VLA-4, ICAM-1, VCAM and αv/β3 integrin including either α or β subunits thereof (e.g. anti-CD11a, anti-CD18or anti-CD11b antibodies); growth factors such as VEGF; an interleukin such as IL8; IgE; blood group antigens; flk2/flt3 receptor; obesity (OB) receptor; mpl receptor; CTLA-4; protein C etc.

The preferred antibody herein is one which binds to human CD18 and preferably blocks (partially or completely) the ability of a cell (e.g. a neutrophil) expressing the CD18 subunit at its cell surface to bind to endothelium. Examples of anti-CD18 antibodies include MHM23 (Hildreth et al., *Eur. J. Immunol.* 13:202–208 (1983)); M18/2 (IgG$_{2a}$; Sanches-Madrd et al, *J. Exp. Med.*158:586 (1983)); H52 (American Type Culture Collection (ATCC) Deposit HB 10160); Mas191c and IOT18 (Vermot Desroches et al., *Scand. J. Immunol.* 33:277–286 (1991)); and NA-8 (WO 94/12214). The preferred antibody is one which binds to the CD18 epitope to which either MHM23 or H52 binds. In certain embodiments, the antibody may bind to a region in the extracellular domain of CD18 which associates with CD11b and the antibody may also dissociate α and β chains (e.g. the antibody may dissociate the CD11b and CD18 complex as is the case for the MHM23 antibody).

Techniques for producing antibodies which can be formulated as disclosed herein will be elaborated below.

A. Antibody Preparation (i) Antigen Preparation

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

(ii) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl$_2$, or R$^1$N=C=NR, where R and R$^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ¹⁄₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(iii) Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp.59–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al, *Monoclonal Antibody Production Techniques and Applications*, pp. 51–63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subloned by limiting dilution procedures and grown by standard methods (Goding, *Monoclonal Antibodies: Principles and Practice*, pp.59–103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described in McCafferty et al., *Nature*, 348:552–554 (1990).

Clackson et al., *Nature*, 352:624–628 (1991) and Marks et al., *J. Mol. Biol.*, 222:581–597 (1991) describe the isolation of murine and human antibodies, respectively, using phage libraries. Subsequent publications describe the production of high affinity (nM range) human antibodies by chain shuffling (Marks et al., *Bio/Technology*, 10:779–783 (1992)), as well as combinatorial infection and in vivo recombination as a strategy for constructing very large phage libraries (Waterhouse et al., *Nuc. Acids. Res.*, 21:2265–2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iv) Humanized and Human Antibodies

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad Sci. USA*, 89:4285 (1992); Presta et al., *J. Immnol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al, *Proc. Natl. Acad. Sci. USA*, 90:2551 (1993); Jakobovits et al., *Nature*, 362:255–258 (1993); Bruggermann et al., *Year in Immuno.*, 7:33 (1993); and Duchosal et al. *Nature* 355:258 (1992). Human antibodies can also be derived from phage-display libraries (Hoogenboom et al, *J. Mol. Biol.*, 227:381 (1991); Marks et al, *J. MoL Biol.*, 222:581–597 (1991); Vaughan et al. *Nature Biotech* 14:309 (1996)).

(v) Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107–117 (1992) and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163–167 (1992)). In another embodiment as described in the example below, the F(ab')$_2$ is formed using the leucine zipper GCN4 to promote assembly of the F(ab')$_2$ molecule. According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

(vi) Multispecific Antibodies

Multspecific antibodies have binding specificities for at least two different epitopes, where the epitopes are usually from different antigens. While such molecules normally will only bind two different epitopes (i.e. bispecific antibodies, BsAbs), antibodies with additional specificities such as trispecific antibodies are encompassed by this expression when used herein. Examples of BsAbs include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell ahesion molecule (NCAM)/anti-CD3, anti-folate binding protein (FBP)/anti-CD3, anti-pan carcinoma associated antigen (AMOC-31)/anti-CD3; BsAbs with one arm which binds specifically to a tumor antigen and one arm which binds to a toxin such as anti-saporin/anti-ld-1, anti-CD22/anti-saporin, anti-CD7/anti-saporin, anti-CD38/anti-saporin, anti-CEA/anti-ricin A chain, anti-interferon-α(IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); BsAbs which can be used as fibrinolytic agents such as anti-fibrin/anti-tssue plasminogen activator (tPA), anti-flbrin/anti-urokinase-type plasminogen activator (uPA); BsAbs for targeting immune complexes to cell surface receptors such as anti-low density lipoprotein (LDL)/anti-Fc receptor (e.g. FcγRI, FcγRII or FcγRIII); BsAbs for use in therapy of infectious diseases such as anti-CD3/anti-herpes simplex virus (HSV), anti-T-cell receptor:CD3 complex/anti-influenza, anti-FcyR/anti-HIV; BsAbs for tumor detection in vitro or in vivo such as anti-CEA/anti-EOTUBE, anti-CEA/anti-DPTA, anti-p185$^{HER2}$/anti-hapten; BsAbs as vaccine adjuvants; and BsAbs as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase. Examples of trispecific antibodies include anti-CD3/anti-CD4/anti-CD37, anti-CD3/anti-CD5/anti-CD37 and anti-CD3/anti-CD8/anti-CD37. Bispecific antibodies can be prepared as full length antibodies or antibody fragments (e.g. F(ab')$_2$ bispecific antibodies).

Methods for making bispecific antibodies are known in the art. Traditonal production of full length bispecific antibodies is based on the coexpression of two immunoglobulin heavy chain-light chain pairs, where the two chains have different specificities (Millstein et al., *Nature*, 305:537–539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655–3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypepbde fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217–225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.*, 148(5):1547–1553 (1992). The leucine zipper pepbdes from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Nati. Acad. Sci. USA*, 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al, *J. Immunol*, 152:5368 (1994).

Antibodies with more than two valencies are contemplated. For example, trispecific antibodies can be prepared. Tuft et al. *J. Immunol.* 147: 60 (1991).

(vii) Effector Function Engineering

It may be desirable to modify the antibody of the invention with respect to effector function, so as to enhance the effectiveness of the antibody. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191–1195 (1992) and Shopes, B. *J. Immunol.* 148:2918–2922 (1992). Homodimeric antibodies with enhanced anti-tumor activity may also be prepared using heterobifunctonal cross-linkers as described in Wolff et al. *Cancer Research* 53:2560–2565 (1993). Alternatively, an antibody can be engineered which has dual Fc regions and may thereby have enhanced complement lysis and ADCC capabilities. See Stevenson et al *Anti-Cancer Drug Design* 3:219–230 (1989).

(viii) Antibody-Salvage Receptor Binding Epitope Fusions.

In certain embodiments of the invention, it may be desirable to use an antibody fragment, rather than an intact antibody, to increase tumor penetration, for example. In this case, it may be desirable to modify the antibody fragment in order to increase its serum half life. This may be achieved, for example, by incorporation of a salvage receptor binding epitope into the antibody fragment (e.g. by mutation of the appropriate region in the antibody fragment or by incorporating the epitope into a peptide tag that is then fused to the antibody fragment at either end or in the middle, e.g., by DNA or peptide synthesis).

The salvage receptor binding epitope preferably constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of the antibody. Alternatively, the epitope is taken from the CH2 domain of the Fc region and transferred to the $C_L$ region or $V_L$ region, or both, of the antibody fragment.

In one most preferred embodiment, the salvage receptor binding epitope comprises the sequence (5' to 3'): PKNSSMISNTP (SEQ ID NO:4), and optionally further comprises a sequence selected from the group consisting of HQSLGTQ (SEQ ID NO:5), HQNLSDGK (SEQ ID NO:6), HQNISDGK (SEQ ID NO:7), or VISSHLGQ (SEQ ID NO:8), particularly where the antibody fragment is a Fab or F(ab')$_2$. In another most preferred embodiment, the salvage receptor binding epitope is a polypeptide containing the sequence(s) (5' to 3'): HQNLSDGK (SEQ ID NO:6), HQNISDGK (SEQ ID NO:7), or VISSHLGQ (SEQ ID NO:8) and the sequence: PKNSSMISNTP (SEQ ID NO:4).

(ix) Other Covalent Modifications of the Antibody

Covalent modifications of the antibody are included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues. Examples of covalent modifications are described in U.S. Pat. No. 5,534,615, specifically incorporated herein by reference. A preferred type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

(x) Selecting Biologically Active Antibodies

Antibodies produced as described above may be subjected to one or more "biological activity" assays to select an antibody with beneficial properties from a therapeutic perspective.

The antibody may be screened for its ability to bind the antigen against which it was raised. In the case of an anti-CD18 antibody, as shown in the example below, the antigen binding properties of the antibody can be evaluated in a "MAC-1 capture assay". Briefly, the assay involves first coating ELISA plates with an anti-CD18 antibody that binds to a site of MAC-1 different from the anti-CD18 antibody of interest to capture a recombinant preparation of soluble MAC-1, followed by a wash, addition of the sample to be tested, wash, addition of goat HRP-labeled anti-human F(ab')$_2$ antibody and colonmetric detection of OPD substrate. The total amount of antibody may be measured by first coating an ELISA plate with a polyclonal anti-F(ab')$_2$ antibody, followed by addition of the sample, and then HRP-anti-F(ab')$_2$ and colorimetric detection of the HRP substrate, OPD. Specific activity is the ratio of the MAC-1 binding to total F(ab')$_2$ ELISA value.

In another embodiment, the affinity of the antibody may be determined by saturation binding; ELISA; and/or competition assays (e.g. RIA's), for example.

Also, the antibody may be subjected to other biological activity assays, e.g., in order to evaluate its effectiveness as a therapeutic. Such assays are known in the art and depend on the target antigen and intended use for the antibody.

Where the antibody binds CD18, examples of biological activity assays include a slide adhesion assay, phagocytosis assay, neutrophil binding assay and degranulation assay.

The slide adhesion assay involves preincubating heparinized blood with various concentrations of anti-CD18 antibody, and then placing aliquots onto chambered glass slides. The slides are incubated at 37° C. to allow cells to adhere, nonadherent cells are gently washed off, the adherent cells are stained, and the average number of adherent cells per microscope field is determined for 30 fields.

For the phagocytosis assay, heparinized whole blood is obtained and the red blood cells are lysed. The cells are then incubated with opsonized BODIPY-labeled Staphylococcus aureus particles for 30 min at 37° C. The cells are then analyzed by FACS, and the fluorescence intensity in the neutrophil gate is determined as an indication of the extent of phagocytosis.

For determining binding of anti-CD18 antibody to neutrophils, whole blood is incubated with various concentrations of the anti-CD18 antibody. The cells are then stained with a FITC-conjugated goat anti-human $F(ab')_2$ antibody, the red blood cells are lysed, and the white blood cells are analyzed by FACS. The fluorescence intensity in the neutrophil gate is proportional to the extent of anti-CD18 antibody binding.

For a degranulation assay, neutrophils are isolated from whole blood and preincubated with anti-CD18 antibody. The cells are then stimulated with opsonized zymosan particles and allowed to stand at room temperature. The cellular supernatants are then collected, and degranulation is assessed either by specific ELISA (for myeloperoxidase or lactoferrin) or by enzyme assay (for elastase).

For other antibodies, examples of biological activity assays include tumor cell growth inhibition assays (as described in WO 89/06692, for example); antibody-dependent cellular cytotoxicity (ADCC) and complement-mediated cytotoxicity (CDC) assays (U.S. Pat. No. 5,500, 362); and agonistic activity or hematopoiesis assays (see WO 95/27062).

To screen for antibodies which bind to a particular epitope on the antigen of interest (e.g., those which block binding of the humanized H52 antibody of the example to CD18), a routine cross-blocking assay such as that described in *Antibodies, A Laboratory Manual*, Cold Spring Harbor Laboratory, Ed Harlow and David Lane (1988), can be performed. Alternatively, epitope mapping, e.g. as described in Champe et al., *J. Biol. Chem.* 270:1388–1394 (1995), can be performed to determine whether the antibody binds an epitope of interest.

B. Vectors, Host Cells and Recombinant Methods

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence (e.g. as described in U.S. Pat. No. 5,534,615, specifically incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as Escherichia, e.g., *E. coli*, Enterobacter, Erwinia, Klebsiella, Proteus, Salmonella, e.g., *Salmonella typhimurium*, Serrafia, e.g, *Serratia marcescans*, and Shigeila, as well as Bacilli such as *B. subtilis* and *B. licheniformis* (e.g., *B. licheniformis* 41P disclosed in DD 266,710 published Apr. 12, 1989), Pseudomonas such as *P. aeruginosa*, and Streptomyces. One preferred *E. coli* cloning host is *E. coli* 294 (ATCC 31,446), although other strains such as *E. coli* B, *E. coli* X 1776 (ATCC 31,537), and *E coil* W3110 (ATCC 27,325) are suitable. These examples are illustrative rather than limiting.

In additlon to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; Kluyveromyces hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); Candida; *Trichoderma reesia* (EP 244,234); *Neurospora crassa*; Schwanniomyces such as *Schwanniomyces occidentalis*; and filamentous fungi such as, e.g., Neurospora, Penicillium, Tolypocladium, and Aspergillus hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed bySV40 (COS-7, ATCC CRL 1651); human embryonic kidney line (293 or 293 cells subloned for growth in suspension culture, Graham et al, *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44–68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed cells, is removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1–13 (1983)). Protein G is recommended for all mouse isotypes and for human γ3 (Guss et al., *EMBO J.* 5:1567–1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSET™ chromatography on an anion or cation exchange resin (such as a polyaspartic acid column), chromatofocusing, SDS-PAGE, and ammonium sulfate precipiation are also available depending on the antibody to be recovered.

C. Preparation of the Formulation

After preparation of the antibody of interest as described above, the pharmaceutical formulation comprising it is prepared. The antibody to be formulated has not been subjected to prior lyophilization and the formulation of interest herein is an aqueous formulation. Preferably the antibody in the formulabon is an antibody fragment, such as an $F(ab')_2$, in which case problems that may not occur for the full length antibody (such as clipping of the antibody to Fab) may need to be addressed. The therapeutically effective amount of antibody present in the formulation is determined by taking into account the desired dose volumes and mode (s) of administration, for example. From about 0.1 mg/mL to about 50 mg/mL, preferably from about 0.5 mg/mL to about 25 mg/mL and most preferably from about 2 mg/mL to about 10 mg/mL is an exemplary antibody concentration in the formulabon.

An aqueous formulation is prepared comprising the antibody in a pH-buffered solution The buffer of this invention has a pH in the range from about 4.5 to about 6.0, preferably from about 4.8 to about 5.5, and most preferably has a pH of about 5.0. Examples of buffers that will control the pH within this range include acetate (e.g. sodium acetate), succinate (such as sodium succinate), gluconate, histidine, citrate and other organic acid buffers. The buffer concentration can be from about I mM to about 50 mM, preferably from about 5 mM to about 30 mM, depending, for example, on the buffer and the desired isotonicity of the formulation. The preferred buffer is sodium acetate (about 10 mM), pH 5.0.

An polyol, which acts as a tonicifier and may stabilize the antibody, is included in the formulation. In preferred embodiments, the formulation does not contain a tonicifying amount of a salt such as sodium chloride, as this may cause the antibody to precipitate and/or may result in oxidation at low pH. In preferred embodiments, the polyol is a nonreducing sugar, such as sucrose or trehalose. The polyol is added to the formulation in an amount which may vary with respect to the desired isotonicity of the formulation. Preferably the aqueous formulation is isotonic, in which case suitable concentrations of the polyol in the formulation are in the range from about 1% to about 15% w/v, preferably in the range from about 2% to about 10% whv, for example. However, hypertonic or hypotonic formulations may also be suitable. The amount of polyol added may also alter with respect to the molecular weight of the polyol. For example, a lower amount of a monosaccharide (e.g. mannitol) may be added, compared to a disaccharide (such as trehalose).

A surfactant is also added to the antibody formulation. Exemplary surfactants include nonionic surfactants such as polysorbates (e.g. polysorbates 20, 80 etc) or poloxamers (e.g. poloxamer 188). The amount of surfactant added is such that it reduces aggregation of the formulated antibody and/or minimizes the formation of particulates in the formulation and/or reduces adsorption. For example, the surfactant may be present in the formulation in an amount from about 0.001% to about 0.5%, preferably from about 0.005% to about 0.2% and most preferably from about 0.01% to about 0.1%.

In one embodiment, the formulation contains the above-identified agents (i.e. antibody, buffer, polyol and surfactant) and is essentially free of one or more preservatives, such as benzyl alcohol, phenol, m-cresol, chlorobutanol and benzethonium Cl. In another embodiment, a preservative may be included in the formulation, particularly where the formulation is a multdose formulation. The concentration of preservative may be in the range from about 0.1% to about 2%, most preferably from about 0.5% to about 1%. One or more other pharmaceutically acceptable carriers, excipients or stabilizers such as those described in *Remington's Pharmaceutical Sciences* 16th edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; antoxidants including ascorbic acid and methionine; chelating agents such as EDTA; metal complexes (e.g. Zn-protein complexes); biodegradable polymers such as polyesters; and/or salt-forming counterions such as sodium.

The formulation herein may also contain more than one protein as necessary for the particular indication being treated, preferably those with complementary activities that do not adversely affect the other protein. For example, where the antibody is anti-CD18, it may be desirable to provide a further anti-adhesion antibody, such as an anti-ICAM-1 or anti-CD11a antibody along with the anti-CD18 antibody in a single formulation. Alternatively, the anti-CD18 antibody may be combined with another anbinflammatory agent or a thrombolytic agent. Such proteins are suitably present in combination in amounts that are effective for the purpose intended.

The formulations to be used for in vivo administration must be sterile. This is readily accomplished by filtrabon through sterile filtration membranes, prior to, or following, preparation of the formulation.

D. Administration of the Formulation

The formulation is administered to a mammal in need of treatment with the antibody, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. In preferred embodiments, the formulation is administered to the mammal by intravenous administration. For such purposes, the formulation may be injected using a syringe or via an IV line, for example.

The appropriate dosage ("therapeutcally effective amount") of the antibody will depend, for example, on the condition to be treated, the severity and course of the condition, whether the antibody is administered for preventive or therapeutic purposes, previous therapy, the patient's clinical history and response to the antibody, the type of antibody used, and the discretion of the attending physician. The antibody is suitably administered to the patent at one time or over a series of treatments and may be administered to the patent at any time from diagnosis onwards. The antibody may be administered as the sole treatment or in conjunction with other drugs or therapies useful in treating the condition in question.

As a general proposition, the therapeutically effective amount of the antibody administered will be in the range of about 0.1 to about 50 mg/kg of patent body weight whether by one or more administrations, with the typical range of antibody used being about 0.3 to about 20 mg/kg, more preferably about 0.3 to about 15 mg/kg, administered daily, for example. However, other dosage regimens may be useful. The progress of this therapy is easily monitored by conventional techniques.

In the case of an anti-CD18 antibody, a therapeutically effective amount of the antibody may be administered to treat inflammatory disorders such as hemorrhagic shock, thermal injury (such as that resulting from burns), stroke (including ischemic and hemorrhagic stroke), and myocardial infarction. Where the antibody is an antIL8 antibody, the disorder may be an inflammatory disorder such as adult respiratory distress syndrome (ARDS), hypovolemic shock, ulcerative colits, and rheumatoid arthritis.

E. Articles of Manufacture

In another embodiment of the invention, an article of manufacture is provided comprising a container which holds the aqueous pharmaceutical formulation of the present invention and optionally provides instructions for its use. Suitable containers include, for example, bottles, vials and syringes. The container may be formed from a variety of materials such as glass or plastic. An exemplary container is a 3–20 cc single use glass vial. Alternatively, for a multidose formulation, the container may be 3–100 cc glass vial. The container holds the formulation and the label on, or associated with, the container may indicate directions for use. The article of manufacture may further include other materials desirable from a commercial and user standpoint, including other buffers, diluents, filters, needles, syringes, and package inserts with instructions for use.

The invention will be more fully understood by reference to the following examples. They should not, however, be construed as limiting the scope of the invention. All literature and patent citations are incorporated herein by reference.

EXAMPLE 1

This example describes an aqueous formulation comprising the antibody, recombinant humanized anti-CD18 antibody (rhuMAb CD18). RhuMAb CD18 having the amino acid sequence shown in FIG. 1A (heavy chain; SEQ ID NO:1) and FIG. 1B (light chain; SEQ ID NO:2) was created by humanization of the murine monoclonal antibody muMAb H52 (Hildreth et al. *J. Immunology* 134:3272–3280 (1985)).

The rhuMAb CD18 was produced recombinantly as described below. Plasmid pS 1130 was constructed to direct production of a rhuMAb CD18 precursor molecule with a leucine zipper domain in *E. coli*. The precursor is cleaved during the purification process by the protease pepsin to yield rhuMAb CD18. rhuMAb CD18 is an F(ab')$_2$ molecule composed of two different peptides (light and heavy chains) linked by disulfide bonds. Fusion of a yeast GCN4 leucine zipper dimerizabon domain to the C-terminus of an Fab' substitutes for the Fc region and allows for efficient F(ab')$_2$ production in *E. coli*. The GCN4 leucine zipper domains interact to form stable dimeric structures (parallel coiled coils) that hold the hinge region cysteine residues of two heavy chains together so that the two native interchain disulfide bonds can form. This results in formation of F(ab')$_2$ complexes that are covalently linked by disulfide bonds. The leucine zipper domains are later removed from the rhuMAb CD18 precursor during the purification process using the protease pepsin, which cleaves uniformly between the two leucine residues of the hinge. This results in the formation of the rhuMAb CD18 F(ab')$_2$ molecule.

Figure 20:
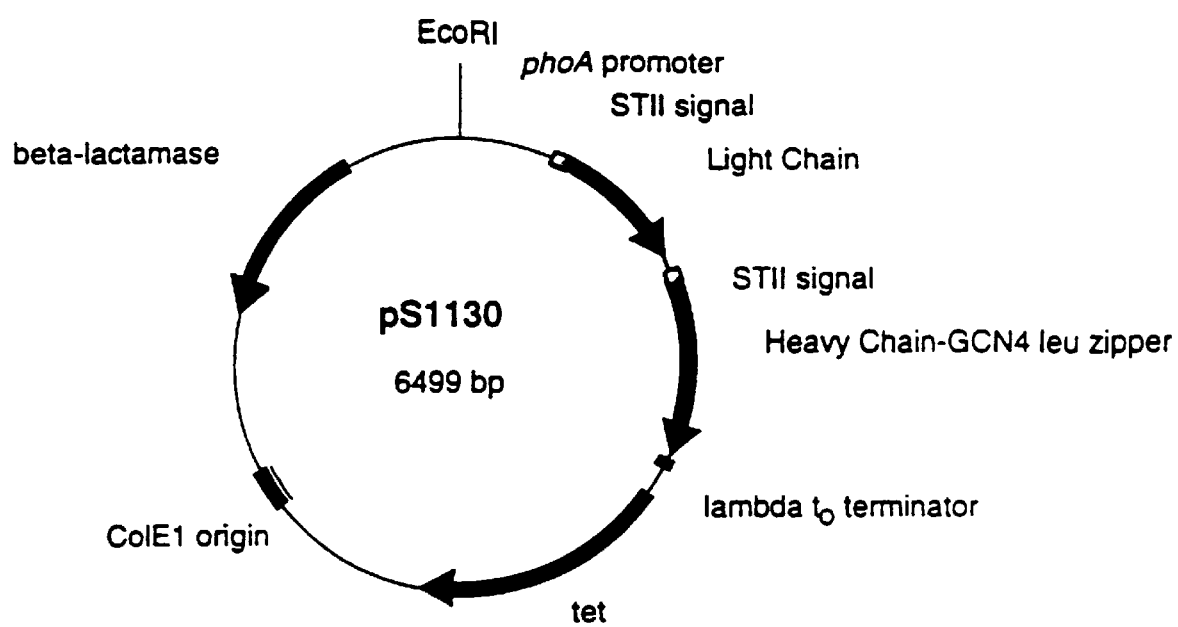
FIG. 20 depicts the structure of plasmid pS1130 used to produce rhuMAb CD18 of the example below.

Plasmid pS1130 (FIG. 20) is based on the well characterized plasmid pBR322 with a 2143 bp expression cassette (FIGS. 21A and 21B) inserted into the EcoRI restriction site. Plasmid pS1130 is resistant to both tetracycline and β-lactam antibiotics. The expression cassette contains a single copy of each gene linked in tandem. Transcription of each gene into a single dicistronic mRNA is directed by the *E. coli* phoA promoter (Chang et al. *Gene* 44:121–125 (1986)) and ends at the phage lamda to terminator (Scholtissek and Grosse *Nucleic Acids Research* 15:3185

Figure 23:
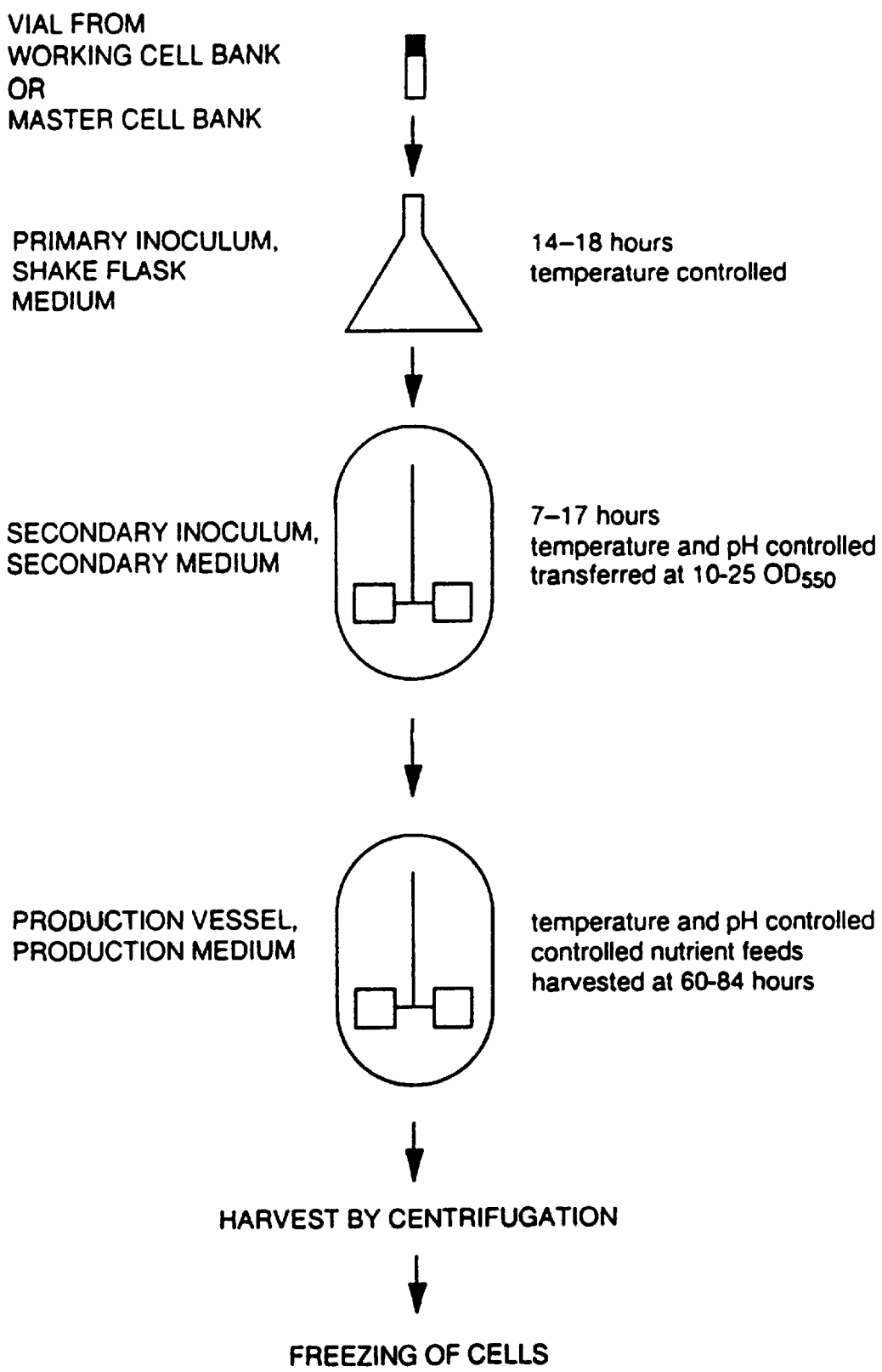
FIG. 23 is a schematic of the fermentation process for rhuMAb CD18.

(1987)). Translation initiation signals for each chain are provided by *E. coli* STII (heat stable enterotoxin) (Picken et al. *Infection and Immunity* 42:269–275 (1983)) Shine-Dalgarno sequences. Translation of each chain begins with a 23 residue STII signal peptide that directs translocaton of the pepbdes across the cytoplasmic membrane into the periplasmic space. The STII signal peptide is then removed by the *E. coli* leader peptidase. The light and heavy chains fold into their native conformations after secretion into the periplasm and associate into the rhuMAb CD18 precursor, a covalently linked F(ab')$_2$. The leucine zipper domain is cleaved from the precursor during the purification process (see below) to yield rhuMAb CD18. The cell line used in the production of rhuMAb CDI8 is 49A5, derived from *E. coli* cell line W3110 (ATCC 27,325) as shown in FIG. 22. The fermentation procedure takes place as shown in FIG. 23. Production of rhuMAb CD18 precursor occurs when the medium becomes depleted in phosphate, typically 30–60 hours after inoculation.

Purification of rhuMAb CD18 precursor from the *E. coli* cell paste was as follows. Frozen cell pellets containing antCD18 precursor antibody, were dissolved in about 3 volumes of extraction buffer (120 mM MES, 5mM EDTA buffer, pH 6) heated to 30–40° C. This resulted in a suspension with a pH between about 5.4 and 6.5. This suspension was passed twice through a Gaulin homogenizer at 5500 to 6500 psi and kept below 20° C. with a heat exchanger. 5% polyethyleineimine (PEI) (wh), pH 6 was added to the homogenate to a final concentration of 0.2% PEI. The mixture was incubated for about one hour at 2–8° C. About one volume of extraction buffer (120 mM MES, 5 mM EDTA, pH 6) was added before the solids were removed by centrifugation at 15,280 g. The clear supernatant was conditioned to a conductivity of less than 3mohms by the addition of cold water. The conditioned supernatant was loaded onto a cation exchange column (ABX column; Mallinckrodt Baker, Inc., N.J., USA) equilibrated in 50 mM MES, pH 6.0. sodium citrate, pH 6.0. The cation exchange anti-CD18 precursor antibody pool was diluted with 50 mM MES, 36 mM sodium citrate, pH 4.0 to a concentration of approximately 2 g/L. The pool was then adjusted to pH 4 by addition of 2 M citric acid and flowed through a column containing immobilized pepsin (pepsin-CPG) previously equilibrated with 50 mM MES, 36 mM sodium citrate pH 4.0. Pepsin (Sigma, Mo., USA) was chemically coupled to controlled pore glass (CPG) by Bioprocess Ltd., NJ, USA; the CPG was activated with NalO4 followed by reduction of schiff base formation between CPG and pepsin using NaBH3CN). This procedure removed the zippers from the hinge region while leaving intact F(ab')$_2$. The effluent from the pepsin-CPG column was filtered directly in line through an anion exchange Sartobind Q filter (Sartorius, Goettingen, West Germany). The generated anti-CD18 F(ab')$_2$ antibody flows through the filter while pepsin and other negatively charge impurities bind strongly to the filter. The pool was diluted to give a conductivity of approx. 7 mohms by the addition of water and was then applied to a cation exchange column (SP Sepharose HP) equilibrated was 25 mM MES, 60 mM acetic acid, pH 4.0. The SP Sepharose column was washed with 25 mN MES, 75 MM sodium acetate pH 5.6 and eluted in a linear gradient of 75–110 mM sodium acetate in 25 mN MES pH 5.6. The pooled fraction from the SP sepharose column was diluted with the addition of 3.0M ammonium sulphate, 25 mM MES pH 6.0 at a ratio of 0.26 liters per liter of pool and was then passed through a hydrophobic interaction chromatography (HIC) column (phenyl sepharose FF-low substitution) previously equilibrated in 0.625 M ammonium sulphate, 25 nM MES pH 6.0. After loading, the column was washed with same buffer used in equilibration and the rhuMAb CD18 was eluted in 0.375M ammonium sulphate, 25 mN MES pH 6.0.

This resulted in purified rhuMAb CD18 for formulating as described below. Five aqueous formulations were evaluated for selection of a clinical formulation for use in, e.g., hemorrhagic shock. The formulations were as shown in Table 1 below.

TABLE 1

Matrix of formulations prepared for this study.

| Formulation | Buffer | pH | TWEEN 20 ™ (0.01% v/v) | NaCl (140 mM) | Mannitol (4% w/v) | Trehalose (8% w/v) |
|---|---|---|---|---|---|---|
| F1 | 10 mM Acetate | 5.0 | + | + | | |
| F2 | 10 mM Acetate | 5.0 | + | | | + |
| F3 | 10 mM Histidine | 6.0 | + | + | | |
| F4 | 10 mM Histidine | 6.0 | + | | + | |
| F5 | 10 mM Histidine | 6.0 | + | | | + |

Two pH's were compared, pH 5 (sodium acetate) and pH 6 (histidine). At each pH, sodium chloride and trehalose were compared as tonicifiers. A histidine formulation with mannitol at pH 6 was also evaluated. The presence of a surfactant (e.g. 0.01% TWEEN 20™) was found to be required for stabilization against shaker-induced aggregation and for preventing adsorption to containers at protein concentrations below 1 mg/mL. The stability assays indicated that the trehalose formulations were generally superior to the others, with pH 5 showing slightly greater chemical stability than the pH 6 formulation due to reduced clipping. Kinetic data after 2 weeks and 5 weeks storage at 5, 30, and 40° C. were used for Arrhenius analysis and shelf-life prediction. Using cation exchange HPLC, the preferred formulation for rhuMAb CD18 was 10 mM sodium acetate, 8% trehalose whv, 0.01% TWEEN 20™, pH 5.0, with a predicted shelf life of 25–75 months (95% confidence intervals) at 5° C.

In designing antibody formulations, it may be useful to analyze the structural properties of the antibody to be formulated, but this is not necessary. RhuMAb CD18 consists of beta sheets of light (left side of the molecule in FIG.

Figure 16:
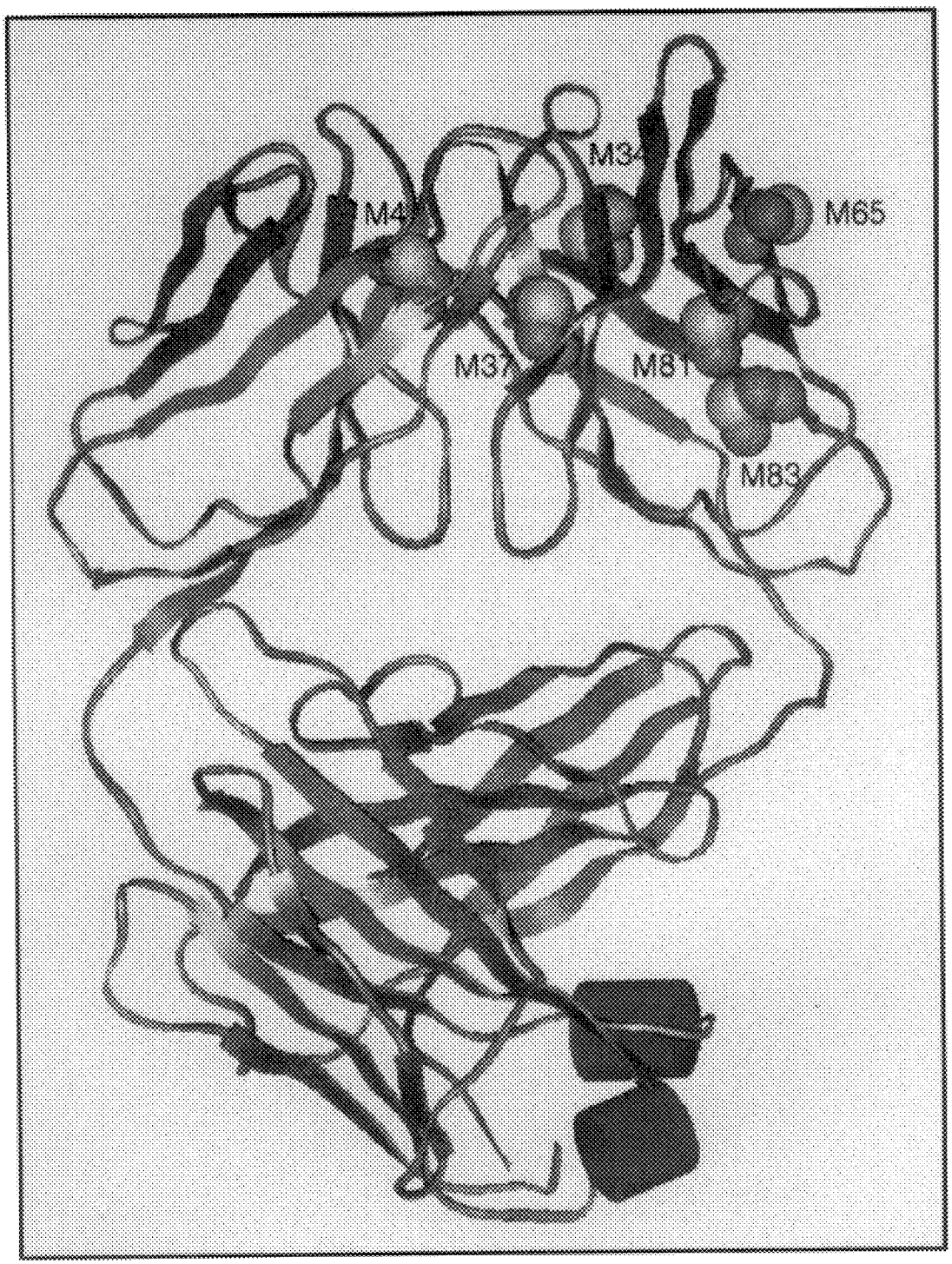
FIG. 16 shows the three dimensional structure of rhuMAb CD18, including positions of methionine residues. Met 65 and Met 83 are exposed, whereas others are buried in the structure and are expected to be less labile to oxidation.

16) and heavy chains (right side of the molecule in FIG. 16) which are structurally stabilized each by two intramolecular disulfides and held together by two intermolecular disulfides (depicted as barrels at the bottom of FIG. 16). The CDRs (complimentarity determining regions) in the variable segments are oriented on the top of the molecule. Located within and close to the CDRs are a number of methionines, only one of which (Met 65) is fully exposed. Though Met 65 is buried in anti-CD18, it is near a histidine residue which, without being limited to any one theory, might promote metal induced oxidation of proximal methionine (Li et al. *Biochem.* 34(17):5762–5772 (1995)). Susceptibility to oxidation in the CDRs was assessed herein. It was found to be desirable to use a sugar as the tonicifler, rather than a salt, so as to minimize oxidation at low pH.

Figure 2A:
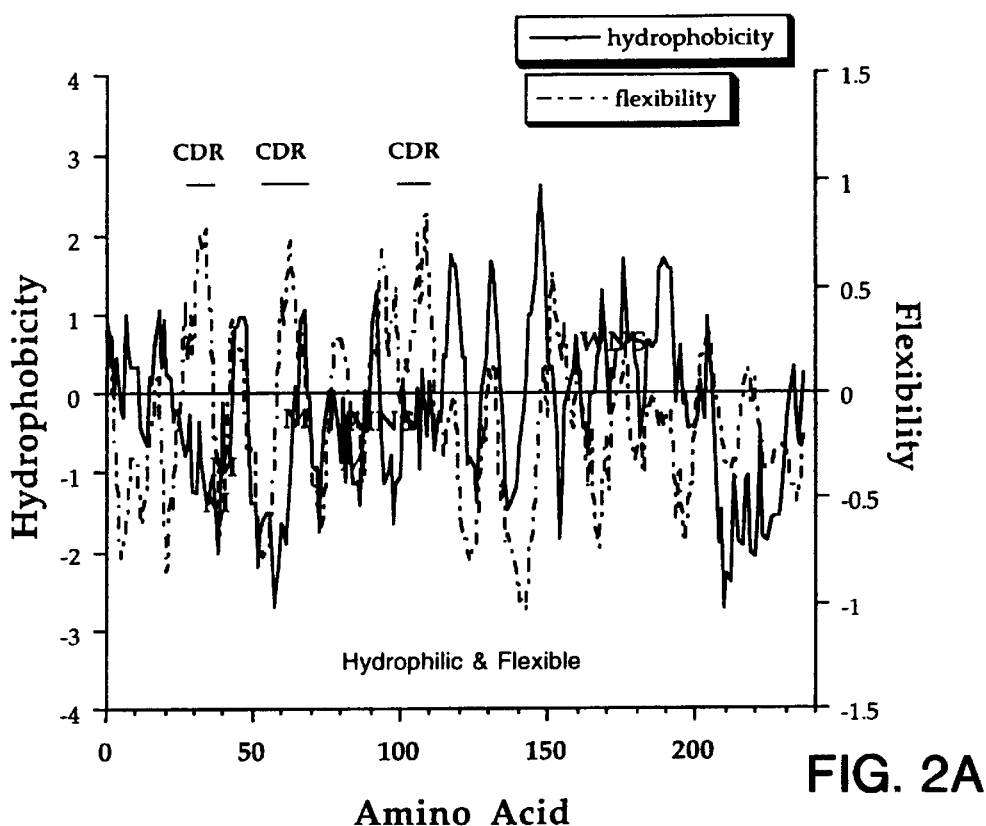
FIGS. 2A and 2B are hydroflex plots of rhuMAb CD18 heavy chain (FIG. 2A) and light chain (FIG. 2B). Kyte-Dooliutle hydrophobicity calculations averaged with a window of 6 amino acids were made on the protein sequence. Flexibility values were estimated from the product of the hydrophobicity of each residue and its side chain volume (again averaged over a window of 6 residues). Asn-Gly and Asn-Ser motifs in flexible regions are more likely to deamidate than those in more rigid structures. The CDRs are also shown. Most of the heavy chain methionines and heavy chain Asn 84 are near the CDR's.
Figure 2B:
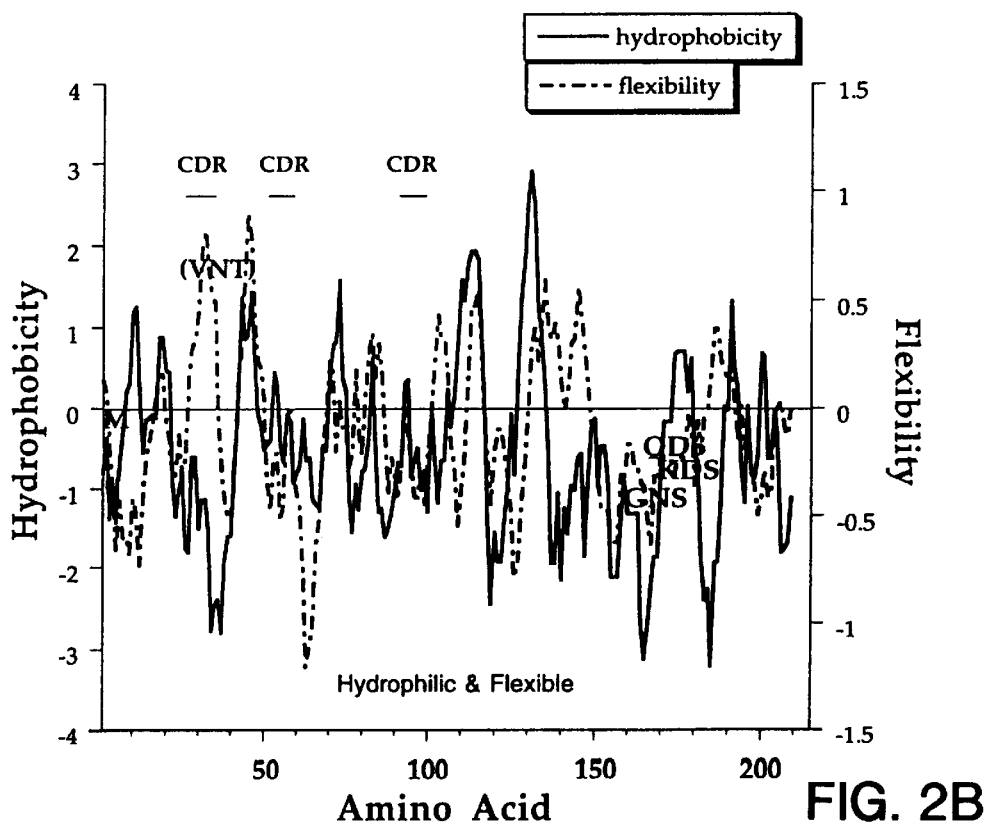

In assessing the potential deamidation or isomerization sites in this molecule, i.e. Asx-Gly or Asx-Ser (Asx indicates Asp or Asn) that are in hydrophilic and flexible regions (Clarke et al. in *Stability of Protein Pharmaceuticals. Part A. Chemical and Physical Pathways of Protein Degradation*, T. J. Ahern and M. C. Manning, Editors. 1992, Plenum Press: New York. p.2–29; and Kossiakoff, *Science*, 240:191–94 (1988)), six were found to be exposed and in fairly flexible regions (FIGS. 2A and 2B). Without being limited to any one theory, heavy chain motifs $MN^{84}S$, $KN^{55}G$, and light chain motifs $GN^{158}S$, $QD^{167}S$, $KD^{170}S$, are predicted to be most reactive; reactivity at Asn 84 is most likely to affect the binding activity of the antibody since it is near the CDR's. Asn 103 was found to be the primary route of degradation (via deamidation).

MATERIALS AND METHODS

The materials used in the following methods were as follows: glacial acetic acid 99.9% (MW 60.05); concentrated NaOH 18.94N (50% w/w; MW 40.0); concentrated HCl 37.8% (12.44N; MW 36.46); hisbidine (MW 155.16); NaCl (MW 58.44g); pharmaceutical grade trehalose dihydrate (MW 342.31); D-mannitol (MW 182.17); low peroxide TWEEN 20™; rhuMAb anti-CD18 (~1.3 mg/mL in MOPS, Na acetate, pH 6.9).

Buffer preparation and formulation set-up: Two liters of the following stock buffers were prepared for dialysis and formulation:

0.2 M Sodium Acetate, pH 5: 22.7 mL acetic acid, 17 mL 50% NaOH, made up to 2 L with Milli-Q water. Final pH 4.98. The solution was sterile filtered into 2 L Nalgene bottles and stored at 5° C.

0.2 M Histidine, pH 6: 62.06 g of Histidine, 20 mL concentrated HCl, made up to 2 L in a volumetric flask. Final pH 5.92. The solution was sterile filtered into 2 L Nalgene bottles and stored at 5° C.

2 M NaCl: 116.88 g NaCl, made up to 1 L with Milli-Q water. The solution was sterile filtered into 1 L Nalgene bottles and stored at 5° C.

18% Mannitol: 180 g mannitol, made up to 1 L with MilliQ water. The solution was sterile filtered into 1 L Nalgene bottles and stored at 5° C.

20% Trehalose: 400 g trehalose, made up to 2 L with Milli-Q water. Final pH was 6.4. The solution was sterile filtered into 2 L Nalgene bottles and stored at 5° C.

10% (v/v) TWEEN 20™: 10 mL of concentrated TWEEN 20™ was carefully removed and added to a 100 mL volumetric flask, diluted with Milli-Q water, and stirred until dissolved. Stored at 2–8° C. in the dark.

Formulation: Table 2 below shows the preparation of the buffers against which the starting protein bulk was dialyzed for this study. Approximately 40 mL of the bulk rhuMAb CD18 (~1 .3mg/mL protein concentration) was dialyzed (2 L for 4 hr at 5° C. and ~2 L overnight) to solutions prepared as shown in Table 2. The dialyzate was filtered with 0.2 μM Nalgene cellulose acetate filter units and stored under aseptic conditions for use as blank for UV and HPLC analysis.

TABLE 2

Summary of formulation preparation

| Formulation | | 0.2 M buffer (mL) | 18% Mannitol (mL) | 20% Trehalose (mL) | 1M NaCl (mL) | Approx. Water (mL) | pH | final pH | Made up to (mL) |
|---|---|---|---|---|---|---|---|---|---|
| F1 | Acet/5 | 200 | — | — | 560 | 3000 | 5.07 | 5.07 | 4000 |
| F2 | Acet/5 | 200 | — | 1600 | — | 2000 | 5.17* | 5.07 | 4000 |
| F3 | His/6 | 200 | — | — | 560 | 3900 | 6.03 | 6.03 | 4000 |
| F4 | His/6 | 200 | 889 | — | — | 2800 | 5.85* | 6.01 | 4000 |
| F5 | His/6 | 200 | — | 1600 | — | 2000 | 5.97 | 5.97 | 4000 |

*Formulation F2 was adjusted with acetic acid buffer made by diluting 286 μL of glacial acetic acid and 200 mL of the 20% trehalose and mixed with Milli-Q water to a final 500 mL. This is 10 mM acetic acid with 8% trehalose. Approximately 250 mL was required to adjust the pH as required. Formulation F4 was adjusted with 0.5 mL of 50% NaOH.

Some of the remaining dialysis buffer was used to prepare formulation vehicles by adding TWEEN 20™, as shown in Table 3.

TABLE 3

Summary of preparation of formulation vehicles

| Vehicle | Dialysis Buffer (mL) | 10% TWEEN 20 ™ (μL) | Final Vol. (mL) |
|---|---|---|---|
| F1 | 41.4 | 41 | 41.4 |
| F2 | 41.5 | 42 | 41.5 |
| F3 | 42.4 | 42 | 42.4 |
| F4 | 42.2 | 42 | 42.2 |
| F5 | 41.4 | 41 | 41.4 |

Table 4 below shows the final appearance, pH, and protein concentration of the dialyzed protein solutions.

TABLE 4

Summary of analysis of the dialyzed protein solutions

| Formulation | OD280 diluted 1:1 | Conc. = OD/1.32[c] | pH of protein solution | Vehicle pH | color/ appearance | Temp ° C. |
|---|---|---|---|---|---|---|
| F1 | 0.8239 | 1.248 | 5.09 | 5.09 | CAC** | 24.7 |
| F2 | 1.1192 | 1.696 | 5.09 | 5.09 | CAC | 24.7 |
| F3 | 0.84605 | 1.282 | 6.06 | 6.06 | CAC | 24.7 |
| F4 | 0.89763 | 1.36 | 6.10 | 6.10 | CAC | 24.7 |
| F5 | 1.116 | 1.69 | 5.91 | 5.91 | CAC | 24.7 |

*Extinction coefficient was later changed to 1.45 mL/mg/cm.
**CAC = clear and colorless.

These protein solutions were then diluted, using reserved dialysis buffer, to a final ~1 mg/mL protein concentration, and TWEEN 20™ was added to final 0.01% (v/v), as shown in Table 5.

TABLE 5

Summary of final formulation concentration adjustment and concentration determination

| Form. no. | Dialysis buffer (mL) | 10% TWEEN 20™ (μL) | Dialy. Protein (mL) | Starting Conc. (mg/mL) | Final Vol. (mL) | *Final OD280 | *Final Conc. (mg/mL) | *OD 340–360 |
|---|---|---|---|---|---|---|---|---|
| F1 | 8.16 | 41 | 33.2 | 1.248 | 41.4 | 1.3297 | 1.008 | 0.011 |
| F2 | 17.0 | 42 | 24.5 | 1.696 | 41.6 | 1.3332 | 1.010 | 0.017 |
| F3 | 9.26 | 42 | 33.1 | 1.282 | 42.4 | 1.3138 | 0.995 | 0.009 |
| F4 | 11.2 | 42 | 31 | 1.36 | 42.2 | 1.3065 | 0.990 | 0.010 |
| F5 | 16.9 | 41 | 24.5 | 1.69 | 41.4 | 1.3118 | 0.994 | 0.016 |

*Measured after filtration and filling.

The formulations were sterile filtered using 150 mL Nalgene filter units with cellulose acetate membranes in a sterile hood. The sterile formulated rhuMAb CD18 solutions were filled at 0.6 mL per 3 cc vial, labeled and stored at designated temperatures. Vehicle solutions were filtered and filled identically. Tables 6A (antibody formulations) and 6B (vehicle controls) below show the stability program for these formulations. Data presented here are up to 5 weeks storage.

TABLE 6A

CD18 antibody formulations

| time | 40° C. samples | 30° C. samples | 5° C. samples | −20° C. samples | −70° C. samples |
|---|---|---|---|---|---|
| t0 | | | 2 | 2 | 2 |
| 2 wk | 2 | 2 | 2 | | |
| 5 wk | 2 | 2 | 2 | 2 | 2 |
| 8 wk | 2 | 2 | 2 | | |
| 12 wk | 2 | 2 | 2 | 2 | 2 |
| 6 mo | | 2 | 2 | 2 | 2 |
| 9 mo–1 yr | | 2 | 2 | 2 | 2 |
| | 8 + 2 ext = 10 | 12 | 14 | 8 | 10 + 4 ext = 14 |

TABLE 6B

| | Vehicles | | | | |
|---|---|---|---|---|---|
| time | 40° C. vehicles | 30° C. vehicles | 5° C. vehicles | −20° C. vehicles | −70° C. vehicles |
| t0 | | | 1 | 1 | 1 |
| 2 wk | 1 | 1 | 1 | | |
| 5 wk | 1 | 1 | 1 | 1 | 2 |
| 8 wk | 1 | 1 | 1 | | |
| 12 wk | 1 | 1 | 1 | 1 | 2 |
| 6 mo | | 1 | 1 | 1 | 2 |
| 1 yr | | 1 | 1 | 1 | 2 |
| | 4 | 6 | 6 + 2 = 8 | 4 + 2 = 8 | 8 + 2 ext |

At the 2 week and 5 week timepoints, 2 vials from each formulation and storage temperature were frozen at −70° c. At the 5 week timepoint the frozen samples were thawed and batch analyzed together with control samples frozsen at −70° C. immediately after filling (t=0 weeks).

UV Spectroscopy: Samples were measured without dilution in a Hellma 2 mm wide, 1 cm path-length cell with raised bottom and black sides. Approximately 300 μL of sample was used for the measurements. The instrument was blanked with Milli-Q water. Samples were scanned from 200 to 400 nm with a 2 nm bandwidth and 1 second integration using a HP-8452A spectrophotometer.

Protein concentration was determined from the absorbance at 278 nm correcting for the absorbance at 320 nm using an extinction coefficient of 1.45 mL/mg/cm. The average value of absorbances in the region of $A_{340}$ to $A_{360}$ was followed as an indicator of scattering material.

pH: An Orion 720A pH meter was used with a MicroElectrodes, Inc. MI-410 micro pH electrode. The electrode was calibrated with pH 4 and 7 standard buffers, re-checked every 10–15 samples, and recalibrated as required. The instrument was calibrated and samples were measured at room temperature (~23° C.).

RP-HPLC: RP-HPLC was carried out using a 7.5×75 mm TSK Phenyl-5PW column with 0.1% TFA as the A buffer, and 0.08% TFA in acetonitrile as the B buffer. An inline 0.5,M filter was used before the column was equilibrated at 10% B buffer and run at 55° C. Injections of 20 µL were made and eluted according to Table 7 below:

TABLE 7

| Time (Minutes) | % B | Flow (mL/minute) |
| --- | --- | --- |
| 0 | 10 | 0.8 |
| 30 | 25 | 0.8 |
| 35 | 70 | 0.8 |
| 35.01 | 70 | 2 |
| 36 | 70 | 2 |
| 37 | 10 | 2 |
| 41 | 10 | 2 |

Data collected at 214 nm at 1 point per second were used for analysis.

SEC Assay: The mobike phase used was 200 mM NaCl, 50 mM sodium phosphate at pH 6.0. The runs were 40 minutes at a flowrate of 0.5 mL/minute with 40 µL injectons done at ambient temperature. A TSK G3000SWXL 30 cm×7.8 mm column with inline filter and a TSK guard column before the main column was used. Detection was at 214 nm.

Ion-Exchange HPLCAssay(IEX): IEX was run using 50 µL injections. The mobile phases were 33 mM each of MES/HEPESIPIPES, adjusted to pH 6.0 for A and pH 8.0 for B; C=Milli-Q water. The gradient shown in Table 8 below was used:

TABLE 8

| Time (min) | % B | % C | Flow (mL/min) |
| --- | --- | --- | --- |
| 0 | 0 | 50 | 1 |
| 3 | 0 | 50 | 1 |
| 15 | 20 | 50 | 1 |
| 50 | 50 | 50 | 1 |
| 50.1 | 100 | 0 | 2 |
| 51 | 100 | 0 | 2 |
| 51.1 | 0 | 50 | 2 |
| 60 | 0 | 50 | 2 |

The method used a 50×4.6 mm BakerBond carboxy-sulphon (CSx) cation exchange column with an inline 0.5 µM filter before the column, run at 40° C. Analysis was done with data obtained at 280 nm, due to the high buffer background.

Hydrophobic Interaction Chromatography (HIC): HIC was done on a 4.6×50 mm Baker Bond Butyl NPR column with inline 0.5 µM filter before the column. The running buffers were 2M ammonium sulfate in 20 mM Tris-HCl, pH 7 as the A buffer, and 20 mM Tris, pH 7 as the B buffer. The column was equilibrated at 50° C. with 10% buffer B at 1 mUminute and 10 µL injections were made. The gradient shown in Table 9 below was used for elution:

TABLE 9

| Time | % B |
| --- | --- |
| 0 | 10 |
| 1 | 10 |
| 35 | 100 |
| 37 | 100 |
| 37.1 | 10 |
| 42 | 10 |

Data were collected at 214 nm at 1 point per second.

SDS-PAGE: Pre-made 10 and 14% glycine SDS-PAGE gels (Novex, San Diego, Calif.) were used for analysis of the reduced and non-reduced samples, respectively. 10 µL of the 1 mg/mL sample diluted with 10 µL of 2×Tris-Glycine sample buffer (Novex) was heated 2 minutes at 95° C., as were high MW range and low MW range (Bio-Rad) markers diluted 1:20 in same sample buffer. Kaleidoscope MW marker was heated at 95° C., as well, with no dilution. When the samples cooled, 10 µL was loaded on the gels. The load of the MW marker solutions was 5 µL. The gel apparatus (Novex) was filled with 1×gel loading buffer (Media Services) and the gels were run at constant voltage of 125 mV and variable current for 2 hours. The gels were stained with the Novex Coomassie blue stain, overnight. The next day, the gels were washed with water for 2 hours and then were soaked in Gel Drying Solution (1×) (Novex) for ½ hour. The gels were then air-dried with the Novex cellophane system.

Gel Isoelectric Focusing Electrophoresis: IEF was done using Pharmacia 3.5 to 9.5 PAG plate gels. Pharmacia phosphoric acid and sodium hydroxide running buffers were used. Samples were prepared by mixing 10 µL of sample with 30 µL of 15% glycerol. Pharmacia broad range and high range IEF standards, as well as Serva Protein Test Mix 9 were run as pi markers. Pharmacia standards were prepared by mixing the standard (reconstituted with 0.5 mL of Milli-Q water) 1:1 with 15% glycerol. The Serva protein mix was reconstituted according to instructions and diluted 10-fold with 15% glycerol. On one gel, anti-HER2 MAb bulk (pl=8.8–9.0 calculated) was also run as a control. The HER2 sample (5 mg/mL) was diluted 40× with 15% glycerol. The gels were loaded with 20 µL of each sample adsorbed onto paper patches placed one third of the gel width from the positive electrode (the acid side). Gels were run at 10° C. with constant voltage set to 400 V for 30 minutes, after which the sample loading papers were removed and the gels were run for 1.5 more hours at 1500 V. Gels were fixed in TCA with sulfosalicylic acid for 30 minutes, and washed with water for 10 minutes (for the second gel) or IEF destain (for the third gel), and stained without washing out the TCA, as instructed in the Novex instructions (for the first gel). The first two gels were stained with Novex colliodal Coomassie according to the Novex instructions. The last gel was stained for 8 minutes with standard IEF Coomassie stain which was preheated to ~60° C., and then destained with IEF destain which had also been preheated to ~60° C. overnight. The gels were air-dried with the method described above for the SDS-PAGE gels.

Freeze/ThawStability: To demonstrate that rhuMAb CD18 would not degrade by freeze/thaw cycling in the formulations being tested, four vials of each formulation were subjected to three cycles of freezing and thawing. Two of the vials of each formulation were cycled between −70° C. and 2–8° C. and two were cycled between −20° C. and 2–8° C. Two vials of each formulation were held at 2–8 ° C. as controls. During each cycle the vials were allowed to remain in the freezer for at least 2 hours, until there was no visible liquid remaining in the vial. They were then transferred to 2–8° C. for at least 2 hours, until no solid remained. One vial of the acetate/trehalose, pH 5 formulation (F2) did not freeze at −20° C. on the first cycle, but froze immediately when placed on the shelf in a −70° C. freezer.

Shaker Studies: One vial of each formulation, and a vial of identically configured rhuMAb CD18 bulk, was placed horizontally into a rack on a Glas-Col 99A S60012 shaker. The shaker arm was adjusted to a radius of ~30 cm and the speed was set to 70 rpm. The samples were shaken for 24 hours at room temperature in the axial direction. A second vial of each formulation, and the bulk, was maintained at room temperature near the shaker, as a control. The samples were then analyzed by IEX, MAC-1 capture assay, and UV spectroscopy.

MAC-1 Capture (Receptor ELISA) and Total F(ab')$_2$ ELISA: rhuMAb CD18 is directed to the CD18 chain of MAC-1. The antigen binding property of rhuMAb CD18 can hence be evaluated by "MAC-1 capture assay". The assay involves coating of a 96 well mictrotitre plate first with a murine anti-CD18 antibody that binds to a site of MAC-1 different from rhuMAb CD18 (MHM23 MAb; Hildreth et al, *Eur. J. Immunol.* 13:202–208 (1983)) to capture a recombinant preparation of soluble MAC-1, followed by a wash with phosphate buffered saline (PBS), addition of the unknown sample, wash with PBS, addition of goat HRP-labeled anti-human F(ab')$_2$ antibody and colorimetric detection of OPD substrate. The total amount of antibody is measured by first coating an ELISA plate with a polyclonal anti-F(ab')$_2$ antibody, followed by addition of the sample, and then HRP-anti F(ab')$_2$ and calorimetric detection of the HRP substrate OPD. Assay diluents in both cases were 0.5% bovine serum albumin (BSA), 0.05% polysorbate 20, 1 mM CaCl$_2$, 1 mM MgCl$_2$ Specific activity was measured as the ratio of the MAC-1 binding to total F(ab')$_2$ ELISA value.

The samples were serially pre-diluted with assay diluent obtained to final dilutions of 20,000, 40,000, and 80,000 times in microtiter plates and Micronics tubes using multi-channel pipettors. The dilution scheme used was as shown in Table 10 below. Samples of diluted rhuMAb CD18 bulk were included on each assay plate as controls. These bulk controls were diluted one extra 2×dilution to final 40,000, 80,000, and 160,000 times. The same dilutions were used for both assays. Samples were diluted the same day as they were thawed for the 5 week analysis and then frozen in the Micronics tubes prior to submission for assay the following day. The freezelthaw stability of rhuMAb CD18 diluted in assay diluent in these assays was verified.

TABLE 10

| Step | Dilution (times) | Sample (µL) | Diluent (µL) |
|---|---|---|---|
| 1, in 96 well plate* | 10 | 10 | 90 |
| 2, in 96 well plate* | 10 | 10 | 90 |
| 3, in 96 well plate* | 10 | 10 | 90 |
| 4, in Micronics tubes | 20 | 50 | 950 |
| 5, in Micronics tubes | 2 | 500 | 500 |
| 6, in Micronics tubes | 2 | 500 | 500 |

*Later studies were conducted by making all dilutions in Micronics tubes and vortexing them to mix; this improved reproducibility.

Kinetic Parameters, Arrhenius Calculations, and Statistics: The loss in the % main peak versus time was fitted to first order kinetics. The observed rate constants (K) at various temperatures were then fitted to the Arrhenius equation as shown below:

$$\ln K = -\Delta E/RT + C$$

where E is the activation energy (in cal/mol), R is the Universal gas constant (1.987 cal/mol/K), T is the absolute temperature (in Kelvins) and C is a constant. From the slope of a plot of ln K VS. 1/T, ΔE was calculated. The standard error (SE) of ln K was calculated using the formula $[(1/K)^2+(SE)^2]^{0.5}$. The reason for a large SE value for ln K at lower temperatures is the small value of the K which is in the denominator of the formula. A value of K extrapolated from the Arrhenius fit (±95% confidence interval) was used to predict the shelf life at 5° C. according to:

$$t_{90}(wk) = \ln 0.9/K$$

where K was expressed in weeks$^{-1}$. Confidence intervals were determined using the program SIGMAPLOT™.

RESULTS AND DISCUSSION

Freeze/Thaw stability: Table 11 below shows a summary of the data from analysis of the samples in the freeze/thaw study. No significant differences were seen between the different temperature groups. The observation that one vial of F2 did not freeze at −20° C. on the first cycle raised a concern that freezing of bulk in a jacketed stainless steel storage tank might be problematic. The coldest parts of the solution in these tanks reach only about −20° C., and therefore might not freeze completely. This was tested using formulation vehicle. The tank was observed to freeze solid within 6 hours of cooling, so no problem for bulk storage is predicted.

TABLE 11

Effect of three cycles of freezing and thawing to 5° C. on the Stability of rhuMAb CD18

| Formulation | | RP-HPLC Total Area | RP-HPLC % Main | SEC Total Area | SEC % Main | UV Conc. (mg/mL) | UV Average 340–360 nm | MAC-1 Capture Titer (µg/mL) | Specific Activity (MAC-1/UV) |
|---|---|---|---|---|---|---|---|---|---|
| F1 | 5° C. | 10276 ± 25 | 88.0 ± 0.1 | 6401 ± 151 | 83.8 ± 0.4 | 0.949 ± 0.003 | 0.011 ± 0.001 | 1000 ± 32 | 1.05 ± 0.03 |
| | −20° C. | 10341 ± 106 | 88.2 ± 0.1 | 6556 ± 73 | 83.2 ± 0.1 | 0.952 ± 0.002 | 0.012 ± 0.001 | 948 ± 28 | 1.00 ± 0.03 |
| | −70° C. | 10328 ± 13 | 87.5 ± 0.01 | 6353 ± 63 | 83.0 ± 0.9 | 0.948 ± 0.005 | 0.013 ± 0.004 | 972 ± 15 | 1.03 ± 0.02 |
| F2 | 5° C. | 10537 ± 4 | 88.5 ± 0.2 | 6508 ± 18 | 81.7 ± 0.3 | 0.941 ± 0.006 | 0.017 ± 0.005 | 1069 ± 57 | 1.14 ± 0.06 |
| | −20° C. | 10644 ± 107 | 87.3 ± 0.5 | 6290 ± 54 | 83.1 ± ± 0.2 | 0.941 ± 0.002 | 0.012 ± 0.001 | 1132 ± 27 | 1.20 ± 0.03 |
| | −70° C. | 10503 ± 74 | 88.5 ± 0.2 | 6435 ± 120 | 82.5 ± 0.8 | 0.938 ± 0.000 | 0.009 ± 0.002 | 1064 ± 41 | 1.13 ± 0.04 |
| F3 | 5° C. | 10147 ± 50 | 87.9 ± 0.2 | 6311 ± 65 | 84.8 ± 0.3 | 0.926 ± 0.002 | 0.017 ± 0.001 | 1017 ± 77 | 1.10 ± 0.08 |
| | −20° C. | 10050 ± 43 | 88.4 ± 0.00 | 6404 ± 39 | 85.6 ± 0.1 | 0.922 ± 0.007 | 0.012 ± 0.001 | 997 ± 28 | 1.08 ± 0.03 |
| | −70° C. | 9953 ± 85 | 88.0 ± 0.2 | 6356 ± 52 | 83.9 ± 0.2 | 0.926 ± 0.002 | 0.017 ± 0.005 | 1021 ± 26 | 1.0 ± 0.03 |

TABLE 11-continued

Effect of three cycles of freezing and thawing to 5° C. on the Stability of rhuMAb CD18

| Formulation | RP-HPLC Total Area | RP-HPLC % Main | SEC Total Area | SEC % Main | UV Conc. (mg/mL) | UV Average 340–360 nm | MAC-1 Capture Titer (µg/mL) | Specific Activity (MAC-1/UV) |
|---|---|---|---|---|---|---|---|---|
| F4 5° C. | 10397 ± 26 | 88.2 ± 0.1 | 6304 ± 148 | 84.5 ± 1.1 | 0.921 ± 0.000 | 0.010 ± 0.003 | 905 ± 18 | 0.98 ± 0.02 |
| −20° C. | 10126 ± 180 | 88.6 ± 0.03 | 6467 ± 13 | 83.5 ± 0.2 | 0.922 ± 0.004 | 0.014 ± 0.001 | 1004 ± 20 | 1.09 ± 0.03 |
| −70° C. | 10322 ± 51 | 88.1 ± 0.1 | 6327 ± 3 | 84.7 ± 1.1 | 0.924 ± 0.004 | 0.009 ± 0.007 | 982 ± 21 | 1.06 ± 0.03 |
| F5 5° C. | 10438 ± 81 | 88.0 ± 0.1 | 6418 ± 64 | 85.9 ± 0.3 | 0.930 ± 0.001 | 0.016 ± 0.004 | 1058 ± 39 | 1.14 ± 0.04 |
| −20° C. | 10443 ± 10 | 88.3 ± 0.1 | 6310 ± 11 | 86.5 ± 0.4 | 0.923 ± 0.004 | 0.016 ± 0.003 | 1010 ± 49 | 1.09 ± 0.05 |
| −70° C. | 10350 ± 135 | 88.3 ± 0.00 | 6340 ± 58 | 85.5 ± 0.1 | 0.923 ± 0.003 | 0.017 ± 0.006 | 1003 ± 22 | 1.09 ± 0.02 |

Mean ± SE of two vials are shown. No significant loss in monomer content or receptor binding was noticed.

Figure 3A:
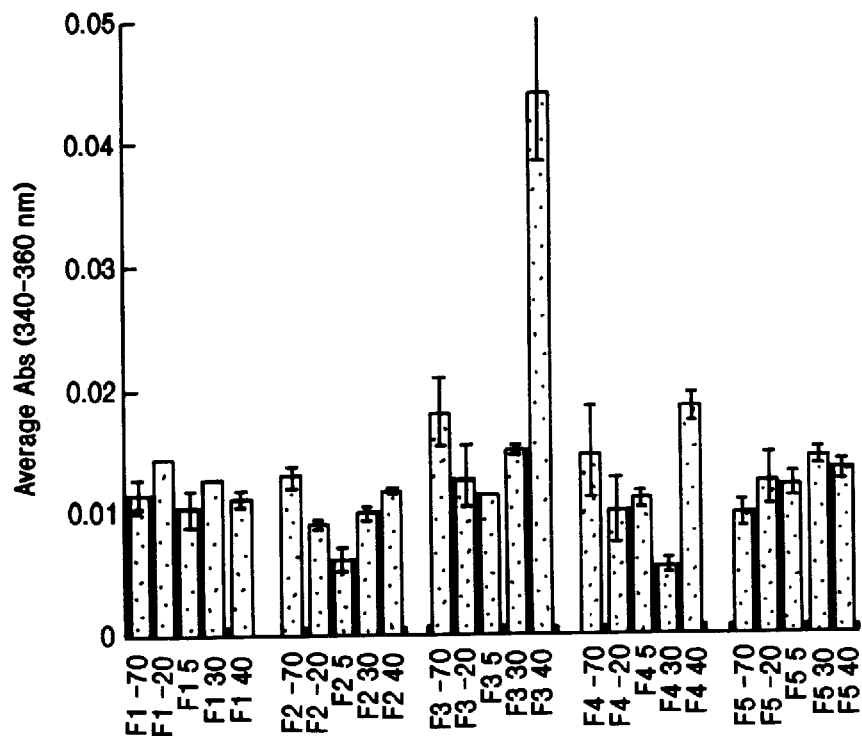
FIGS. 3A and 3B show the effect of storage temperature on light scattering in different rhuMAb CD18 formulations after 5 weeks storage at the designated temperatures as measured by average absorbance in the range of 340–360 nm (FIG. 3A), or the ratio of A278 over A252 nm (FIG. 3B). RhuMAb CD18 in formulation F3 is prone to the formation of insoluble aggregates.
Figure 3B:
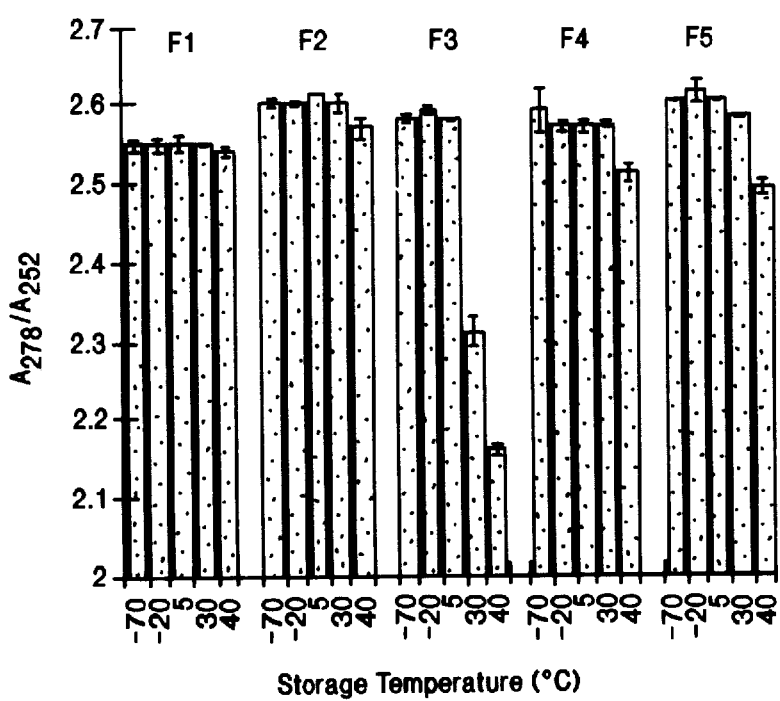
Figure 4:
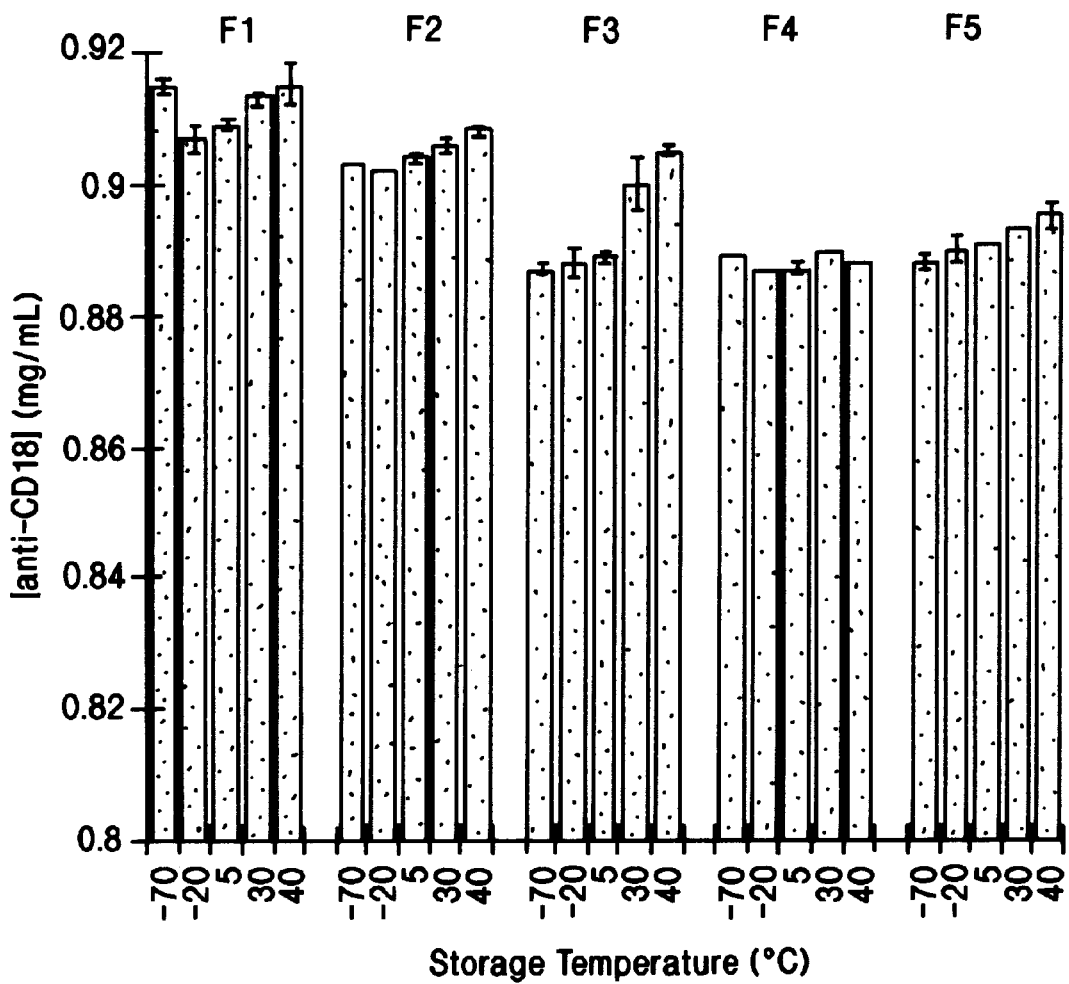
FIG. 4 shows the effect of storage temperature on protein concentration of rhuMAb CD18 formulations measured by absorbance at 278 nm corrected for vehicle absorbance at 320 nm.

UV Spectroscopy: Spectroscopic analysis of the samples was done to measure protein concentration as well as to measure light scattering as indicated by an increase in average absorbances in the range of 340 to 360 nm, or by a decrease in the ratio of the absorption maxima at 278 nm and the minima at 252 nm. FIGS. 3A and 3B show a summary of the UV data. The 40° C. samples of formulation F3 were very cloudy, containing white flocculent particles. These samples were microfuged for 5 minutes at 14000 RPM and re-measured after which the scatter was still relatively high. All other samples appeared clear and colorless ($A_{340-360}<0.02$, $A_{278}/A_{252}>2.4$). The change in A278/A250 was a more sensitive indicator of scattering than the average absorbances from 340 to 360 nm, since the latter showed no storage temperature related trend (FIG. 3A), but the former showed a definite increase for the 40° C. samples (FIG. 3B). The pH 5 formulations showed a smaller change in A278/A252 ratio at 40° C. than the pH 6 formulations in every case. The protein concentrations for the pH 5 formulations were only 2–3% greater than the pH 6 formulations (FIG. 4).

pH: All formulation vehicles except F4 showed a slight increase (~0.1 units at 40° C.) in pH, compared with −70° C. controls (Table 12 below). Both pH 5 formulations showed a greater pH increase in the active samples than in the vehicles. None of the pH 6 formulations showed this difference between active and vehicle samples. In fact, the pH increase seen in the F3 and F5 vehicles was not seen in the active samples. The pH of F4 decreased slightly at higher storage temperature. The pH increase in the pH 5 samples could be explained by a loss in acetic acid concentration due to diffusion through the topper, and is not expected to be significant at 5° C.

TABLE 12

Formulation pH after 5 weeks storage.

| Sample | pH of Vehicle | pH of Active (both vials shown) |
|---|---|---|
| F1 at −70° C. | 4.892 | 5.009/5.026 |
| F1 at −20° C. | 4.894 | 5.028/5.035 |
| F1 at 5° C. | 4.947 | 5.077/5.082 |
| F1 at 30° C. | 5.040 | 5.154/5.164 |
| F1 at 40° C. | 5.045 | 5.171/5.171 |
| F2 at −70° C. | 5.037 | 5.179/5.089 |
| F2 at −20° C. | 5.041 | 5.096/5.101 |
| F2 at 5° C. | 5.098 | 5.151/5.153 |
| F2 at 30° C. | 5.134 | 5.192/5.213 |
| F2 at 40° C. | 5.136 | 5.242/5.215 |
| F3 at −70° C. | 6.123 | 6.164/6.154 |
| F3 at −20° C. | 6.162 | 6.155/6.138 |

TABLE 12-continued

Formulation pH after 5 weeks storage.

| Sample | pH of Vehicle | pH of Active (both vials shown) |
|---|---|---|
| F3 at 5° C. | 6.160 | 6.130/6.086 |
| F3 at 30° C. | 6.204 | 6.138/6.090 |
| F3 at 40° C. | 6.214 | 6.098/6.075 |
| F4 at −70° C. | 5.964 | 6.014/6.016 |
| F4 at −20° C. | 6.017 | 6.050/6.019 |
| F4 at 5° C. | 6.021 | 6.004/5.988 |
| F4 at 30° C. | 5.928 | 5.914/5.897 |
| F4 at 40° C. | 5.880 | 5.849/5.854 |
| F5 at −70° C. | 5.653 | 5.751/5.754 |
| F5 at −20° C. | 5.729 | 5.761/5.766 |
| F5 at 5° C. | 5.727 | 5.768/5.777 |
| F5 at 30° C. | 5.797 | 5.843/5.833 |
| F5 at 40° C. | 5.812 | 5.822/5.831 |

The pH 5 formulations showed a small increase in pH at higher storage temperatures for the vehicles and active samples. Formulations F3 and F5 showed increasing pH in the vehicles with higher storage temperature, but the active samples did not show this increase. Formulation showed a slight reduction in pH.

Figure 5A:
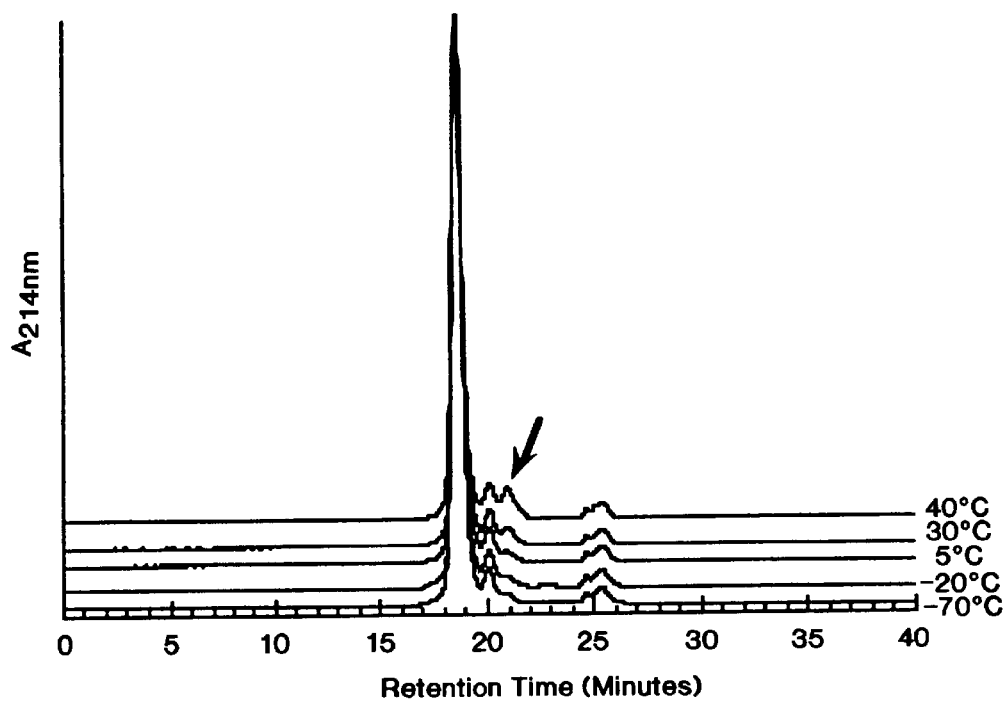
FIGS. 5A and 5B depict the effect of storage temperature on the stability of rhuMAb CD18 formulation F2 (FIG. 5A) and formulation F5 (FIG. 5B) assayed by size exclusion chromatography (SEC). A smaller MW species (see arrows) appeared which was more pronounced at pH 6 (FIG. 5B) compared to pH 5 (FIG. 5A).
Figure 5B:
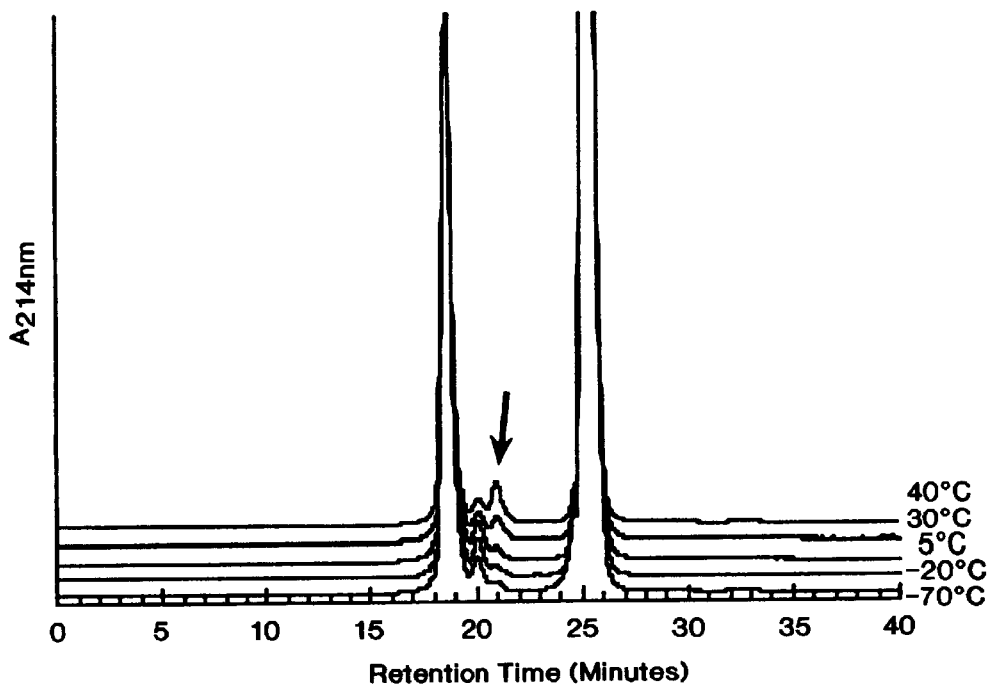
Figure 6A:
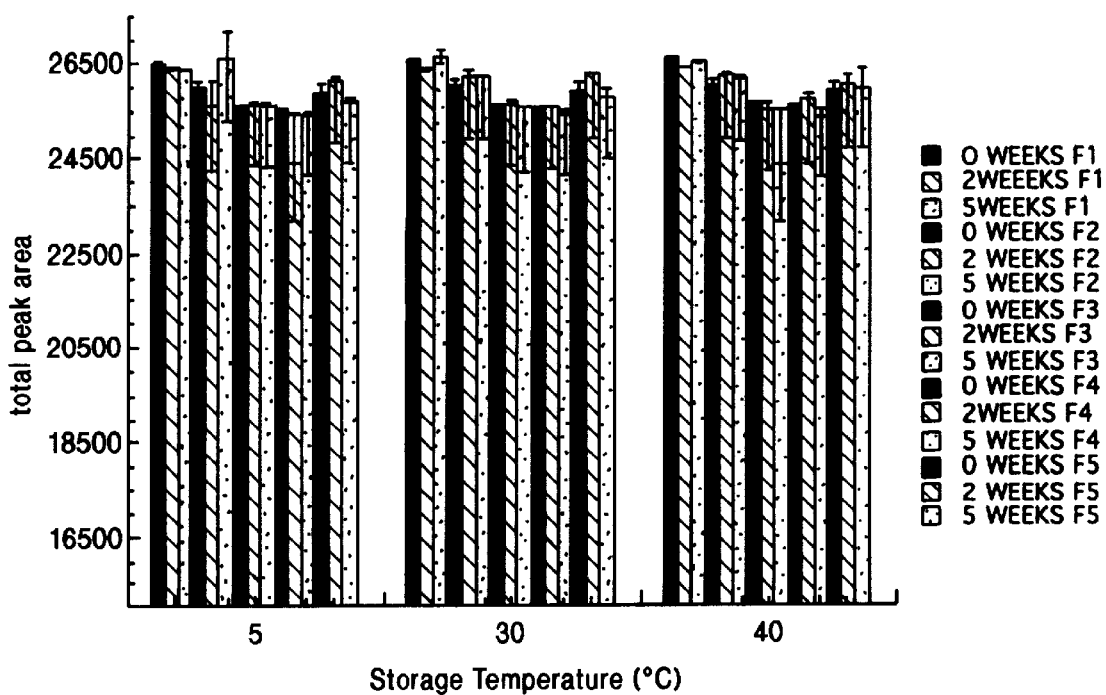
FIGS. 6A and 6B represent the effect of storage time and temperature on the stability of rhuMAb CD18 showing total peak area (FIG. 6A), and % main peak (FIG. 6B) for all formulations, assayed by SEC. No significant change in total peak area was noted. F1 and F5 maintained the lowest % main peak.
Figure 6B:
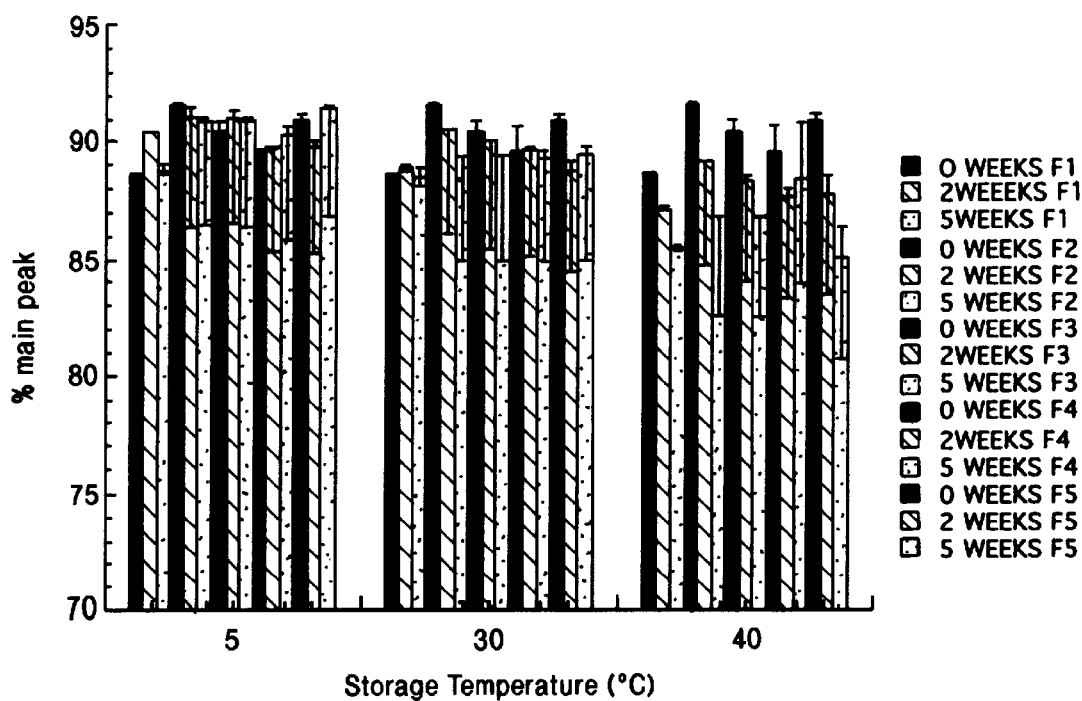

SEC: FIGS. 5A and 5B show the chromatograms for formulations F2 (FIG. 5A) and F5 (FIG. 5B). The main peak of rhuMAb CD18 eluted at 18.6 minutes, corresponding to an apparent MW of ~70,000 D. There were two major impurity peaks that eluted after the main peak, and the one at 20.9 minutes increased considerably with increasing time and storage temperature. The increase in the peak at 20.9 minutes was much more pronounced in F5 (FIG. 5B) compared to F2 (FIG. 5A), without being limited to any one theory, most likely due to the higher pH of F5. FIGS. 6A and 6B show graphs of the total peak area and the % main peak for all of the formulations after 0, 2 and 5 weeks of storage at 5, 30 and 40° C. The total peak areas for formulations F3 and F4 were significantly lower than the other three formulations.

Figure 7:
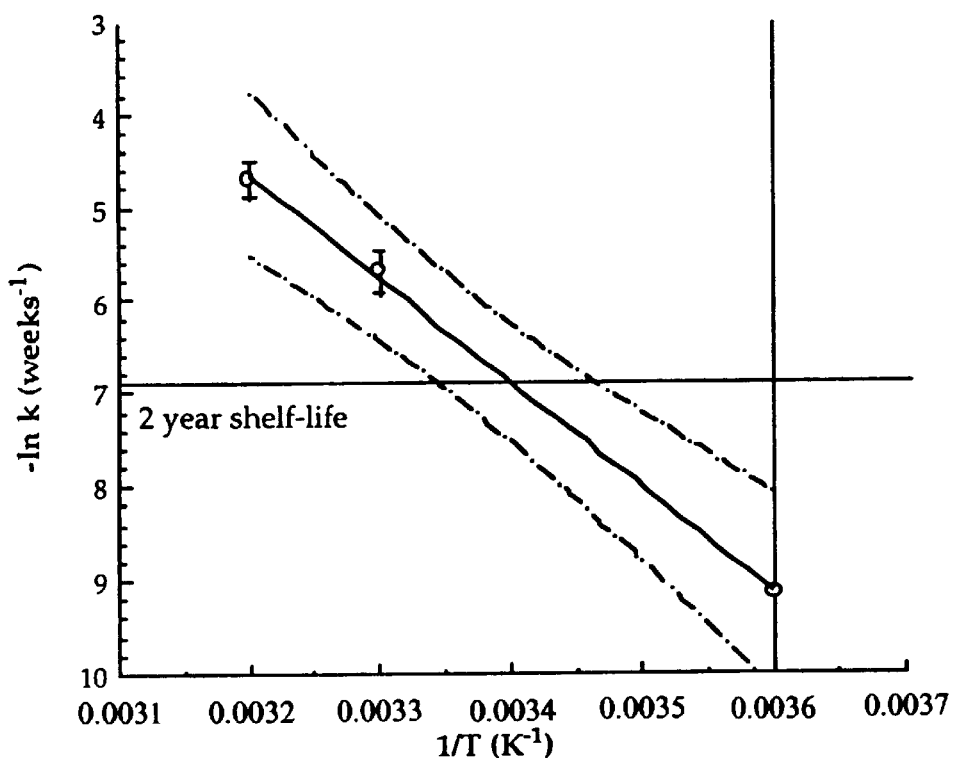
FIG. 7 is an Arrhenius plot of the % main peak area from SEC of rhuMAb CD18 formulated in acetate with trehalose at pH 5 (F2). Activation Energy=19±6 kcal/mole.

Since the lower pH formulations showed the greatest stability, rate data from the % main peak of the SEC chromatogram were calculated and fitted to an Arrhenius plot. Data for F2 is shown in FIG. 7. This plot contained only two useful points since the rate constant at 5° C. had a large standard error. The activation energy obtained from these data (19±6 kcal/mol) was very similar to the one calculated from the IEX data (see FIG. 15) even without the 5° C. datum. The 95% confidence intervals to the curve fit predict a shelf-life from 6 to 60 years at 5° C.

Figure 8:
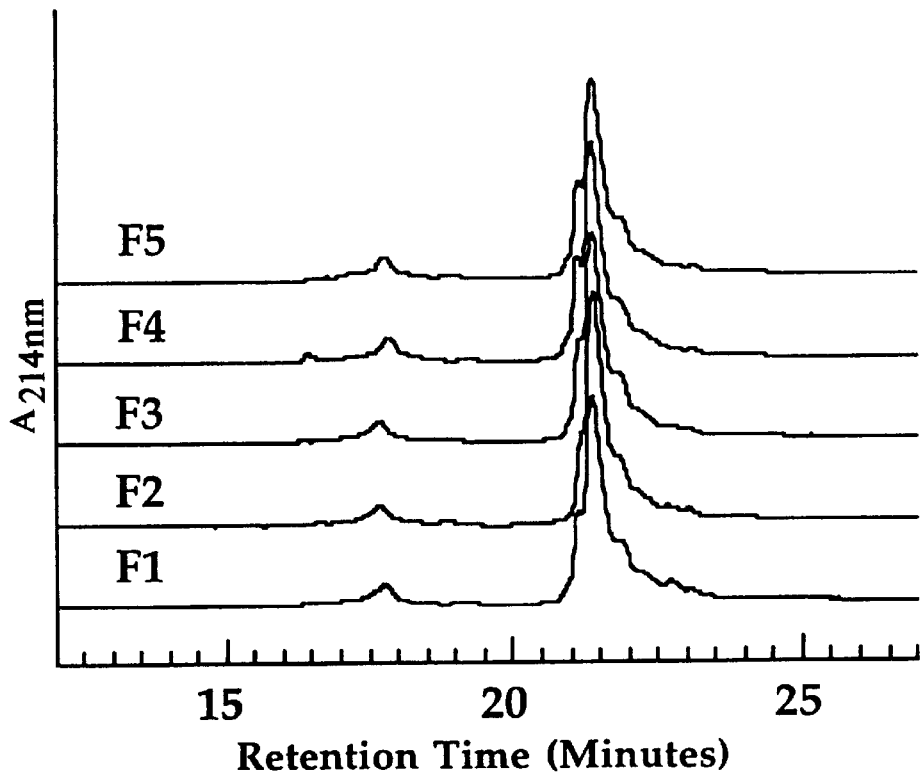
FIG. 8 shows the effect of storage for 5 weeks at 40° C. on different rhuMAb CD18 formulations, assayed by hydrophobic interaction chromatography (HIC). The early eluting peaks at 17.5 min and the shoulder at the leading edge of the main peak increased compared to controls at −70° C. F2 showed the least increase in both components (see FIG. 9).
Figure 9:
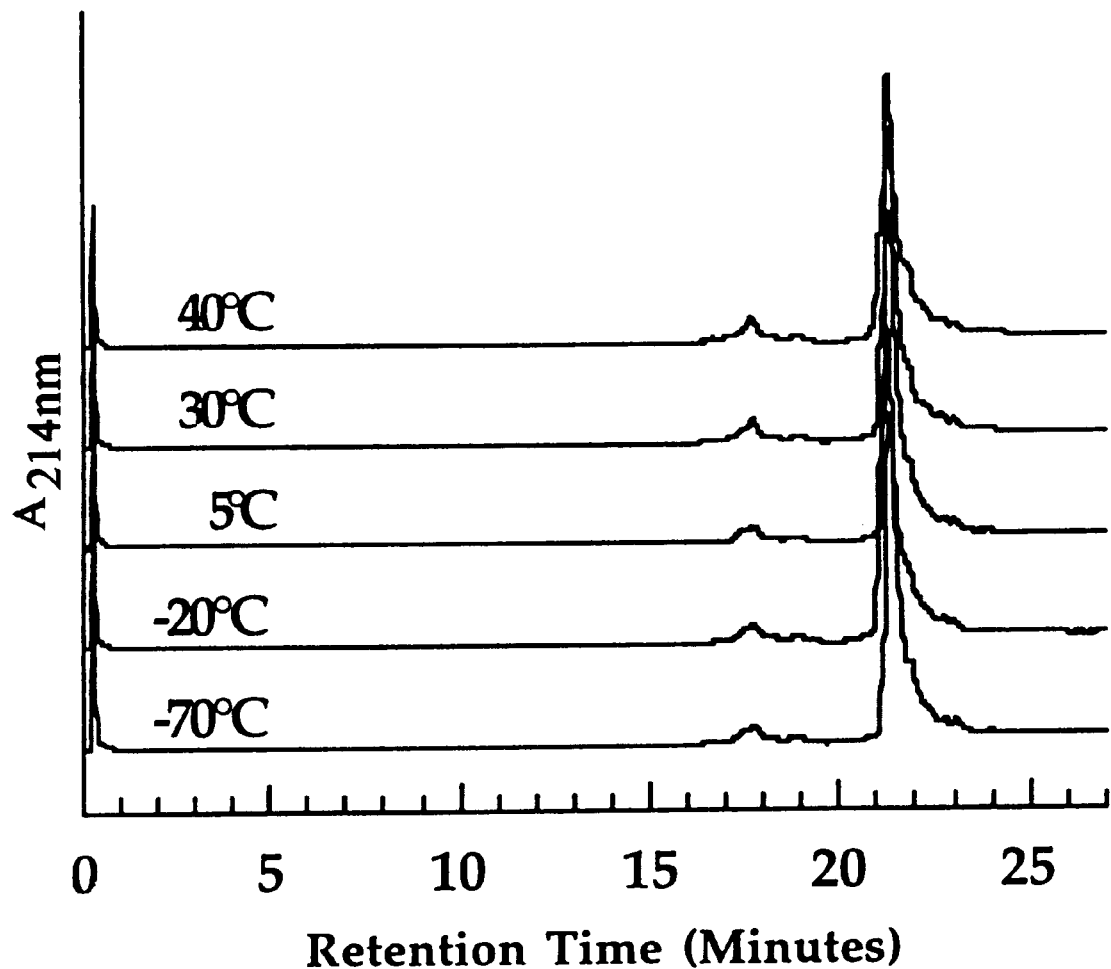
FIG. 9 shows the effect of storage for 5 weeks at different temperatures on formulation F2, assayed by HIC. A pre-main peak became apparent compared to −70° C. control.
Figure 10:
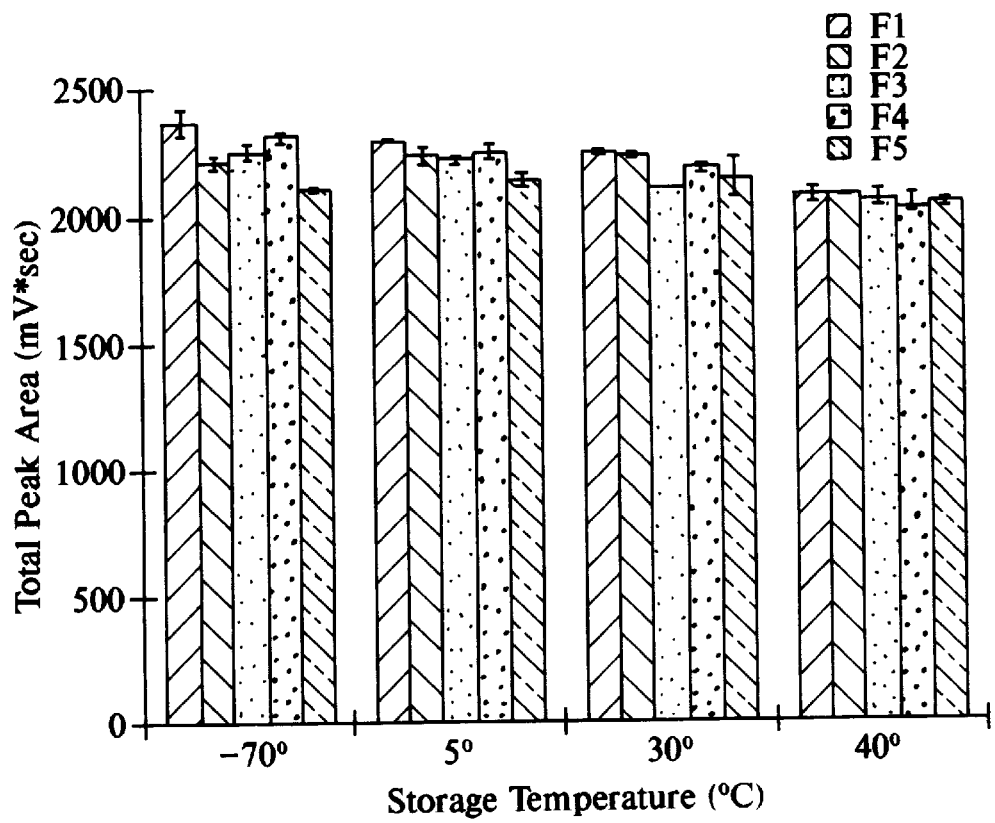

HIC: This assay was performed at a column temperature of 50° C. rather than 55° C. to improve protein recovery (from ~30% to nearly 90%), unfortunately at the expense of loss in resolution. HIC analysis of the stability samples showed an increase in a poorly resolved peak on the leading shoulder of the main peak, as well as an increase in a 17.5 min peak with increasing storage time and temperature for all formulations (FIG. 8). The shoulder was in a position that would be consistent with an oxidized form of the protein, though in preliminary assessment no peaks corresponding to an oxidized species appeared by peptde mapping. F2 showed the smallest increase in this leading peak (FIG. 9). A trend towards reduced recovery (total area) was also seen with increasing storage temperatures, with all formulations showing the same total area at 40° C. (FIG. 10). Formulations F2 and F5 showed the least change in total area at 5 and 30° C. relative to the starting −70° C. sample. This method was not stability indicating because the resolution between the degradation peak at 17.5' and the main peak is too low for accurate quantitation, and the recovery from the method is poor.

Figure 11:
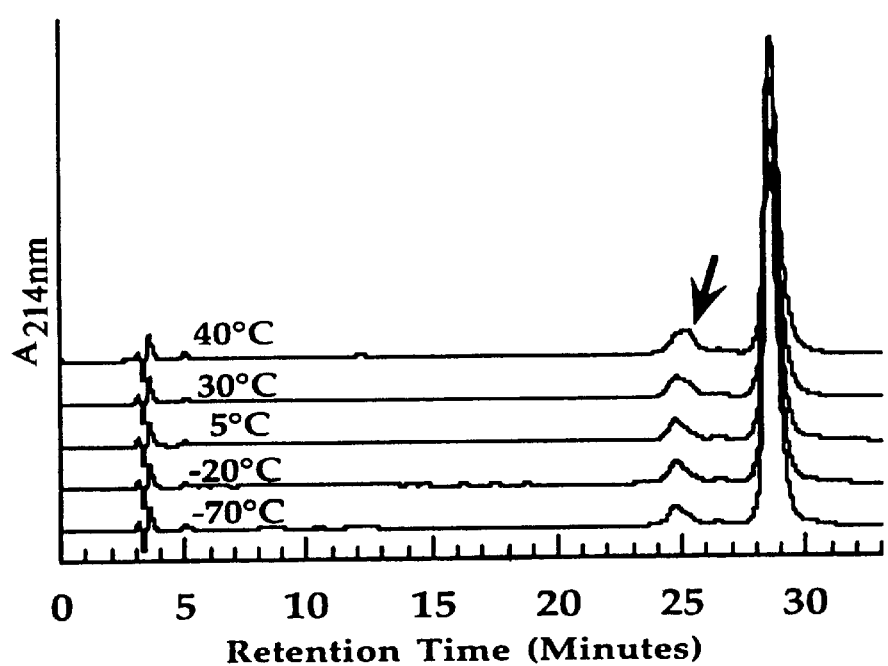
FIG. 11 shows the effect of storage for 5 weeks at different temperatures on formulation F2, assayed by reverse phase-hydrophobic liquid chromatography (RP-HPLC). A small partially resolved pre-main peak component (see arrow) increased at higher temperatures, while its slightly earlier eluting neighbor remained unchanged.
Figure 12:
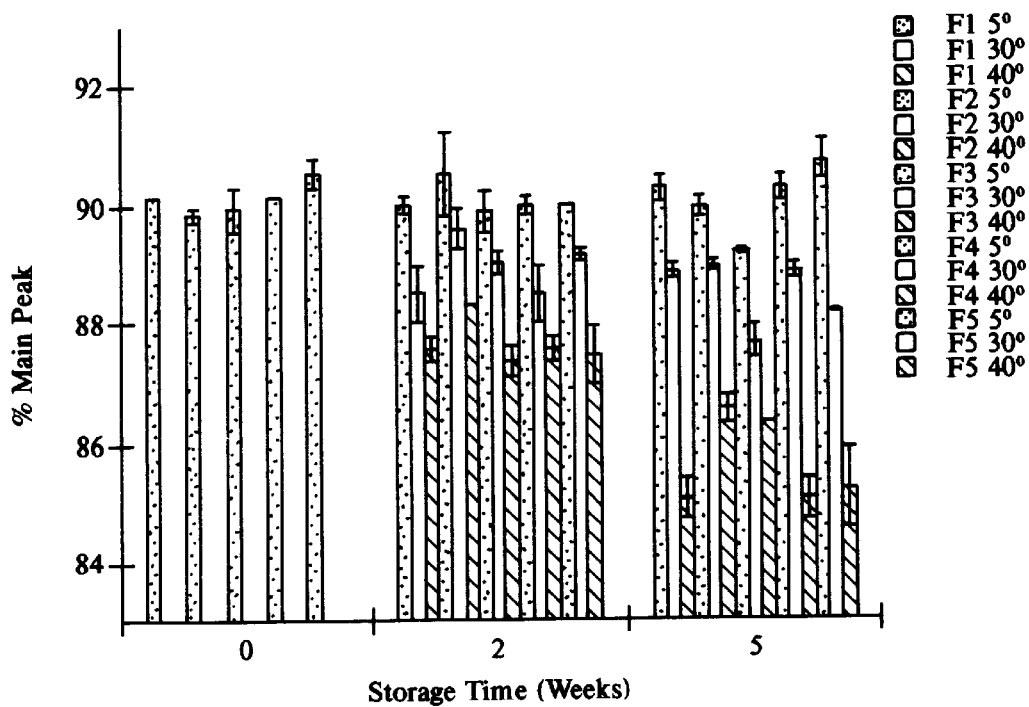
FIG. 12 shows the effect of storage for 5 weeks on the stability of rhuMAb CD18 assayed by RP-HPLC showing percentage of the main peak. F2 and F3 showed the highest % main peak after 5 weeks at 40° C.

RP-HPLC: The only change observed by RP-HPLC was an increase in a peak eluting at about 25 minutes, with a corresponding reduction in the main peak area, as the storage temperature increased (FIGS. 11 and 12). The magnitude of this change was similar to that of the lower MW species seen in SEC. Based on the relative position of this peak and its area, it may correspond to the low MW species. Formulation F2 showed the least change in the % main peak area with increasing temperature. Samples reduced with DTT were also run on RP-HPLC to increase the chance that an oxidized form might be resolved from one of the separated smaller subunits of the antibody. No difference was seen between the stored samples and the −70° C. control samples with this method.

Figure 13:
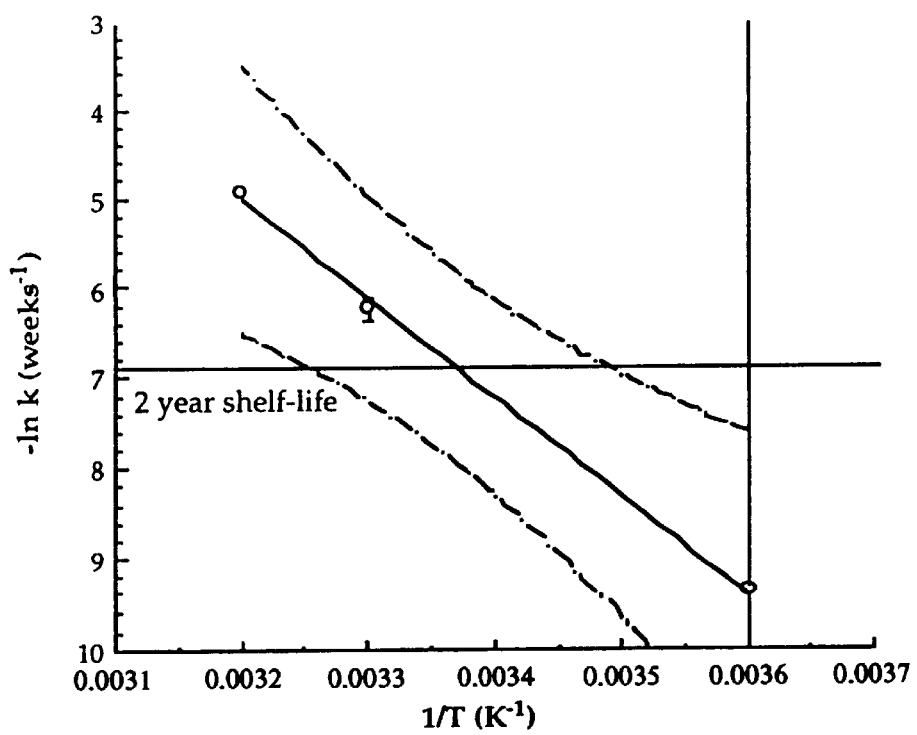
FIG. 13 is an Arrhenius plot based on the RP-HPLC % main peak for formulation F2. Activation energy (~20 kcal/mole) was only approximated from these data due to the very small K for 5° C., it appears similar to that obtained with the SEC and ion-exchange HPLC (IEX) assays.

The Arrhenius plot of the RP-HPLC kinetic data for formulation F2 gave a similar activation energy (21±1 kcal/mole) to the SEC and IEX results (19–20 kcal/mole) (FIG. 13). The shelf-life indicated by the 95% confidence intervals to the curve fit is 4 to 150 years at 5° C.

Figure 14A:
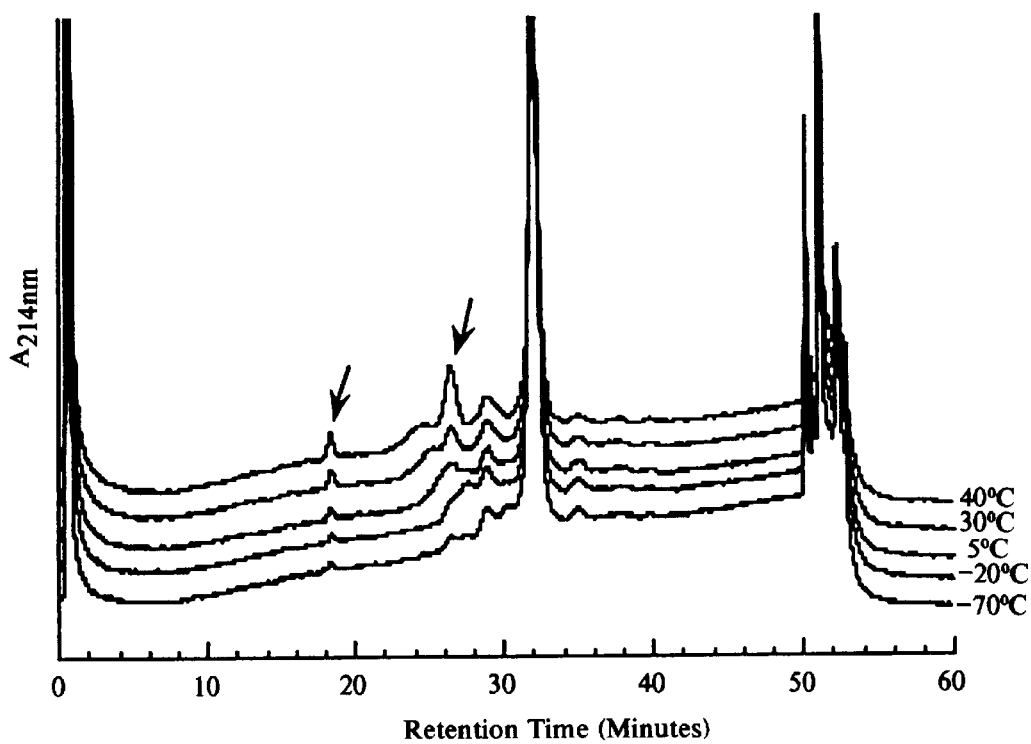
FIGS. 14A and 14B show the effect of storage temperature on the stability of rhuMAb CD18, assayed by IEX, on formulation F2 at pH 5 (FIG. 14A) and F5 at pH 6 (FIG. 14B). Two pre-main peaks increased with increasing time and temperature, more pronounced at pH 6. A hump from 22 to 28 minutes is an artifact due to an impurity washing off the column.
Figure 14B:
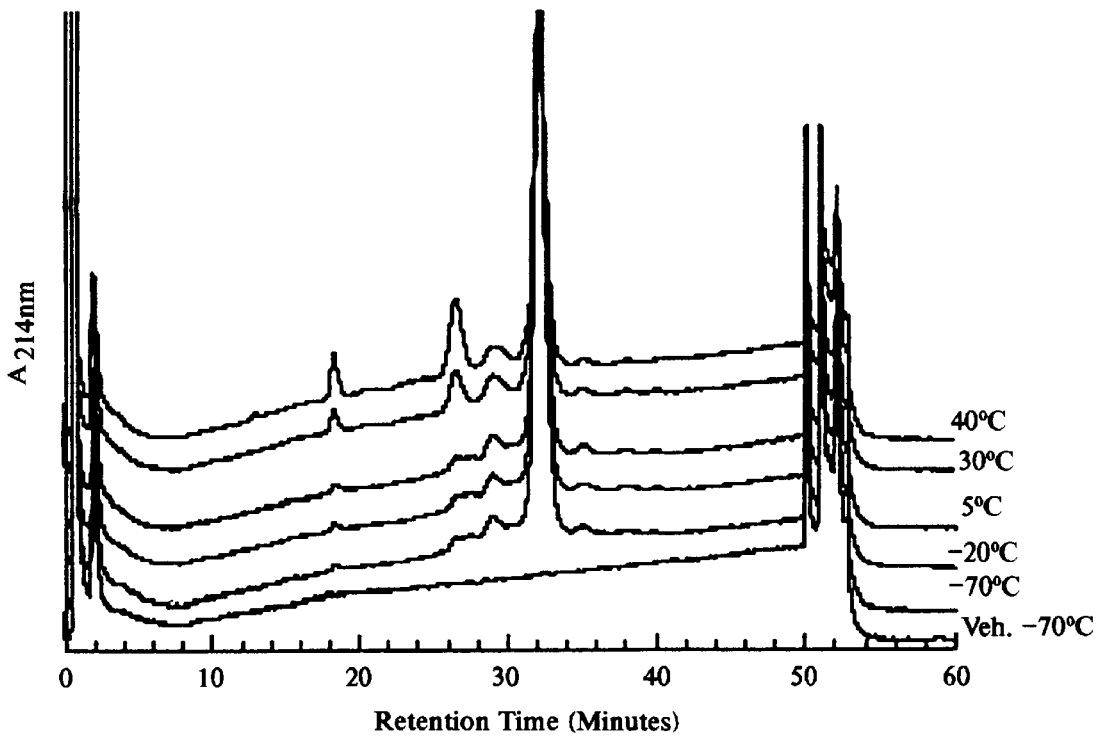

IEX: By this assay, earlier eluting peaks with retention times of 18.4 and 26.6 minutes increased with increasing storage temperature. As shown in FIGS. 14A and B which represent formulations F2 and F5, respectively, there was a more pronounced increase of these peaks in F5, compared to F2. Also the peak at 19.5 minutes became broader at higher temperatures. Based upon chromatographic changes seen upon exposure of samples to pH 11 (see below), this method should readily detect changes such as deamidation and/or disulfide scrambling, both of which can be induced at alkaline pH.

Table 13 below shows the first order rate constants for the 5 formulations at 5, 30, and 40° C.

TABLE 13

First order rate constants (κ ± SE; n = 2) for all formulations based on % main of IEX

| Formulation | 5° C. | 30° C. | 40° C. |
| --- | --- | --- | --- |
| F1 | 0.00064 ± 0.0021 | 0.0083 ± 0.0014 | 0.0299 ± 0.0023 |
| F2 | 0.0065 ± 0.0023 | 0.0091 ± 0.0025 | 0.0245 ± 0.0040 |
| F3 | −0.0004 ± 0.0008 | 0.0143 ± 0.0010 | 0.0432 ± 0.0019 |
| F4 | −0.00066 ± 0.00073 | 0.0137 ± 0.00033 | 0.0413 ± 0.00022 |
| F5 | −0.00010 ± 0.00082 | 0.0129 ± 0.00095 | 0.0439 ± 0.0017 |

Figure 15:
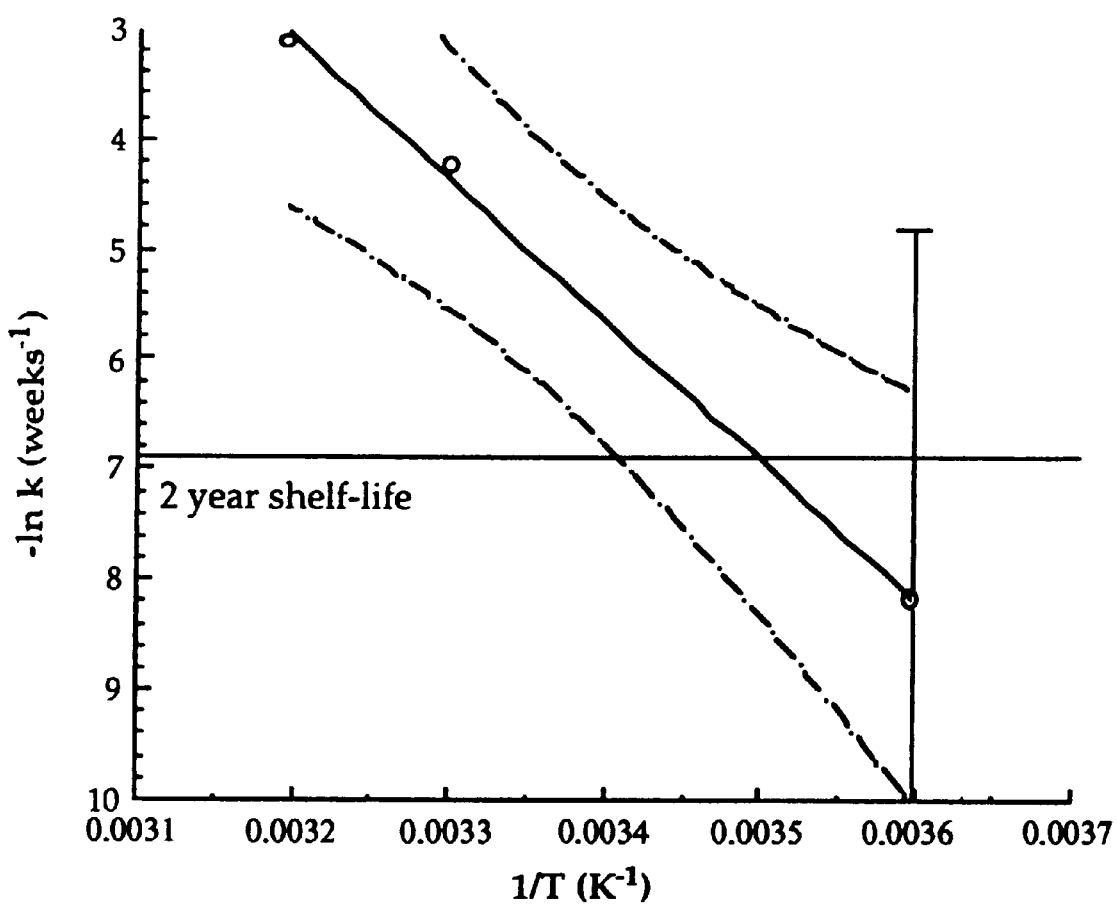
FIG. 15 is an Arrhenius plot of the % main peak area from IEX of rhuMAb CD18 formulated in acetate with trehalose at pH 5 (F2). Activation Energy=20±10 kcal/mole.

Formulations F1 and F2 are clearly better than the other formulations, implying that the major degradation process is base catalyzed. An Arrhenius plot based on the % main peak area predicted an activation energy of 19.8±9.9 kcal/mole for F2 and a $t_{90}$ of 50±25 months (95% confidence intervals) at 5° C. (FIG. 15). Receptor binding activity: Table 14 below shows the specific activity for each temperature and formulation after 5 weeks storage. The specific activity was calculated by dmding the MAC-1 capture assay concentration by the total F(ab')$_2$ ELISA concentration. The standard error shown is for n=2 and accounts for the total propagated error from the two different assays for 2 vials at 3 dilutions each. There was a clear trend for all formulations towards a lower specific activity at higher storage temperatures (~10–15% loss at 40° C.); all formulations showed about the same extent of loss at 40° C. relative to ~70° C. The p value from one way ANOVA analysis of the 40° C. data for the different formulations is 0.98, so the 40° C. means would not be considered significantly different from each other, within 95% confidence. An unpaired t-test of the 40° C. data versus the 30° C. data shows that the difference is significant (p=0.044) and the lower temperatures are even more significantly different by this method (p<0.02).

TABLE 14

| Storage | F1 | | F2 | | F3 | | F4 | | F5 | |
| --- | --- | --- | --- | --- | --- | --- | --- | --- | --- | --- |
| Temp (° C.) | mean | SE | mean | SE | mean | SE | mean | SE | mean | SE |
| −70 | 0.976 | 0.098 | 0.906 | 0.140 | 1.008 | 0.112 | 0.952 | 0.116 | 0.918 | 0.433 |
| −20 | 0.978 | 0.123 | 0.903 | 0.157 | 0.946 | 0.152 | 0.871 | 0.072 | 0.865 | 0.209 |
| 5 | 0.982 | 0.157 | 0.898 | 0.177 | 1.023 | 0.166 | 0.919 | 0.203 | 0.886 | 0.350 |
| 30 | 0.923 | 0.067 | 0.878 | 0.189 | 0.949 | 0.076 | 0.868 | 0.109 | 0.885 | 0.340 |
| 40 | 0.866 | 0.113 | 0.817 | 0.227 | 0.904 | 0.115 | 0.817 | 0.093 | 0.772 | 0.198 |

IEF: The effect of storage for 5 weeks at different temperatures was assayed by isoelectric focusing electrophoresis (IEF) for formulations F2 and F5. The major band appeared to have a pI of ~8.8. Three main components at pI's ~8.75 (second most intense band), ~8.6, and ~8.4 were also seen, which increase slightly with storage, particularly at pH 6. The 30 and 40° C. samples showed conversion to the more acidic bands. For the 40° C. samples, the bands at pI 8.8 and 8.75 had approximately equal intensity and there was no discernible difference between the formulations in this regard. There were at least two more acidic bands (pI's ~8.6 and ~8.4), which had at least 4-fold lower intensity than the two most basic bands. These bands did not seem to change in intensity with storage.

SDS-PAGE: The effect of storage temperature on the stability of rhuMAb CD18 formulations F2 and F5 (5 weeks) was assayed by SDS-PAGE (under reduced and nonreduced conditions). The rhuMAb CD18 appeared at a MW of ~120 kD on the non-reduced gel. In the starting bulk there were several minor bands at higher molecular weight than the main band which may represent rhuMAb CD18 with various portions of the leucine-zipper segment sill attached. Several percent of this impurity is known to be present in this bulk preparation. There were several bands of lower MW than the main band, but only one of these bands seemed to change in any of the formulations, or with temperature. The band at around 45 kD increased with temperature and seemed slightly more intense in pH 6 than in pH 5 formulations. This observation was consistent with SEC data. The band just above the ~45 kD band on the non-reduced gels corresponded in apparent molecular weight with the band seen on the reduced gels and may represent a non-reducing contaminant protein. All species converted to two bands, corresponding to light and heavy chain, upon reduction with dithiothreitol, suggesting the absence of any proteolytic cleavage. MALDI-TOF MS (Yates, *J. Methods Enzymol.*, 271:351–377 (1996)) confirmed formation of fragments that were the size of Fab'.

Figure 17:
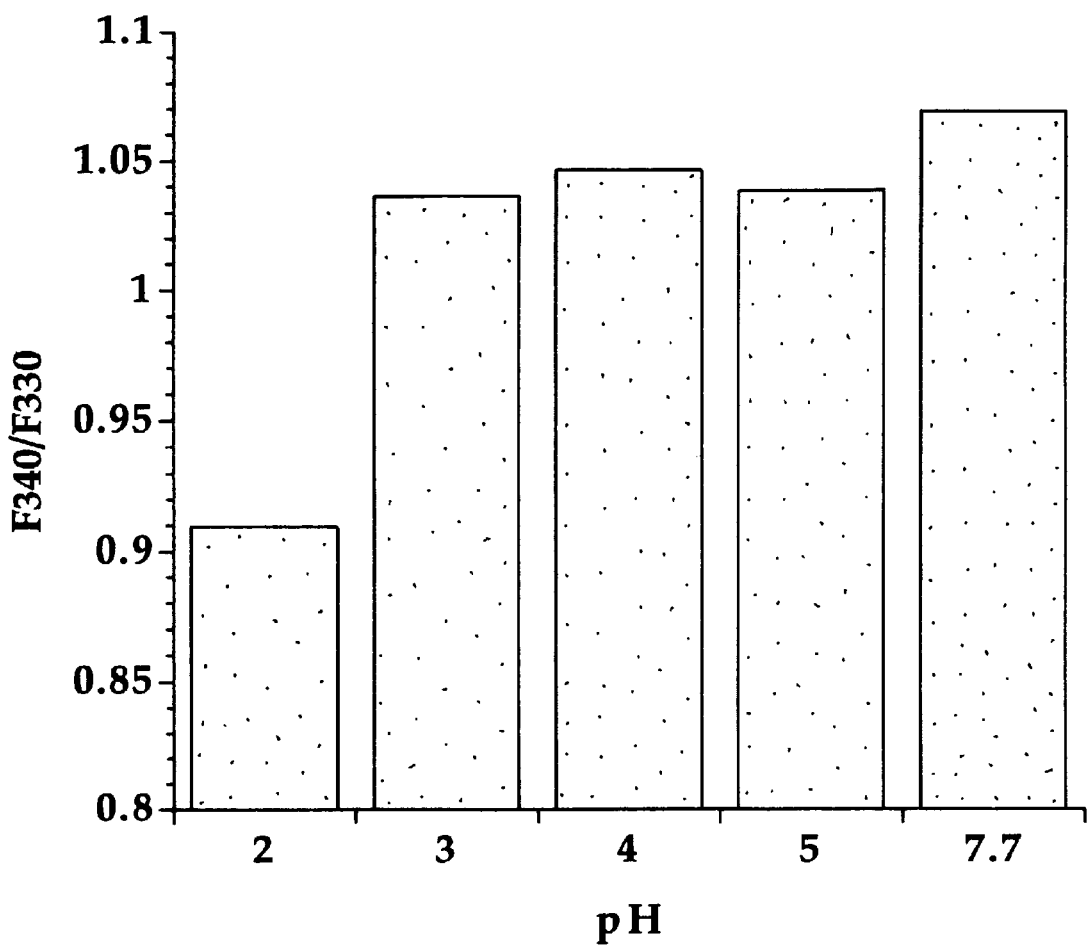
FIG. 17 shows fluorescence spectroscopy of rhuMAb CD18 formulations. The emission spectra of various formulations were obtained on an SLM8000 fluorimeter, using 280 nm excitation wavelength. 500 µL samples were placed in quartz cuveftes and spectra were obtained with a 2nm bandwidth at 22° C. Samples were prepared at the different pHs by dilution of a concentrated stock to 0.1 mg/mL protein and analyses were made after 24 hr at 25° C. The antibody is conformationally stable above pH 3.

Formulation pH and protein concentration: The effect of pH on the conformation of rhuMAb CD18 was investigated using fluorescence spectroscopy (FIG. 17). The protein appeared to lose tertiary structure below pH 3, but is unchanged in the range of pH 3 to 8.

Figure 18A:
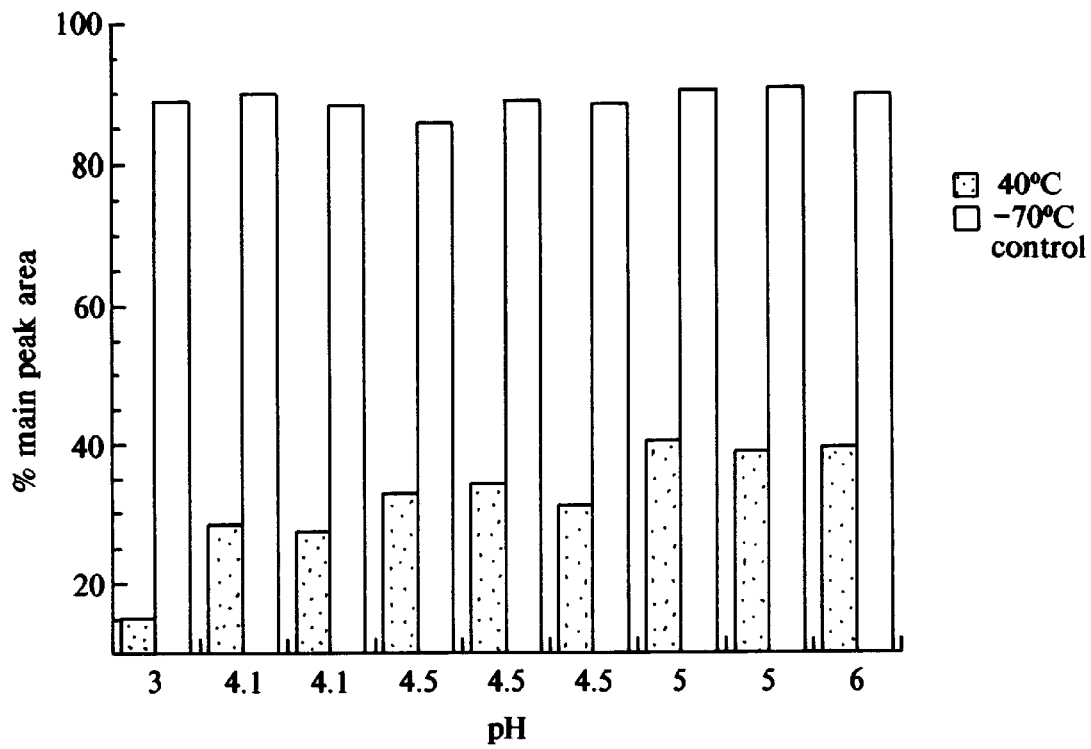
FIGS. 18A and 18B depict the effect of pH and protein concentration on the stability of rhuMAb CD18. Formulations in the pH range of 3 to 6 and concentration range of 0.5 to 25 mg/mL were placed on stability at 40° C. and −70° C. for 2 months. Analyses were made by IEX (FIG. 18A) and SEC (FIG. 18B). pH 5 was found to be the preferred pH, irrespective of protein concentration.
Figure 18B:
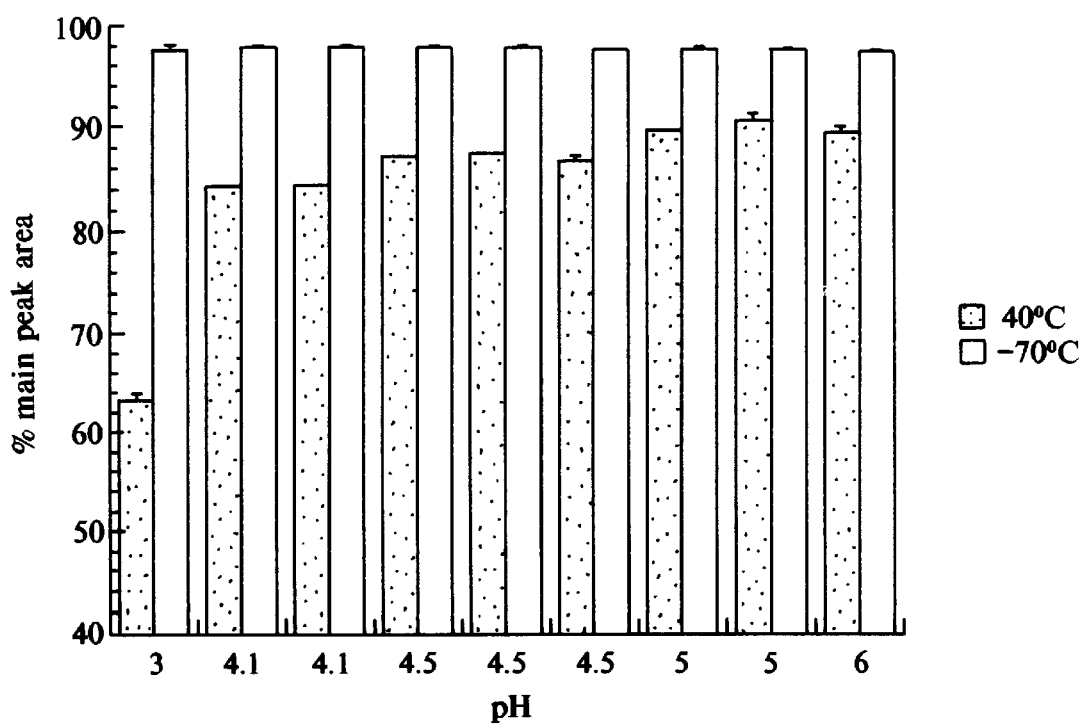

Based on the above observation, the effect of pH and protein concentration on the stability of rhuMAb CD18 was then investigated using a central composite design protocol. Formulations containing 10 mM Na citrate, 8% trehalose, 0.05% TWEEN 20™ containing one of the following conditions were prepared: 0.5 mg/mL (pH 4.5), 5 mg/mL (pH 3, 4.5, 6), 10 mg/mL (pH 4, 5), 25 mg/mL (pH 4.5). Samples were placed at 40° C. and −70° C., and analyzed after 2 month by IEX (FIG. 18A) and SEC (FIG. 18B). Again, pH 5 was found to be the most stable condition for the protein, irrespective of protein concentration.

Figure 19A:
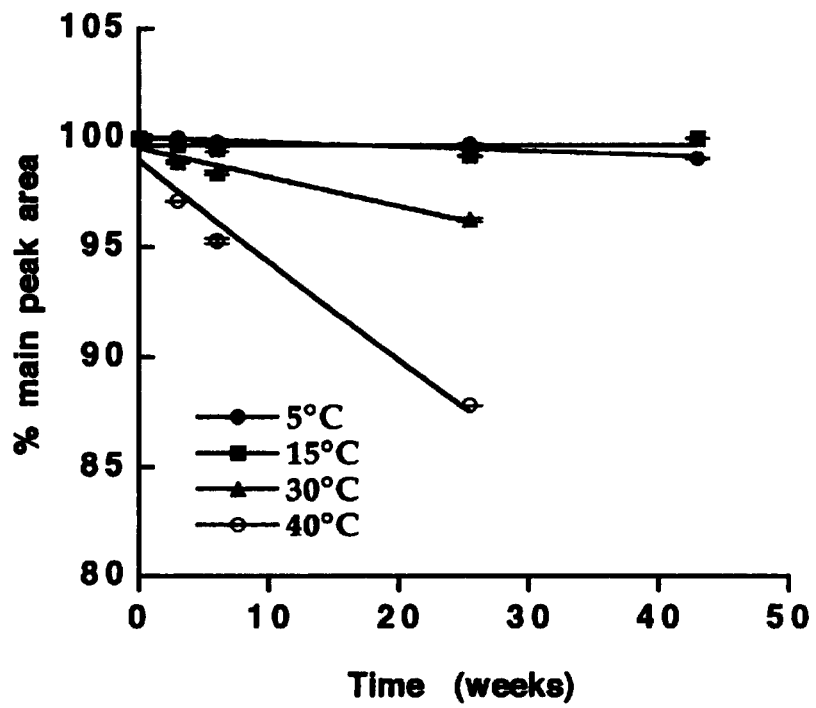
FIGS. 19A, 19B and 19C depict the kinetics of degradation of rhuMAb CD18 by SEC (FIG. 19A), IEX (FIG. 19B) and MAC-1 binding (FIG. 19C) at various temperatures. Duplicate samples in 10 mM Na acetate, 8% trehalose, 0.01% TWEEN 20™, pH 5 were prepared in 3 cc glass vials and placed on stability at the indicated temperatures.
Figure 19B:
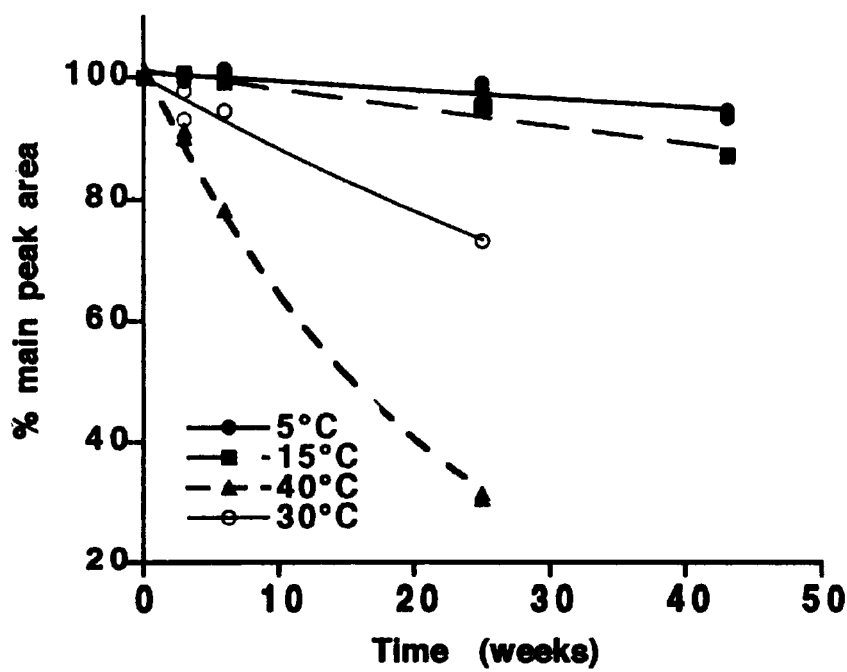
Figure 19C:
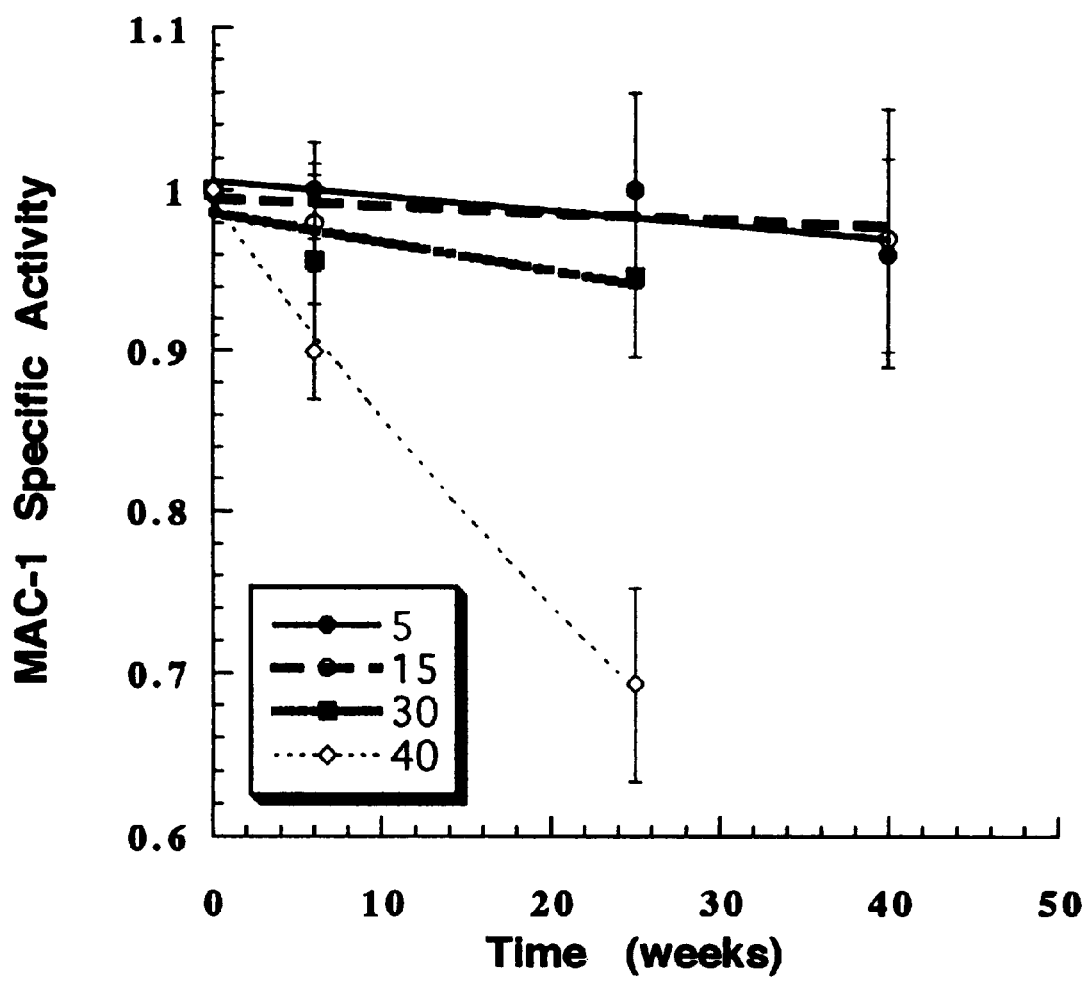

Long Term Stability of rhuMAb CD18 Formulation: To address the long term stability of the F2 formulation, duplicate samples in 10 mM Na acetate, 8% trehalose, 0.01% TWEEN 20™, pH 5 were prepared in 3 cc glass vials and placed on stability at the indicated temperatures. Analysis by SEC (FIG. 19A) and MAC-1 binding (FIG. 19C) indicates no change in the size distribution, aggregation state, or bioactivity of the protein for up to 43 weeks at 5° C; stability up to ~1 mo at 30° C. is indicated. IEX shows formation of acidic peaks (~1% after 43 weeks) that were identified to be deamidation by peptde mapping/MS (FIG. 19B).

CONCLUSIONS

Preliminary data suggested that the primary reaction in the purified rhuMAb CD18 was cleavage to species approximately half the MW of the starting material, and that this reaction, as well as generation of acidic peaks on IEX and earlier eluting peaks on HIC and RP-HPLC, were all minimized at pH 5 (compared to pH 6), and in trehalose (compared to salt or mannitol). The smaller MW species may have been formed either by proteolytic cleavage and/or by disulfide scrambling, both of which may be enhanced at higher pH's. Reduction of the control and degraded samples led to only the light and heavy chains, consistent with either the cleavage to Fab, or mixed disulfide formation between heavy and light chains.

RhuMAb CD18 appeared to be least stable in salt formulations; at pH 5 a larger aggregate (equivalent to a trimer) appeared and at pH 6 precipitation was noted at 40° C. Without being bound to any one theory, one possible explanation is that NaCl does not provide hydrogen bonding, as sugars and mannitol do, which could potentially prevent self-association of this antibody at higher temperatures.

Based on the above preliminary data from the primary assays (IEX, SEC, and UV), the preferred aqueous formulation for rhuMAb CD18 is 10 mM sodium acetate, 8% trehalose wN, 0.01% TWEEN 20™, pH 5.0. The shelf-life predicted from an Arrhenius fit to the first order rate constants (IEX data) is 1.7 to 4 years at 5° C. (95% confidence intervals).This formulation can be prepared by mixing 0.573 mL glacial acetic acid, 0.403 mL concentration NaOH, 80 g trehalose, 1 mL of a 10% TWEEN 20™ solution and making up to 1 L with MilliQ water (pH 5.0±0.1 at the 2 L scale). Conductivity of this formulation was found to be 502±10% microSiemens/cm using a Radiometer-Copenhagen CDM-83 with a CDC 314 probe, and density was 1.017 g/mL.

EXAMPLE 2

This example describes the production of a stable aqueous multdose formulation comprising a recombinant humanized anti-CD20 antibody, rhuMAb CD20. Acetate (pH 5) formulations stored at 40° C. for one month demonstrated greater stability than those samples formulated in histidine (pH 5 or 6). The histidine formulations after accelerated temperature storage became very opalescent and yellow in color. A buffering capacity of 10–30 mM acetate was sufficient to maintain the pH at 5.0. The effective amount of tonicity modifier needed to stabilize the antibody against freeze or thermal induced aggregation was compared using sodium chloride (NaCl) or trehalose. Trehalose was found to protect the formulation from freeze induced aggregation, particularly at levels >134 mM (500:1 molar ratio). The trehalose formulations (67–270 mM) were much more effective than NaCl in stabilizing formulations placed at 40° C. as evidenced by the clarity of the solution. These results led to the development of a stable prototype liquid multidose formulation comprising 40 mg/mL rhuMAb CD20, 25 mM acetate, 150 mM trehalose, 0.9% benzyl alcohol, 0.02% polysorbate 20 at pH 5.0 that has a minimum shelf life of two years storage at 2–8° C.

MATERIALS AND METHODS

RhuMAb CD20: The bulk material used in all studies was composed of 27 mg/mL rhuMAb CD20 in 50 mM Tris and 100 mM sodium chloride at pH 7.5 or 2.7 mg/mL rhuMAb CD20 in 25 mM Tris and 50 mM sodium chloride at pH 6.0. The bulk was stored aseptically at 2–8° C. in the absence of light.

Buffer exchange: The exchange of the bulk rhuMAb CD20 into different test buffers was done by dialysis at 2–8° C. using Spectra/Por® 7 membranes (MWCO=8 Kda) which were rinsed thoroughly with deionized water before use. One volume of antibody was dialyzed against a minimum of 10 volumes of the appropriate test buffer. This process was repeated three to four times within a one day period. To obtain the final concentration of 40 mg/mL, the antibody was further concentrated using an Amicon UF/DF cell containing a YM30 membrane (MWCO=30 KDa). Due to the lower starting concentration of the 2.7 mg/mL material, this material was first concentrated to ~40 mg/mL and then dialyzed against the appropriate test buffer. After the target concentration was reached and the buffer exchange completed, trehalose, benzyl alcohol and polysorbate 20 were added to the final concentrations described in Tables 15 to 17 below. The liquid multdose C2B8 candidate formulation was 40 mg/mL rhuMAb CD20 formulated in 25 mM acetate, 150 mM trehalose, 0.9% benzyl alcohol and 0.02% polysorbate 20 at pH 5.0. The formulation was then sterile filtered through a $0.2\mu$ membrane and the concentration was determined by UV spectrophotometric scan. A 0.5 ml of each final formulation was then filled into sterile 3 cc glass vials, stoppered with teflon faced grey butyl rubber stoppers and then capped with crimp seals.

TABLE 15 pH and buffer species comparison study

| Concentration of rhuMAb CD20 (mg/mL) | Concentration of buffer species (mM) | pH | Storage Temperature (° C.) |
|---|---|---|---|
| 40 | 50 mM Acetate | 5.0 | 2–8, 40, 50 |
| 40 | 50 mM Histidine | 5.0 | 2–8, 40, 50 |
| 40 | 50 mM Histidine | 6.0 | 2–8, 40, 50 |

All formulations contain 150 mM trehalose, 0.9% benzyl alcohol and 0.02% polysorbate 20.

TABLE 16

Acetate buffering capacity study

| Concentration of rhuMAb CD20 (mg/mL) | mM Acetate | Storage temperature (° C.) |
|---|---|---|
| 40 | 10 | 2–8, 40 |
| 40 | 15 | 2–8, 40 |
| 40 | 20 | 2–8, 40 |
| 40 | 25 | 2–8, 40 |
| 40 | 30 | 2–8, 40 |

All formulations contain 150 mM trehalose, 0.9% benzyl alcohol and 0.02% polysorbate 20 at pH 5.0.

TABLE 17

Effective ratio of tonicity modifier: rhuMAb CD20 study

| Tonicity modifier | Molar ratio of sugar/salt:rhuMAb CD20 | mM trehalose or sodium chloride |
|---|---|---|
| Trehalose | 0 | 0 |
| Trehalose | 250:1 | 67 |
| Trehalose | 500:1 | 134 |
| Trehalose | 1000:1 | 267 |
| Sodium Chloride | 500:1 | 134 |
| Sodium Chloride | 1000:1 | 267 |

A). All formulations contained 40 mg/mL rhuMAb CD20, 20 mM acetate, 0.9% benzyl alcohol and 0.02% polysorbate 20 at pH 5.0.
B). A freeze-thaw comparison study was completed for the trehalose formulations. The stability of all formulations at 2–8° and 40° C. was conducted in parallel.

SEC HPLC: Samples were diluted to 10 mg/mL with formulation buffer before being assayed. The method uses a TSK G3000 SWXL column (TosoHaas) with a mobile phase consisting of 0.2M potassium phosphate, 0.25M potassium chloride, pH.7. The socratic flow rate is 0.5 mLlmin with a total run time of 30 minutes. The amount of protein injected is 200 $\mu$p and the UV absorbance at 280 nm is used as the mode of detection.

HIC HPLC: Samples were diluted to 10 mg/mL with formulation buffer before being assayed. The antibody was digested with carboxypeptidase and papain prior to analysis of the final fragments. The method uses a TSK-GEL butyl-NPR (4.6×35 mm) column. The temperature of the column is controlled at 35° C. during the assay. Elution of the antibody fragments is induced by changes in the ammonium sulfate gradient. The total run time of the assay is forty minutes and the flow rate is 1 ml/min. A protein load of 5–10 $\mu$g is injected and the detection is monitored by UV absorbance at 214 nm.

UV spectrophotometric scan: For protein concentration determination, samples were accurately diluted 1:100 with formulation buffer. The absorbance at 280, 320 and 350 were read with an Hewlett Packard 8451A diode array spectrophotometer against the same formulation buffer as blank. The protein concentration was calculated by subtracting $A_{320}$ from $A_{280}$ and dividing by an extinction coefficient of 1.7.

For turbidity evaluaton, samples were scanned without dilution on an Hewlett Packard 8451A diode array spectrophotometer and the average absorbance in the range of 340–360 nm was determined. Water was used as the blank.

Accelerated stability studies: The vials were stored upright in temperature-controlled rooms or incubators at 2–8°, 30°, 40° or 50° C. Two to three vials were removed at finite times and the protein degradation monitored by the stability indicating assays (SEC HPLC, HIC HPLC, UV spectrophotometric scan to determine protein concentration and turbidity, as well as pH measurement). In addition, samples were subjected to the complement dependent cell cytotoxicity assay as described below to assess bioactvity.

Freeze-thaw studies: Samples were exposed to a minimum of two hours of freezing at –70° C. followed by a room temperature thaw (<45 minutes). Each cycle was composed of one freeze followed by one thaw excursion. Three vials were removed per formulation after one, three and five consecutive freeze-thaw cycles and the stability monitored by SEC HPLC and UV spectrophotometric scan to measure the turbidity and protein concentration.

Complemnent Dependent Cytotoxicity Assay (CDC): The bioactivity of the stability samples was determined by the CDC assay described in Gazzano Santoro et al., *J. Immunol. Meth.* 202:163–171 (1997), except that human complement (rather than rabbit complement) was used. The percent bioactvity of the test sample was determined as follows, $$\% \text{ bioactivity} = \frac{[(CDC \text{ assay mg/mL of sample}/ \text{ protein concentration of sample})]}{[(CDC \text{ assay mg/mL of reference}/ \text{ protein concentration reference})]} \times 100$$

The protein concentration of the test sample and reference control were determined by UV spectrophotometric scan.

Figure 24A:
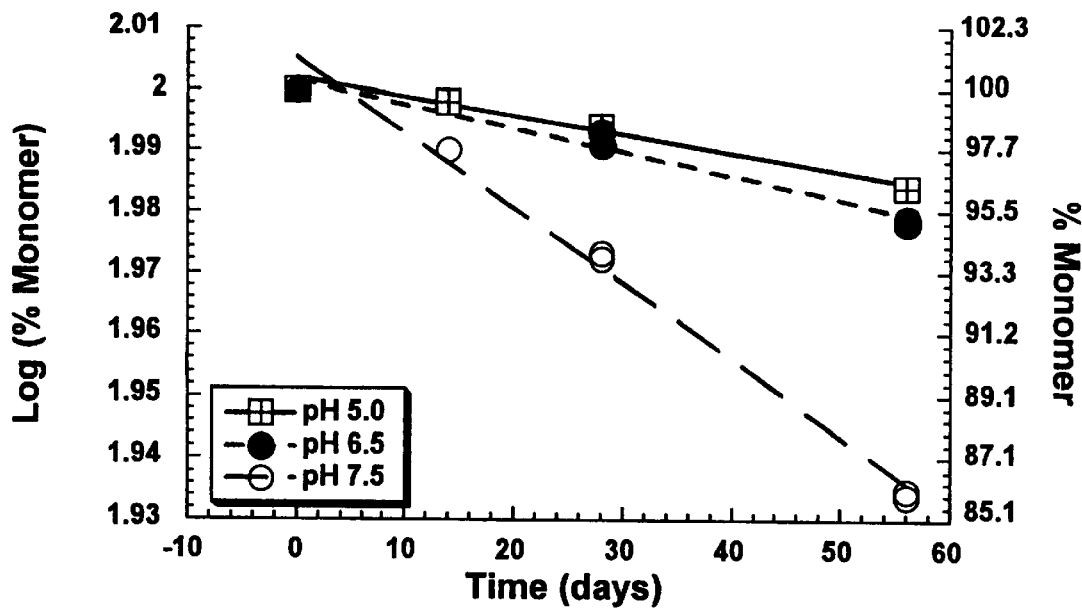
FIGS. 24A and 24B depict the effect of pH on the rate of aggregation (FIG. 24A) and oxidation (FIG. 24B) of 40 mg/mL rhuMAb CD20, 25 mM histidine, 0.02% polysorbate formulations at pH 5,6.5 or 7.5 stored at 40° C.
Figure 24B:
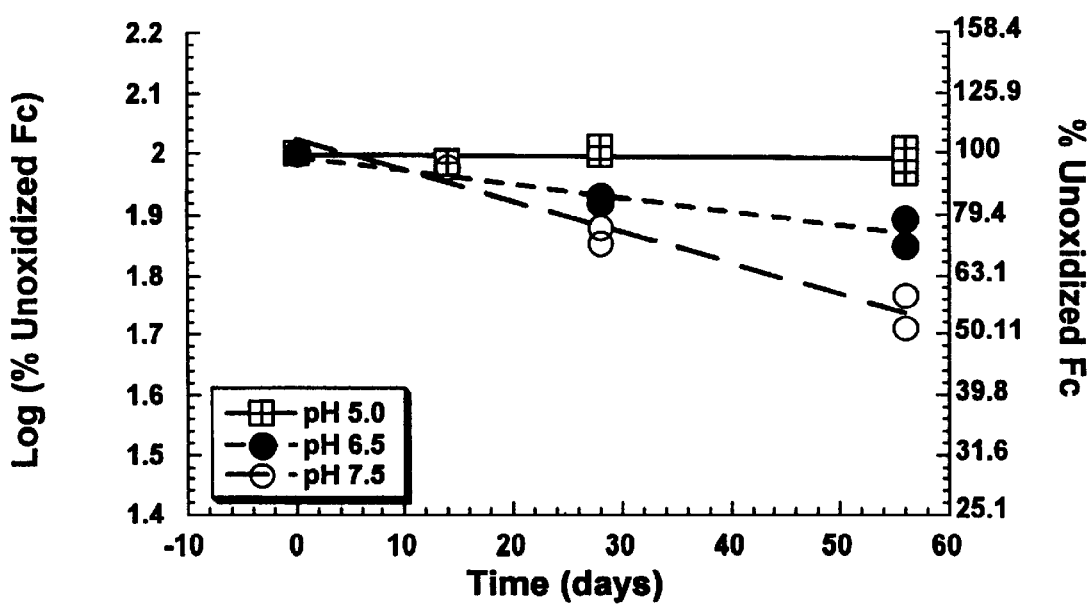

RESULTS AND DISCUSSION pH and buffer species: Decreasing the pH from 7.5 to 5.0 of 40 mg/mL rhuMAb CD20 formulated in histidine and trehalose virtually eliminated oxidation of the antibody even after two months storage at 40° C. (FIG. 24B). There is also a decline in the rate of aggregation but the difference below pH 6.5 is slight (FIG. 24A). Further reduction in aggregation rate may require a decrease in the protein concentration. A stable formulation appears to require a pH in the acidic range.

To differentate between the effect of buffer species and the effect of pH, histidine (5 or 6) and acetate (5), multdose formulations were compared after storage at 2–8°, 40° or 50° C. The samples were stored at 50° C. as a way of quickly determining the relative stability between the formulations with the caveat that the degradation observed was not necessarily predictive of that seen at 2–8° C. storage.

The visual clarity of the formulations and the turbidity as measured by UV spectrophotometric scan (340–360 nm) after four (50° C.) and eight (2–8°, 40° C.) weeks storage is described in Tab Both histidine formulations were more opalescent than the acetate at all temperatures studied. After two weeks storage at 50° C., the histdine at pH 5 had formed a solid opaque gel while the sibling formulation at pH 6 was visually cloudy and yellow in color by four weeks. The histidine formulations stored at 40° C. also turned yellow. Without being bound to any one theory, the color formation is likely due to the oxidation of histidine and is more apparent in this study due to the high concentration of histidine used (50 mM). No differences were observed at 2–8° C. storage relative to the initial timepoint.

TABLE 18

The effect of buffer species and pH on the appearance and clarity of 40 mg/mL rhuMAb CD20 multidose formulations containing 50 mM acetate or histidine, 150 mM trehalose, 0.9% benzyl alcohol and 0.02% polysorbate 20 at pH 5 or 6.

| Formulation | Temperature | Appearance | Turbidity Avg. O.D. 340–360 nm |
|---|---|---|---|
| T = 8 weeks | | | |
| Acetate pH 5 | | Clear | 0.051 ± 0.001 |
| Histidine pH 5 | 2–8° C. | Clear | 0.065 ± 0.0002 |
| Histidine pH 6 | | Clear | 0.068 ± 0.001 |
| Acetate pH 5 | 40° C. | Opalescent | 0.16 ± 0.002 |
| Histidine pH 5 | 40° C. | Light yellow, Opalescent | 0.28 ± 0.015 |
| Histidine pH 6 | 40° C. | Light yellow, Opalescent | 0.36 ± 0.026 |
| T = 4 weeks | | | |
| Acetate pH 5 | 50° C. | Very Opalescent | 0.61 ± 0.007 |
| Histidine pH 5 | 50° C. | Firm opaque gel | N/D[1] |
| Histidine pH 6 | 50° C. | Cloudy, yellow solution | 1.30 ± 0.20 |

[1]The turbidity was not determined (N/D) due to the gelation of the sample.

The stability was also monitored by HIC and SEC HPLC methods. After eight weeks storage at 40° C., the acetate pH 5 formulations were unchanged while the histidine pH 6 formulations had a 18 percent reduction in unoxidized Fc relative to the initial bmepoint (Table 19). The percentage monomer decreased in all formulations stored at 40° C. with the histidine pH 6 being slightly more stable. This reduction was attributed to the formation of a high molecular weight aggregate(s) eluting at the void volume, a lagging shoulder on the monomer peak and lower molecular weight species. The protein concentration and pH were also measured, except in the case of gelation, and no changes were observed over the duration of the study.

TABLE 19

The effect of buffer species and pH on the percentage unoxidized Fc and percentage monomer of 40 mg/mL rhuMAb CD20 multidose formulations containing 50 mM acetate or histidine, 150 mM trehalose, 0.9% benzyl alcohol and 0.02% polysorbate 20 at pH 5 or 6.

| Formulation | Temperature | % Unoxidized Fc (HIC HPLC) | % Monomer (SEC HPLC) |
|---|---|---|---|
| T = 0 | | | |
| Acetate pH 5 | 2–8° C. | 93.9 | 99.4 |
| Histidine pH 5 | 2–8° C. | 99.1 | 99.4 |
| Histidine pH6 | 2–8° C. | 99.3 | 98.5 |
| T = 8 weeks | | | |
| Acetate pH 5 | 40° C. | 96.5 | 90.4 |
| Histidine pH 5 | 40° C. | 87.0 | 87.4 |
| Histidine pH 6 | 40° C. | 81.7 | 93.9 |

Since the acetate pH 5 formulation had only a slightly higher aggregation rate, did not turn yellow upon storage at high temperatures and had the greatest clarity under all conditions studied, it was chosen as the buffer species and pH of choice for all subsequent liquid C2B8 multidose formulation screens.

Amount of buffering species: The amount of acetate which maintained the pH of a 40 mg/mL C2B8 multidose formulation at 5.0 was determined. Summarized in Table 20 is the effect on pH as the acetate buffer concentration was increased from 10 to 30 mM. At two and four weeks there appeared to be a slight advantage in staying above 15 mM acetate, although this did not hold true upon long term storage. No change was seen in the pH in any of the test formulations studied after one years storage at 2–8° C. A range of 10 to 30 mM acetate is sufficient to maintain the pH at 5.0.

TABLE 20

The effect of acetate buffer concentration on maintaining the pH of liquid rhuMAb CD20 multidose formulations at 5.0. The formulations were composed of 40 mg/mL rhuMAb CD20, 10 to 30 mM acetate, 150 mM trehalose, 0.9% benzyl alcohol, 0.02% polysorbate 20 at pH 5.0.

| mM | pH (weeks) | | | |
|---|---|---|---|---|
| Acetate | 0 | 2 | 4 | 56 |
| 2–8° C. | | | | |
| 10 | 5.03 | 5.12 | 5.11 | 5.00 |
| 15 | 5.07 | 5.12 | 5.14 | 5.06 |
| 20 | 5.04 | 5.04 | 5.04 | 5.00 |
| 25 | 5.01 | 5.00 | 5.02 | 4.98 |
| 30 | 5.01 | 5.00 | 5.02 | 4.98 |
| 40° C. | | | | |
| 10 | | 5.12 | 5.14 | |
| 15 | | 5.10 | 5.17 | |
| 20 | | 5.08 | 5.10 | |
| 25 | | 5.05 | 5.05 | |
| 30 | | 5.03 | 5.05 | |

Figure 25:
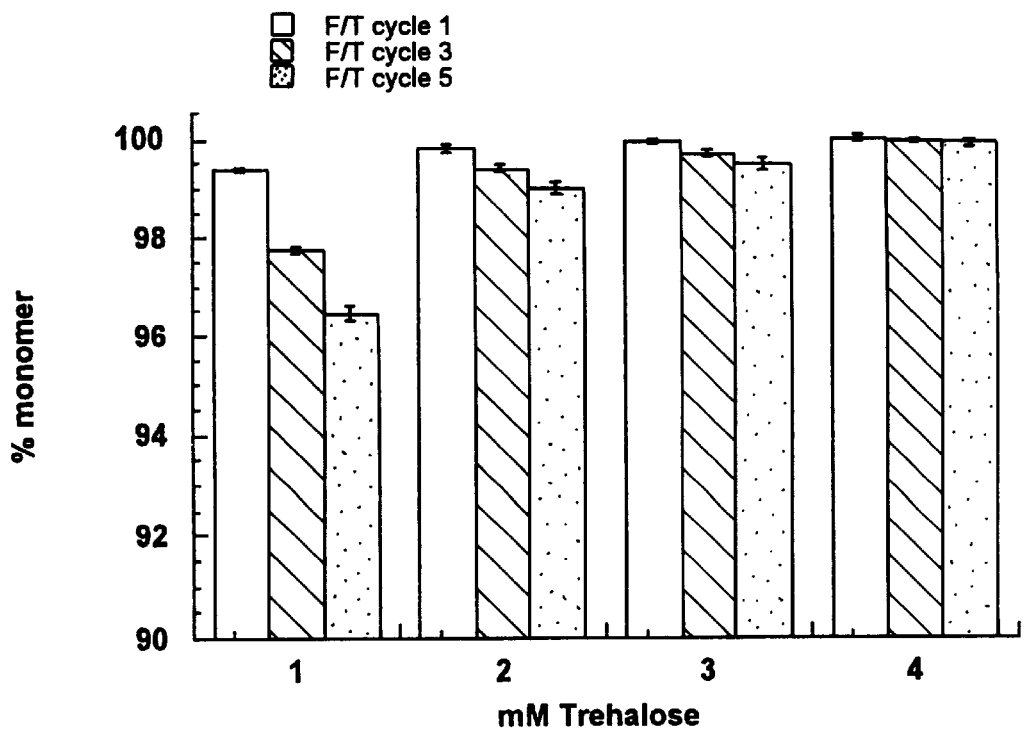
FIG. 25 depicts the effect of excess molar ratios of trehalose on the freeze-thaw induced aggregation of rhuMAb CD20 multidose formulations. Each formulation is composed of 40 mg/mL rhuMAb CD20, 20 mM acetate, 0 to 1000:1 molar ratio of trehalose, 0.9% benzyl alcohol and 0.02% polysorbate 20, pH 5.0 The amount of trehalose in formulations 1–4 was follows: 1=0 moles trehalose: 1 mole of rhuMAb CD20 (0 mM trehalose); 2=250 moles trehalose.

Ratio of tonicity modifier: protein: The addition of trehalose was beneficial to the stability of rhuMAb CD20 multdose formulations after multiple freeze/thaw cycles (FIG. 25). A decrease in the formation of soluble aggregates was observed as the concentration of trehalose in the formulation was increased. At a ratio of 500 moles trehalose:1 mole C2B8 (134 mM trehalose), the percentage of aggregate formed was only 0.5% after five freeze-thaw cycles while the control formulation containing no isotonicity modifier formed 4% aggregate. Having at least a 500 fold molar excess of trehalose in the liquid C2B8 formulation offered sufficient protection against freeze induced aggregation.

The ability of trehalose to stabilize rhuMAb CD20 during accelerated temperature storage was studied and compared to sodium chloride.

FIG. 26 describes the effect of excess molar ratios of trehalose or sodium chloride on the clarity of test formulations stored at 40° C. Sodium chloride is deleterious to the stability. After two weeks storage at 40° C., the 500:1 ratio sample had an O.D. of 0.44. At a 1000:1 molar ratio, the sodium chloride containing formulation separated into a two phase system composed of an opaque gel covered with an opalescent fluid on top. In contrast, there was little change in the solution clarity of the samples containing 0 to 1000:1 molar ratio of trehalose even after one months storage at 40° C. Although the 2–8° C. formulations were unchanged from the initial bmepoint, the sodium chloride containing samples were more opalescent.

The effect of trehalose on minimizing the soluble aggregate formation was assessed by SEC HPLC (FIG. 27). No differences were observed between the trehalose formulations and the negative control which contained no tonicity modifier. The formulations appeared to degrade at the same rate to the same products upon storage at 40° C. The pH and concentration were also maintained over the duration of the study.

The presence of trehalose is beneficial in minimizing freeze-induced aggregation and is not deleterious to the stability in the liquid state. The candidate liquid multidose formulation preferably contains at least 500:1 molar ratio of trehalose to C2B8.

Stability of candidate liquid multidose formulation: Based on the aforementioned studies, a protoype liquid multidose formulation composed of 40 mg/mL rhuMAb CD20, 25 mM acetate, 150 mM trehalose, 0.9% benzyl alcohol and 0.02% polysorbate 20 at pH 5.0 was placed on stability at 2–8°, 30° C. and 40° C. The stability profile by SEC HPLC at each temperature studied is shown in FIG. 28. Although the rate of aggregation is slightly faster at 40° C. for the multidose formulation (40 mg/mL) compared to the reference control (10 mg/mL rhuMAb CD20, 25 mM citrate, 150 mM sodium chloride, 0.07% polysorbate 80 at pH 6.5), no decrease in percentage monomer was observed upon storage at 2–8° C. for two years. The bioactivity of the two year old 2–8° C. samples was 99.2% relative to the reference control as determined by the CDC assay.

CONCLUSIONS

The above screening studies indicated that a stable high concentration rhuMAb CD20 liquid multidose formulation was possible by buffering with acetate, maintaining the pH at 5 and including preferably at least about 500 moles of trehalose per mole of antibody. The preferred liquid multidose configuration is composed of 40 mg/mL rhuMAb CD20, 25 mM acetate, 150 mM trehalose, 0.9% benzyl alcohol and 0.02% polysorbate 20 at pH 5 and has a shelf life of two years at 2–8° C.

What is claimed is:

1. A stable aqueous pharmaceutical formulation comprising a therapeutically effective amount of an antibody not subjected to prior lyophilization, an acetate buffer from about pH 4.8 to about 5.5, a surfactant and a polyol, wherein the formulation lacks a tonicifying amount of sodium chloride.

2. The formulation of claim 1 which is isotonic.

3. The formulation of claim 1 which is stable at a temperature of about 2–8° C. for at least one year.

4. The formulation of claim 1 which is stable following freezing and thawing of the formulation.

5. The formulation of claim 1 which is stable at about 30° C. for at least one month.

6. The formulation of claim 1 wherein the polyol is a nonreducing sugar.

7. The formulation of claim 6 wherein the nonreducing sugar is trehalose.

8. The formulation of claim 6 wherein the nonreducing sugar is sucrose.

9. The formulation of claim 1 wherein the antibody is an antibody fragment.

10. The formulation of claim 9 wherein the antibody fragment is a F(ab')$_2$.

11. The formulation of claim 1 wherein the antibody binds CD18.

12. The formulation of claim 1 which is stable at a temperature of about 2–8° C. for at least two years.

13. The formulation of claim 1 wherein the antibody concentration in the formulation is from about 0.1 to about 50 mg/mL.

14. The formulation of claim 1 wherein the surfactant is a polysorbate.

15. The formulation of claim 1 wherein the antibody binds CD20.

16. The formulation of claim 15 wherein the acetate is present in an amount of about 5–30 mM.

17. The formulation of claim 16 wherein the acetate is present in an amount of 10–30 mM.

18. The formulation of claim 15 further comprising a preservative.

19. The formulation of claim 18 wherein the preservative is benzyl alcohol.

20. The formulation of claim 15 wherein the antibody is present in an amount of about 30–50 mg/mL.

21. The formulation of claim 20 wherein the buffer is 10–30 mM sodium acetate at pH 5, the polyol is trehalose in an amount of about 2–10% w/v, the surfactant is polysorbate in an amount of about 0.01–0.1% v/v, wherein the formulation further comprises benzyl alcohol as a preservative and wherein the formulation is stable at a temperature of about 2–8° C. for at least two years.

22. An article of manufacture comprising a container holding a stable aqueous pharmaceutical formulation comprising a therapeutically effective amount of an antibody not subjected to prior lyophilization, an acetate buffer from about pH 4.8 to about 5.5, a surfactant and a polyol, wherein the formulation lacks a tonicifying amount of sodium chloride.

23. A method for stabilizing an antibody in an aqueous pharmaceutical formulation by combining a therapeutically effective amount of an antibody not subjected to prior lyophilization, an acetate buffer from about pH 4.8 to about 5.5, a surfactant and a polyol, wherein the formulation lacks a tonicifying amount of sodium chloride.

24. A stable aqueous pharmaceutical formulation comprising a therapeutically effective amount of an antibody not subjected to prior lyophilization, a 10–30 mM acetate buffer at pH 5.0, a surfactant, and trehalose at a concentration of at least 134 mM, wherein the formulation lacks a tonicifying amount of sodium chloride.

25. The formulation of claim 24 wherein the antibody binds CD18 or CD20.

26. The formulation of claim 25 wherein the CD18 binding antibody is a F(ab')$_2$ fragment.

27. An article of manufacture comprising a container holding the formulation of claim 25.

28. The formulation of claim 1, wherein the acetate buffer is at pH 5.0.

29. The formulation of claim 28, wherein the antibody binds CD20.

* * * * *